(12) United States Patent
Lieber et al.

(10) Patent No.: US 7,595,260 B2
(45) Date of Patent: Sep. 29, 2009

(54) DOPED ELONGATED SEMICONDUCTORS, GROWING SUCH SEMICONDUCTORS, DEVICES INCLUDING SUCH SEMICONDUCTORS, AND FABRICATING SUCH DEVICES

(75) Inventors: Charles M. Lieber, Lexington, MA (US); Yi Cui, Union City, CA (US); Xiangfeng Duan, Mountain View, CA (US); Yu Huang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 251 days.

(21) Appl. No.: 11/543,326

(22) Filed: Oct. 4, 2006

(65) Prior Publication Data

US 2007/0026645 A1 Feb. 1, 2007

Related U.S. Application Data

(63) Continuation of application No. 09/935,776, filed on Aug. 22, 2001, now abandoned.

(60) Provisional application No. 60/226,835, filed on Aug. 22, 2000, provisional application No. 60/254,745, filed on Dec. 11, 2000, provisional application No. 60/292,035, filed on May 18, 2001, provisional application No. 60/292,121, filed on May 18, 2001, provisional application No. 60/292,045, filed on May 18, 2001, provisional application No. 60/291,896, filed on May 18, 2001.

(51) Int. Cl.
*H01L 21/30* (2006.01)
*H01L 21/86* (2006.01)

(52) U.S. Cl. .................. 438/495; 438/499; 977/858; 977/882

(58) Field of Classification Search ............... 438/493, 438/495, 499, 501; 977/841, 854, 857–859, 977/882, 762
See application file for complete search history.

(56) References Cited

U.S. PATENT DOCUMENTS 3,873,359 A 3/1975 Lando (Continued)

FOREIGN PATENT DOCUMENTS

CN 1110786 10/1995

(Continued)

OTHER PUBLICATIONS

Agarwal, et al., "Lasing in Single Cadmium Sulfide Nanowire Optical Cavities," *Nano-Lett*, 5(5):917-920 (2005).

(Continued)

*Primary Examiner*—Thanhha Pham
(74) *Attorney, Agent, or Firm*—Wolf, Greenfield & Sacks, P.C.

(57) ABSTRACT

A bulk-doped semiconductor may be at least one of the following: a single crystal, an elongated and bulk-doped semiconductor that at any point along its longitudinal axis, has a largest cross-sectional dimension less than 500 nanometers, and a free-standing and bulk-doped semiconductor with at least one portion having a smallest width of less than 500 nanometers. At least one portion of such a semiconductor may have a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers. Such a semiconductor may be doped during growth. Such a semiconductor may be part of a device, which may include any of a variety of devices and combinations thereof.

10 Claims, 43 Drawing Sheets

U.S. PATENT DOCUMENTS

| | | |
|---|---|---|
| 3,873,360 A | 3/1975 | Lando |
| 3,900,614 A | 8/1975 | Lando |
| 4,673,474 A | 6/1987 | Ogawa |
| 4,939,556 A | 7/1990 | Eguchi et al. |
| 5,023,139 A | 6/1991 | Birnboim et al. |
| 5,089,545 A | 2/1992 | Pol |
| 5,252,835 A | 10/1993 | Lieber et al. |
| 5,274,602 A | 12/1993 | Glenn |
| 5,453,970 A | 9/1995 | Rust et al. |
| 5,475,341 A | 12/1995 | Reed |
| 5,512,131 A | 4/1996 | Kumar et al. |
| 5,524,092 A | 6/1996 | Park |
| 5,537,075 A | 7/1996 | Miyazaki |
| 5,539,214 A | 7/1996 | Lynch et al. |
| 5,581,091 A | 12/1996 | Moskovits et al. |
| 5,589,692 A | 12/1996 | Reed |
| 5,607,876 A | 3/1997 | Biegelsen et al. |
| 5,620,850 A | 4/1997 | Bamdad et al. |
| 5,640,343 A | 6/1997 | Gallagher et al. |
| 5,726,524 A | 3/1998 | Debe |
| 5,739,057 A | 4/1998 | Tiwari et al. |
| 5,747,180 A | 5/1998 | Miller et al. |
| 5,751,156 A | 5/1998 | Muller et al. |
| 5,776,748 A | 7/1998 | Singhvi et al. |
| 5,824,470 A | 10/1998 | Baldeschwieler et al. |
| 5,830,538 A | 11/1998 | Gates et al. |
| 5,840,435 A | 11/1998 | Lieber et al. |
| 5,847,565 A | 12/1998 | Narayanan |
| 5,858,862 A | 1/1999 | Westwater et al. |
| 5,864,823 A | 1/1999 | Levitan |
| 5,866,434 A | 2/1999 | Massey et al. |
| 5,897,945 A | 4/1999 | Lieber et al. |
| 5,900,160 A | 5/1999 | Whitesides et al. |
| 5,903,010 A | 5/1999 | Flory et al. |
| 5,908,692 A | 6/1999 | Hamers et al. |
| 5,916,642 A | 6/1999 | Chang |
| 5,942,443 A | 8/1999 | Parce et al. |
| 5,997,832 A | 12/1999 | Lieber et al. |
| 6,004,444 A | 12/1999 | Aksay et al. |
| 6,036,774 A | 3/2000 | Lieber et al. |
| 6,038,060 A | 3/2000 | Crowley |
| 6,060,121 A | 5/2000 | Hidber et al. |
| 6,060,724 A | 5/2000 | Flory et al. |
| 6,069,380 A | 5/2000 | Chou et al. |
| 6,123,819 A | 9/2000 | Peeters |
| 6,128,214 A | 10/2000 | Kuekes et al. |
| 6,143,184 A | 11/2000 | Martin et al. |
| 6,149,819 A | 11/2000 | Martin et al. |
| 6,159,742 A | 12/2000 | Lieber et al. |
| 6,180,239 B1 | 1/2001 | Whitesides et al. |
| 6,187,165 B1 | 2/2001 | Chien et al. |
| 6,190,634 B1 | 2/2001 | Lieber et al. |
| 6,203,864 B1 | 3/2001 | Zhang et al. |
| 6,207,392 B1 | 3/2001 | Weiss et al. |
| 6,211,464 B1 | 4/2001 | Mochizuki et al. |
| 6,231,744 B1 | 5/2001 | Ying et al. |
| 6,256,767 B1 | 7/2001 | Kuekes et al. |
| 6,270,074 B1 | 8/2001 | Rasmussen et al. |
| 6,278,231 B1 | 8/2001 | Iwasaki et al. |
| 6,286,226 B1 | 9/2001 | Jin |
| 6,287,765 B1 | 9/2001 | Cubicciotti |
| 6,314,019 B1 | 11/2001 | Kuekes et al. |
| 6,325,904 B1 | 12/2001 | Peeters |
| 6,340,822 B1 | 1/2002 | Brown et al. |
| 6,346,189 B1 | 2/2002 | Dai et al. |
| 6,355,198 B1 | 3/2002 | Kim et al. |
| 6,359,288 B1 | 3/2002 | Ying et al. |
| 6,437,329 B1 | 8/2002 | Yedur et al. |
| 6,440,637 B1 * | 8/2002 | Choi et al. .......... 430/296 |
| 6,451,113 B1 | 9/2002 | Givargizov |
| 6,459,095 B1 | 10/2002 | Heath et al. |
| 6,465,132 B1 | 10/2002 | Jin |
| 6,468,657 B1 | 10/2002 | Hou et al. |
| 6,468,677 B1 | 10/2002 | Benton et al. |
| 6,503,375 B1 | 1/2003 | Maydan et al. |
| 6,528,020 B1 | 3/2003 | Dai et al. |
| 6,538,367 B1 | 3/2003 | Choi et al. |
| 6,559,468 B1 | 5/2003 | Kuekes et al. |
| 6,586,095 B2 | 7/2003 | Wang et al. |
| 6,628,053 B1 | 9/2003 | Den et al. |
| 6,716,409 B2 | 4/2004 | Hafner et al. |
| 6,741,019 B1 | 5/2004 | Filas et al. |
| 6,743,408 B2 | 6/2004 | Lieber et al. |
| 6,756,025 B2 | 6/2004 | Colbert et al. |
| 6,756,795 B2 | 6/2004 | Hunt et al. |
| 6,762,056 B1 | 7/2004 | Peeters |
| 6,781,166 B2 | 8/2004 | Lieber et al. |
| 6,803,840 B2 | 10/2004 | Hunt et al. |
| 6,808,746 B1 | 10/2004 | Dai et al. |
| 6,815,706 B2 | 11/2004 | Li et al. |
| 6,846,565 B2 | 1/2005 | Korgel et al. |
| 6,872,645 B2 | 3/2005 | Duan et al. |
| 6,882,051 B2 | 4/2005 | Majumdar et al. |
| 6,882,767 B2 | 4/2005 | Yang et al. |
| 6,902,720 B2 | 6/2005 | McGimpsey |
| 6,946,197 B2 | 9/2005 | Yadav et al. |
| 6,958,216 B2 | 10/2005 | Kelley et al. |
| 6,962,823 B2 | 11/2005 | Empedocles et al. |
| 6,974,706 B1 | 12/2005 | Melker et al. |
| 6,996,147 B2 | 2/2006 | Majumdar et al. |
| 7,048,903 B2 | 5/2006 | Colbert et al. |
| 7,129,554 B2 | 10/2006 | Lieber et al. |
| 7,172,953 B2 | 2/2007 | Lieber et al. |
| 7,211,464 B2 | 5/2007 | Lieber et al. |
| 7,254,151 B2 | 8/2007 | Lieber et al. |
| 7,256,466 B2 | 8/2007 | Lieber et al. |
| 7,301,199 B2 | 11/2007 | Lieber et al. |
| 7,303,875 B1 | 12/2007 | Bock et al. |
| 7,335,908 B2 | 2/2008 | Samuelson et al. |
| 7,385,267 B2 | 6/2008 | Lieber et al. |
| 7,399,691 B2 | 7/2008 | Lieber et al. |
| 2001/0054709 A1 | 12/2001 | Heath et al. |
| 2002/0013031 A1 | 1/2002 | Chen et al. |
| 2002/0040805 A1 | 4/2002 | Swager |
| 2002/0055239 A1 | 5/2002 | Tuominen et al. |
| 2002/0084502 A1 | 7/2002 | Jang et al. |
| 2002/0086335 A1 | 7/2002 | Massey et al. |
| 2002/0112814 A1 | 8/2002 | Hafner et al. |
| 2002/0117659 A1 | 8/2002 | Lieber et al. |
| 2002/0122766 A1 | 9/2002 | Lieber et al. |
| 2002/0130311 A1 | 9/2002 | Lieber et al. |
| 2002/0130353 A1 | 9/2002 | Lieber et al. |
| 2002/0146714 A1 | 10/2002 | Lieber et al. |
| 2002/0158342 A1 | 10/2002 | Tuominen et al. |
| 2002/0172820 A1 | 11/2002 | Majumdar et al. |
| 2002/0175408 A1 | 11/2002 | Majumdar et al. |
| 2002/0179434 A1 | 12/2002 | Dai et al. |
| 2002/0187504 A1 | 12/2002 | Reich et al. |
| 2003/0001091 A1 | 1/2003 | Nakayama et al. |
| 2003/0003300 A1 | 1/2003 | Korgel et al. |
| 2003/0032892 A1 | 2/2003 | Erlach et al. |
| 2003/0048619 A1 | 3/2003 | Kaler et al. |
| 2003/0073071 A1 | 4/2003 | Fritz et al. |
| 2003/0089899 A1 | 5/2003 | Lieber et al. |
| 2003/0098488 A1 | 5/2003 | O'Keeffe et al. |
| 2003/0113713 A1 | 6/2003 | Glezer et al. |
| 2003/0113940 A1 | 6/2003 | Erlanger et al. |
| 2003/0121764 A1 | 7/2003 | Yang et al. |
| 2003/0124509 A1 | 7/2003 | Kenis et al. |
| 2003/0124717 A1 | 7/2003 | Awano et al. |
| 2003/0134267 A1 | 7/2003 | Kang et al. |
| 2003/0134433 A1 | 7/2003 | Gabriel et al. |
| 2003/0135971 A1 | 7/2003 | Liberman et al. |
| 2003/0156992 A1 | 8/2003 | Anderson et al. |

| | | | | | | |
|---|---|---|---|---|---|---|
| 2003/0186522 A1 | 10/2003 | Duan | | WO | WO 96/29629 A2 | 9/1996 |
| 2003/0186544 A1 | 10/2003 | Matsui et al. | | WO | WO 97/32571 A1 | 3/1997 |
| 2003/0189202 A1 | 10/2003 | Li et al. | | WO | WO 97/34140 A1 | 3/1997 |
| 2003/0197456 A1 | 10/2003 | Den et al. | | WO | WO 97/33737 A1 | 9/1997 |
| 2003/0200521 A1 | 10/2003 | DeHon et al. | | WO | WO 97/34025 A1 | 9/1997 |
| 2004/0005723 A1 | 1/2004 | Empedocles et al. | | WO | WO 98/39250 A1 | 9/1998 |
| 2004/0026684 A1 | 2/2004 | Empedocles | | WO | WO 98/42620 A1 | 10/1998 |
| 2004/0067530 A1 | 4/2004 | Gruner | | WO | WO 98/48456 A1 | 10/1998 |
| 2004/0075464 A1 | 4/2004 | Samuelson et al. | | WO | WO 99/24823 A1 | 11/1998 |
| 2004/0095658 A1 | 5/2004 | Buretea et al. | | WO | WO 99/63347 A2 | 12/1999 |
| 2004/0106203 A1 | 6/2004 | Stasiak et al. | | WO | WO 00/09443 A1 | 2/2000 |
| 2004/0112964 A1 | 6/2004 | Empedocles et al. | | WO | WO 00/17101 A1 | 3/2000 |
| 2004/0113138 A1 | 6/2004 | DeHon et al. | | WO | WO 00/19494 A1 | 4/2000 |
| 2004/0113139 A1 | 6/2004 | DeHon et al. | | WO | WO 00/29617 A3 | 5/2000 |
| 2004/0118448 A1 | 6/2004 | Scher et al. | | WO | WO 00/51186 A2 | 8/2000 |
| 2004/0136866 A1 | 7/2004 | Pontis et al. | | WO | WO 01/03208 AI | 1/2001 |
| 2004/0146560 A1 | 7/2004 | Whiteford et al. | | WO | WO 01/44796 | 6/2001 |
| 2004/0157414 A1 | 8/2004 | Gole et al. | | WO | WO 02/17362 A2 | 2/2002 |
| 2004/0188721 A1 | 9/2004 | Lieber et al. | | WO | WO 02/31183 A1 | 4/2002 |
| 2004/0191517 A1 | 9/2004 | Drake | | WO | WO 02/48701 A2 | 6/2002 |
| 2004/0213307 A1 | 10/2004 | Lieber et al. | | WO | WO 02/080280 A1 | 10/2002 |
| 2005/0037374 A1 | 2/2005 | Melker et al. | | WO | WO 02/086480 A1 | 10/2002 |
| 2005/0064185 A1 | 3/2005 | Buretea et al. | | WO | WO 03/005450 A2 | 1/2003 |
| 2005/0064731 A1 | 3/2005 | Park et al. | | WO | WO 03/016901 A1 | 2/2003 |
| 2005/0066883 A1 | 3/2005 | Dubrow et al. | | WO | WO 03/053851 A2 | 7/2003 |
| 2005/0072213 A1 | 4/2005 | Besnard et al. | | WO | WO 03/054931 A1 | 7/2003 |
| 2005/0079533 A1 | 4/2005 | Samuelson et al. | | WO | WO 03/063208 A2 | 7/2003 |
| 2005/0079659 A1 | 4/2005 | Duan et al. | | WO | WO 2004/003535 A1 | 1/2004 |
| 2005/0100960 A1 | 5/2005 | Dai et al. | | WO | WO 2004/010552 A1 | 1/2004 |
| 2005/0101026 A1 | 5/2005 | Sailor et al. | | WO | WO 2004/032190 A2 | 4/2004 |
| 2005/0109989 A1 | 5/2005 | Whiteford et al. | | WO | WO 2004/032193 A2 | 4/2004 |
| 2005/0110064 A1 | 5/2005 | Duan et al. | | WO | WO 2004/034025 A2 | 4/2004 |
| 2005/0117441 A1 | 6/2005 | Lieber et al. | | WO | WO 2004/038767 A2 | 5/2004 |
| 2005/0161662 A1 | 7/2005 | Majumdar et al. | | WO | WO 2005/114282 A2 | 2/2005 |
| 2005/0181587 A1 | 8/2005 | Duan et al. | | WO | WO 2005/089165 A2 | 9/2005 |
| 2005/0201149 A1 | 9/2005 | Duan et al. | | WO | WO 2005/093831 A1 | 10/2005 |
| 2005/0202615 A1 | 9/2005 | Duan et al. | | WO | WO 2005/094440 A2 | 10/2005 |
| 2005/0212079 A1 | 9/2005 | Stumbo et al. | | WO | WO 2005/119753 A2 | 12/2005 |
| 2005/0214967 A1 | 9/2005 | Scher et al. | | WO | WO 2006/107312 | 10/2006 |
| 2005/0219788 A1 | 10/2005 | Chow et al. | | WO | WO 2006/132659 | 12/2006 |
| 2005/0230356 A1 | 10/2005 | Empedocles et al. | | WO | WO 2007/044034 | 4/2007 |
| 2005/0253137 A1 | 11/2005 | Whang et al. | | WO | WO 2007/145701 A2 | 12/2007 |
| 2005/0266662 A1 | 12/2005 | Yi | | WO | WO 2008/027078 A2 | 3/2008 |
| 2005/0287717 A1 | 12/2005 | Heald et al. | | WO | WO 2008/033303 A2 | 3/2008 |
| 2006/0008942 A1 | 1/2006 | Romano et al. | | WO | WO 2008/123869 A2 | 10/2008 |
| 2006/0009003 A1 | 1/2006 | Romano et al. | | WO | WO 2008/127314 A1 | 10/2008 |
| 2006/0019472 A1 | 1/2006 | Pan et al. | | | | |
| 2006/0054936 A1 | 3/2006 | Lieber et al. | | | | |
| 2006/0057360 A1 | 3/2006 | Samuelson et al. | | | | |
| 2006/0160246 A1 | 7/2006 | Massey et al. | | | | |
| 2006/0175601 A1 | 8/2006 | Lieber et al. | | | | |
| 2006/0237749 A1 | 10/2006 | Lieber et al. | | | | |
| 2006/0269927 A1 | 11/2006 | Lieber et al. | | | | |
| 2007/0026645 A1 | 2/2007 | Lieber et al. | | | | |
| 2007/0032023 A1 | 2/2007 | Lieber et al. | | | | |
| 2007/0032051 A1 | 2/2007 | Lieber et al. | | | | |
| 2007/0032052 A1 | 2/2007 | Lieber et al. | | | | |
| 2007/0048492 A1 | 3/2007 | Lieber et al. | | | | |
| 2007/0252136 A1 | 11/2007 | Lieber et al. | | | | |
| 2007/0281156 A1 | 12/2007 | Lieber et al. | | | | |
| 2008/0191196 A1 | 8/2008 | Lu et al. | | | | |
| 2009/0004852 A1 | 1/2009 | Lieber et al. | | | | |

FOREIGN PATENT DOCUMENTS

| | | |
|---|---|---|
| EP | 1 087 413 A2 | 3/2001 |
| EP | 1170799 A2 | 1/2002 |
| JP | 09-191104 | 7/1997 |
| JP | 11-11917 A2 | 1/1999 |
| JP | 2000-31462 A | 1/2000 |
| JP | 2001/281965 | 10/2001 |
| WO | WO 91/06036 A1 | 5/1991 |
| WO | WO 95/02709 A2 | 1/1995 |

OTHER PUBLICATIONS

Chen, "Noncovalent functionalization of carbon nanotubes for highly specific electronic biosensors," *PNAS*,100(9):4984-4989 (2003).

Chen, J., et al., "Large On-Off Ratios and Negative Differential Resistance in a Molecular Electronic Device," *Science*, 286: 1550-51 (1999).

Cheung, C.L., et al., "Diameter Controlled Synthesis of Carbon Nanotubes," *J. Phys. Chem B*, 106, (2002), pp. 2429-2433.

Choi, "Enhancement of Ferroelectricity in Strained BaTiO$_3$ Thin Films," Science, 306:1005-1009 (2004).

Chung, et al., "Silicon nanowire devices", *Appl Phys Lett*, 76(15): 2068-2070 (2000).

Collier, C.P., et al., "Electronically Configurable Molecular-Based Logic Gates", *SCIENCE*, vol. 285, Jul. 16, 1999, pp. 391-394.

Cui et al., "Nanowire nanosensors for highly sensitive and selective detection of biological and chemical species", Science, Aug. 17, 2001, vol. 293, pp. 1289-1292.

Cui, Yi, et al. "Doping and Electrical Transport in Silicon Nanowires", *The Journal of Physical Chemistry*, vol. 104, No. 22, Jun. 8, 2000, pp. 5213-5216.

Cui, Yi, et al., "Diameter-controlled synthesis of single-crystal silicon nanowires", *Applied Physics Letters*, vol. 78, No. 15, Apr. 9, 2001, pp. 2214-2216.

Cui, Yu, et al., "Functional Nanoscale Electronic Devices Assembled Using Silicon Nanowire Building Blocks", *Science*, vol. 291, Feb. 2, 2001, pp. 851-853;.

Duan, "Synthesis and optical properties of gallium arsenide nanowires," *Apl Phys Lett*, 76(9): 1116-1118 (2000).

Duan, X., et al., "High-performance thin-film transistors using semiconductor nanowires and nanoribbons", *Nature*, 425: 274-278 (2003).

Duan, X., et al., "Nonvolatile Memory and Programmable Logic from Molecule-Gated Nanowires," *Nano Letters*, 2(5), (2002), pp. 487-490.

Duan, X., et al., "Single-nanowire electrically driven lasers," *Nature*, 421, (2003), pp. 241-245.

Duan, Xiangfeng, et al., "General Synthesis of Compound Semiconductor Nanowires", *Adv. Materials. 2000*, 12, No. 4, pp. 298-302, published on Web Feb. 17, 2000.

Duan, Xiangfeng et al., "Indium phosphide nanowires as building blocks for nanoscale electronic and optoelectronic devices", *Nature*, vol. 409, Jan. 4, 2001, pp. 66-69.

Duan, Xiangfeng et al., "Laser-Assisted Catalytic Growth of Single Crystal GaN Nanowires", *J. Am. Chem. Soc. 2000*, 122, Oct. 18, 1999, pp. 188-189; published on Web Dec. 18, 1999.

Esfarjani, K., et al., "Electronic and transport properties of N-P doped nanotubes", *Appl Phy Lett*, 74(1): 79-81 (1999).

Friedman, "High-speed integrated nanowire circuits," *Nature*, 434: 1085 (2005).

Givargizov, E.I., et al., "Fundamental Aspects of VLS Growth," *J. Crystal Growth*, 31, (1975), pp. 20-30.

Gradecak, "GaN nanowire lasers with low lasing thresholds," *Apl Phys Lett*, (87): 173111-173111-3 (2005).

Gudiksen et al., "Growth of nanowire superlattice structures for nanoscale photonics and electronics", *Nature*, 2002, vol. 415, pp. 617-620.

Gudiksen, M.S., et al., "Size-Dependent Photoluminescence from Single Indium Phosphide Nanowires," *J. Phys. Chem. B*, 106, (2002), pp. 4036-4039.

Gudiksen, M.S., et al., "Synthetic Control of the Diameter and Length of Single Crystal Semiconductor Nanowires," *J. Phys. Chem. B*, 105, (2001), pp. 4062-4064.

Gudiksen, Mark S., et al. "Diameter-Selective Synthesis of Semiconductor Nanowires", *J. Am. Chem. Soc. 2000*, 122, Jun. 6, 2000, pp. 8801-8802.

Guo, et al., "Nanoscale Silicon Field Effect Transistors Fabricated Using Imprint Lithography," *Appl Phys Lett*, 71(13):1881-1883; (1997).

Guo, L., et al., "A Silicon Single-Electron Transistor Memory Operating at Room Temperature," *Science*, 275: 649-651(1997).

Hahm, "Direct Ultrasensitive Electrical Detection of DNA and DNA Sequence Variations Using nanowire Nanosensors," *Nano-Lett*, 4(1): 51-54 (2003).

Haraguchi et al, "Polarization dependence of light emitted from GaAs p-n junctions in quantum wire crystals", *Journal of Applied Physics*, Apr. 1994, vol. 75, No. 8, pp. 4220-4225.

Haraguchi, et al., "GaAs p-n junction formed in quantum wire crystals", *Appl Phys Lett*, 60: 745-747 (1992).

Heath, "A liquid solution synthesis of single crystal germanium quantum wires," *Chem Phys Lett*, 208(3,4):263-265 (1993).

Hiruma, "GaAs free-standing quantum-size wires," *J Apl Phys*, 74(5):3 162-3171 (1993).

Hiruma, K., et al., "Self-organized growth of GaAs/InAs heterostructure nanocylinders by organometallic vapor phase epitaxy," *J. Crystal Growth*, 163, (1996), pp: 226-231.

Holmes, et al., "Control of Thickness and Orientation of Solution-Grown Silicon Nanowires, Science, 287, (2000), pp. 1471-1473.

Hsu, S.T., et al. "Mfmox Ferroelectric Memory Transistor," Non-Volatile Memory Technology Symposium, Orlando, Fl, Nov. 15-17, 2004, p. 24-27.

Hu, J "Serpentine Superlattice nanowire-Array Lasers," *Quant Elec*, 31(8):1380-1388 (1995).

Hu, J., et al., "Chemistry and Physics in One Dimension: Synthesis and Properties of Nanowires and Nanotubes," *Acc. Chem. Res.*, 32, (1999), pp. 435-445.

Hu, J., et al., "Controlled growth and electrical properties of heterojunctions of carbon nanotubes and silicon nanowires," *Nature*, 399, (1999), pp. 48-51.

Hu, S.-Y., "Serpentine Superlattice Nanowire-Array Lasers, "*J. Quant. Electron.*, 31(8), (1995), pp. 1380-1388.

Huang, et al., "Logic Gates and Computation from Assembled Nanowire Building Blocks", *Science*, 294: 1313-1317 (2001).

Huang, M., et al., "Room-Temperature Ultraviolet Nanowire Nanolasers," *Science*, 292, (2001), pp. 1897-1898.

Huang, Y., et al., "Gallium Nitride Nanowire Nanodevices," *Nano Letters*, 2(2), (2002), pp. 101-104.

Huang, Yu, et al., "Directed Assembly of One-dimensional Nanostructures into Functional Networks", *Science*, vol. 291, Jan. 26, 2001, pp. 630-633.

"IBM creates highest performing nanotube transistors", IBM News, 2002.

Javey, A., Ballistic Carbon Nanotube Field-Effect Transistors, *Nature*, 424:654-657 (2003) [S:].

Jin, "Scalable Interconnection and Integration of Nanowire Devices without Registration," *Nano-Lett*, 4(5):915-919 (2004).

Johnson, J.C., et al., "Single gallium nitride nanowire lasers," *Nature Materials*, 1, (2002), pp. 106-110.

Johnson, J.C., et al., "Single Nanowire Lasers," *J. Phys. Chem.*, 105(46), (2001), pp. 11387-11390.

Joselevich, E., et al., "Vectorial Growth of Metallic and Semiconducting Single-Wall Carbon Nanotubes," *Nano Letters*, 2(10), (2002), pp. 1137-1141.

Kanjanachuchai et al., "Coulomb blockade in strained-Si nanowires on leaky virtual substrates", *Semiconductor Science and Technology*, 2001, vol. 16, pp. 72-76.

Kong et al. "Nanotube molecular wires as chemical sensors", *Science*, Jan. 28, 2000, vol. 287, pp. 622-625.

Kong, J., et al., "Chemical vapor deposition of methane for single-walled carbon nanotubes," *Chem. Physics Letters*, 292, (1998), pp: 567-574.

Kong, J., et al., "Synthesis of individual single-walled carbon natubes on patterned silicon wafers," *Nature*, 395, (1998), pp: 878-881.

Lahoun et al., "Epitaxial core-shell and core-multishell nanowire heterostructures", *Nature*, 2002, vol. 420, pp. 57-61.

Lahoun, L.J. et al., "Semiconductor nanowire heterostructures," 2004, *Phil. Trans. R. Soc. Lond.*, 362: 1247-1260 (2004).

Law, "Nanoribbon Waveguides for Subwavelength Photonics Integration," *Science*, 305(27): 1269-1273 (2004).

Leff, "Thermodynamic Control of Gold Nanocrystal Size: Experiment and Theory,"*J Phys Chem*, 99:7036-7041 (1995).

Lei, "Nanowire transistors with ferroelectric gate dielectrics: Enhanced performance and memory effects," *Apl Phys Lett*, 84(22):4553-4555 (2004).

Lieber, "Nanoscale Science and Technology: Building a Big Future from Small Things," *MRS Bull*, www.mrs.org/publications/bulletin (2003).

Lieber, "Nanowire Superlattices," *Nanoletters*, 2(2): 81-82 (2002).

Lu, W. et al., "One-dimensional hole gas in germanium/silicon nanowire heterostructures," *PNAS*, 102: 10046-10051(2005).

Martel, R., et al., "Single- and multi-wall carbon nanotube field-effect transistors," *Apl Phys Lett*, 73(17), (1998), pp. 2447-2449.

McAlpine, "High-Performance Nanowire Electronics and Photonics and Nanoscale Patterning on Flexible Plastic Substrates," *Proc IEEE*, 93(7): 1357-1363 (2005).

McAlpine, M. "High-Performance Nanowire Electronics and Photonics on Glass and Plastic Substrates", *Nano Letters*, 3(11): 1531-1535 (2003).

McAlpine, M., "Nanoimprint Lithography for Hybrid Plastic Electronics", *Nano-Letters*, 3(4): 443-445 (2003).

Menon, "Fabrication and Evaluation of Nanoelectrode Ensembles," *Anal Chem*, 67(13): 1920-1928 (1995).

Mizutani, T., "Fabrication and Characterization of Carbon Nanotube FETs," Quantum Sensing and Nanophotonic Devices II, M. Flazeghi, G.J. Brown, Ed., Proc SPIE, vol. 5732, p. 28-36.

Morales, et al., "A Laser Ablation Method for the Synthesis of Crystalline Semiconductor Nanowires" *Science*, 279:208-211 (1998).

Musin, R. N., "Structural and Electronic Properties of Epitaxial Core-Shell Nanowire Heterostructures," *Phys. Rev. B*,71:155318.

Nosho, Y., "n-type Carbon Nanotube Field-Effect Transistors Fabricated by Using Ca Contact Electrodes," *Appl. Phys. Lett.*, 86:73105.
Padeste, et al., "Modular amperometric immunosensor devices", 1995, *8th International Conference on Solid-State Sensors an Actuators and Eurosensors IX*, 357(C7): 487-490 (1995).
Patolsky, "Electrical detection of single viruses," *PNAS*, 101(3 9 ):14017-14022 (2004).
Patolsky, "Nanowire nanosensors," *Mat Today*, 1369(7021): 20-28 (2005).
Pavesi, "Optical gain in silicon nanocrystals," *Nature*, 408:440-444 (2000).
Qi, "Toward Large Arrays of Multiplex Functionalized Carbon Nanotube Sensors for Highly Sensitive and Selective Molecular Detection," *Nano-Lett*, 3(3) :347-351 (2003).
Rueckes, T., et al., "Carbon Nanotube-Based Nonvolatile Random Access Memory for Molecular Computing," *Science*, 298, (2000), pp. 94-97.
Star et al., "Preparation and properties of polymer-wrapped single-walled carbon nanotubes", *Angew. Chem. Int.*, 2001, vol. 40, No. 9, pp. 1721-1725.
Takayama, S., et al., "Patterning cells and their environments using multiple laminar fluid flows in capillary networks", *Proc. Natl. Acad. Sci.*, 96: 5545-5548 (1999).
Tans, et al., "Room-temperature transistor based on a single carbon nanotube", *Nature*, 393: 49-52 (1998).
Thess, a., et al., "Cyrstalline Ropes of Metallic Carbon Nanotubes," *Science*, 273, (1996), pp. 483-487.
Tiefenauer, et al., "Towards Amperometric Immunosensor Devices" *Biosensors and Bioelectronics*, 12(3): 213-223 (1997).
Tong, "Subwavelength-diameter silica wires for low-loss optical wave guiding," *Nature*, 426(18):816-819 (2003).
Urban, "Single-Crystalling Barium Titanate Nanowires," *Adv Mat*, 15(5):423-426 (2003).
Vossmeyer, T. et al., "Combinatorial approaches toward patterning nanocrystals," Journal of Applied Physics, 1998, 84(7):3664-3670.
Wang et al., "Highly polarized photoluminescence and photodetection from single indium phosphide nanowires", *Science*, 2001, vol. 293, pp. 1455-1457.
Wang, "Label-free detection of small-molecule-protein interactions by using nanowire nanosensors," *PNAS*, 102(9):3208-3212 (2005).
Wang, N., et al., "$SiO_2$-enhanced synthesis of Si nanowires by laser ablation," *App. Physics Letters*, 73(26), (1998), pp. 3902-3904.
Wei, Q., et al., "Synthesis of Single Crystal Bismuth-Telluride and Lead-Telluride Nanowires for New Thermoelectric Materials," *Mat. Res. Soc. Symp. Proc.*, 581, (2000), pp. 219-223.
Whang, "Large-Scale Hierarchical Organization of Nanowire Arrays for Integrated Nanosystems," *Nano-Lett*, 3(9):1255-1259 (2003).
Whang, "Nanolithographys Using Hierarchically Assembled Nanowire Masks," *Nano-Lett*, 3(7):951-954 (2003).
Wolf, et al., "Silicon Processing for the VLSI ERA", *Lattice Press*, 1:12-13 (2000).
Wong, S., et al., "Covalently funtionalized nanotubes as nanometre-sized probes in chemistry and biology," *Nature*, 394, (1998), pp: 52-55.
Wu et al., "Block-by-block growth of single-crystalline Si/SiGe superlattice nanowires", web release date, Jan. 19, 2002, http://pubs.acs.org/hotartcl/nalefd/2002/n10156888_rev.html.
Wu, "Controlled Growth and Structures of Molecular-Scale Silicon Nanowires," *Nano-Lett*, 4(3):433-436 (2004).
Wu, "Single-crystal metallic nanowires and metal/semiconductor nanowire heterostructures," *Nature*, 430:61-65 (2004).
Xiang, "Ge/Si nanowire heterostructures as high-performance field-effect transistors," *Nature*, 441:489-493 (2006).
Yamada, Y., "Analysis of submicron carbon nanotube field-effect transistors", *Appl Phys Lett*, 76: (5): 628-630 (2000).
Yang, "Wires on water," *Nature*, 425:243-244 (2003).
Yang, P. et al., "Controlled Growth of ZnO Nanowires and Their Optical Properties," *Adv. Funct. Matter*, 12(5), (2002), pp. 323-331.
Yu, et al., "Nanoscale silicon wires synthesized using simple physical evaporation", *Appl Phys Lett*, 72 (26): 3458-3460 (1998).
Yun, W.S., et al., "Ferroelectric Properties of Individual Barium Titanate Nanowires Investigated by Scanned Probe microscopy," *Nano Letters*, vol. 2, No. 5, p. 447-450 (2002).
Zheng, "Multiplexed electrical detection of cancer markers with nanowire sensor arrays," *Nature Biotech*, 23(10): 1294-1301 (2005).
Zheng, "Synthesis and Fabrication of High-Performance n-Type Silicon Nanowire Transistors," *Adv Matt*, 16(20):1890-1893 (2004).
Zhong, "Coherent Single Charge Transport in Molecular-Scale Silicon Nanowires," *Nano-Lett*, 5(6):1143-1146 (2005).
Zhong, "Nanowire Crossbar Arrays as Address Decoders for Integrated Nanosystems," *Science*, 302:1377-1379 (2003).
Zhong, "Synthesis of p-Type Gallium Nitride Nanowires for Electronic and Photonic Nanodevices," *Nano-Lett*, 3(3):343-346 (2003).
Zhou, G., et al., "Growth morphology and micro-structural aspects of Si nanowires synthesized by laser ablation," *J. of Crystal Growth*, 197, (1999), pp: 129-135.
International Preliminary Exam. Report from Int. Apl. No. PCT/US01/48230, filed Dec. 11, 2001.
International Preliminary Exam. Report from Int. Apl. No. PCT/US2005/020974, filed Jun. 15, 2005.
International Search Report from Int. Apl. No. PCT/US01/48230, filed Dec. 11, 2001.
International Search Report from Int. Apl. No. PCT/US02/16133, field May 20, 2002.
International Search Report from Int. Apl. No. PCT/US03/22061, filed Jul. 16, 2003.
International Search Report from Int. Apl. No. PCT/US03/22753, filed Jul. 21, 2003.
International Search Report from Int. Apl. No. PCT/US2005/004459, filed Feb. 14, 2005.
International Search Report from Int. Apl. No. PCT/US2005/020974, filed Jun. 15, 2005.
International Search Report from Int. Apl. No. PCT/US2005/026759, filed Jul. 28, 2005.
International Search Report from Int. Apl. No. PCT/US2005/034345, filed Nov. 21, 2005.
Invitation to Pay Addition Fees from Int. Apl. No. PCT/US2005/044212, filed Dec. 6, 2005.
Office Action mailed Jan. 03, 2005 in U.S. Appl. No. 10/196,337, filed Jul. 16, 2002.
Office Action mailed Jan. 15, 2003 in U.S. Appl. No. 10/020,004, filed Dec. 11, 2001.
Office Action mailed Feb. 23, 2006 in U.S. Appl. No. 10/196,337, filed Jul. 16, 2002.
Office Action mailed Mar. 11, 2005 in U.S. Appl. No. 09/935,776, filed Aug. 22, 2001.
Office Action mailed Mar. 14, 2005 in U.S. Appl. No. 10/020,004, filed Dec. 11, 2001.
Office Action mailed Apr. 07, 2006 in U.S. Appl. No. 10/734,086, filed Dec. 11, 2003.
Office Action mailed Apr. 23, 2007 in U.S. Appl. No. 11/582,167, filed Oct. 17, 2006.
Office Action mailed May 16, 2006 in U.S. Appl. No. 09/935,776, filed Aug. 22, 2001.
Office Action mailed May 25, 2005 in U.S. Appl. No. 10/196,337, filed Jul. 16, 2002.
Office Action mailed Jun. 25, 2004 in U.S. Appl. No. 10/020,004, filed Dec. 11, 2001.
Office Action mailed Jun. 30, 2004 in U.S. Appl. No. 10/196,337, filed Jul. 16, 2002.
Office Action mailed Aug. 30, 2005 in U.S. Appl. No. 09/935,776, filed Aug. 22, 2001.
Office Action mailed Aug. 30, 2005 in U.S. Appl. No. 10/020,004, filed Dec. 11, 2001.
Office Action mailed Sep. 2, 2003 in U.S. Appl. No. 09/935,776, filed Aug. 22, 2001.
Office Action mailed Sep. 15, 2004 in U.S. Appl. No. 09/935,776, filed Aug. 22, 2001.
Office Action mailed Oct. 27, 2006 in U.S. Appl. No. 10/734,086, filed Dec. 11, 2003.
Office Action mailed Nov. 2, 2006 in U.S. Appl. No. 10/196,337, filed Jul. 16, 2002.
Office Action mailed Nov. 29, 2005 in U.S. Appl. No. 10/995,075, filed Nov. 22, 2004.
Office Action mailed Dec. 20, 2006 in U.S. Appl. No. 11/012,549, filed Dec. 15, 2004.

Written Opinion from Int. Apl. No. PCT/US01/48230, filed Dec. 11, 2001.
Written Opinion from Int. Apl. No. PCT/US2005/004459, filed Feb. 14, 2005.
Written Opinion from Int. Apl. No. PCT/US2005/020974, filed Jun. 15, 2005.
Written Opinion from Int. Apl. No. PCT/US2005/026759, filed Jul. 28, 2005.
Written Opinion from Int. Apl. No. PCT/US2005/034345, filed Nov. 21, 2005.
Balavoine, F. et al., "Helical Crystalization of Proteins on Carbon Nanotubes: A First Step towards the Development of New Biosensors," *Angew. Chem. Int. Ed.*, vol. 38, No. 13/14, pp. 1912-1915 (1999).
Fagan, S. et al. "*Ab initio* calculations for a hypothetical material: Silicon nanotubes," *Physical Review B*, vol. 61, No. 15, pp. 9994-9996 (2000).
Jensen, K. et al. "Kinetics for Hybridization of Peptide Nucleic Acids (PNA) with DNA and RNA Studied with the BIAcore Technique," *Biochemistry*, vol. 36, pp. 5072-5077 (1997).
Li, C.Z. et al., "Fabrication of stable metallic nanowires with quantized conductance," *Nanotechnology*, vol. 10, pp. 221-223 (1999).
Li, Z. et al., "Sequence-Specific Label-Free DNA Sensors Based on Silicon Nanowires," *Nano Letters*, vol. 4, No. 2, pp. 245-247 (2004).
Patolsky, F. et al., "Nanowire sensors for medicine and the life sciences,"*Nanomedicine*, vol. 1, No. 1, pp. 51-65 (2006).
Soh, H. et al., "Integrated nanotube circuits: Controlled growth and ohmic contacting of single-walled carbon nanotubes," *Appl. Phys. Lett.*, vol. 75, No. 5, pp. 627-629 (1999).
Tang,Y.H. et al., "Si nanowires synthesized by laser ablation of mixed SiC and Si02 powders," *Chemical Physics Letters*, vol. 314, pp. 16-20 (1999).
Office Action mailed Aug. 7, 2006 in U.S. Appl. No. 11/082,372, filed Mar. 17, 2005.
Office Action mailed Mar. 18, 2008 in U.S. Appl. No. 11/543,337, filed Oct. 4, 2006.
International Search Report and Written Opinion from Int. Apl. No. PCT/US2007/008540, filed Jun. 4, 2007.
Office Action from U.S. Appl. No. 11/543,352, dated Sep. 12, 2008.
Office Action from U.S. Appl. No. 11/543,746, dated Sep. 8, 2008.
Office Action from U.S. Appl. No. 11/543,336, dated Jun. 18, 2008.
Office Action from U.S. Appl. No. 11/543,353, dated Oct. 6, 2008.
Office Action from U.S. Appl. No. 12/038,794, dated Mar. 6, 2009.
Office Action from U.S. Appl. No. 11/172,408, dated Dec. 29, 2008.
Office Action from U.S. Appl. No. 11/501,466, dated Feb. 5, 2009.
International Search Report and Written Opinion from PCT Application PCT/US2007/013700 dated May 29, 2008.
International Search Report and Written Opinion from PCT Application PCT/US2007/019669 dated Jan. 24, 2008.
International Search Report and Written Opinion from PCT Application PCT/US2007/024222 dated Oct. 10, 2008.
International Search Report and Written Opinion from PCT Application PCT/US2007/024126 dated Sep. 26, 2008.
MacBeath, et al., "Printing Proteins as Microarrays for High-Throughput Function Determination," Science, vol. 289, Sep. 8, 2000, pp. 1760-1763.
Mitchell, et al., "Smart Nanotubes for Bioseparations and Biocatalysis," JACS Communications, 124, 2002, pp. 11864-11865.
Neuman et al., "Microarray profiling of antiviral antibodies for the development of diagnostics, vaccines, and therapeutics," Clinical Immunology, 111 (2004) pp. 196-201.
Patolsky, Fernando et al. "Nanowire-Based Biosensors" Analytical Chemistry, Jul. 1, 2006, pp. 4261-4269.
Shi, Y. et al. "Long Si Nanowires With Millimeter-Scale Length by Modified Thermal Evaporation From Si Powder" Appl. Phys. A 80, 1733-1736 (2005).
Smalley, "Biochip spots single viruses," The Latest Technology Research News, Oct. 20, 2004, (4 pages).
Zhang, Y.F. et al. "Bulk-Quantity Si Nanowires Synthesized by SiO Sublimation" Journal of Crystal Growth, 212 (2000) pp. 115-118.
Wang, D. et al. "Rational Growth of Branched and Hyperbranched Nanowire Structures" Nano Letters, 2004, vol. 4, No. 5, pp. 871-874.
Wu, et al., Germanium/carbon core-sheath nanostructures, Applied Physics Letters, vol. 77, No. 1, Jul. 3, 2000, pgs. 43-45.
Yu, J. et al. "One-Dimensional Silicon Nanostructures Fabricated by Thermal Evaporation" Materials Science & Engineering C26 (2006), pp. 800-804.

\* cited by examiner

First layer

Second layer

Forward bias

Reverse bias

DOPED ELONGATED SEMICONDUCTORS, GROWING SUCH SEMICONDUCTORS, DEVICES INCLUDING SUCH SEMICONDUCTORS, AND FABRICATING SUCH DEVICES

RELATED APPLICATIONS

This application is a continuation of U.S. patent application Ser. No. 09/935,776, entitled "Doped Elongated Semiconductors, Growing Such Semiconductors, Devices Including Such Semiconductors And Fabricating Such Devices, filed Aug. 22, 2001; which claims priority under 35 U.S.C. §119(e) to commonly-owned, co-pending U.S. Provisional Patent Application Ser. No. 60/226,835, entitled, "Semiconductor Nanowires", filed Aug. 22, 2000; Ser. No. 60/292,121, entitled, "Semiconductor Nanowires", filed May 18, 2001; Ser. No. 60/254,745, entitled, "Nanowire and Nanotube Nanosensors," filed Dec. 11, 2000; Ser. No. 60/292,035, entitled "Nanowire and Nanotube Nanosensors," filed May 18, 2001; Ser. No. 60/292,045, entitled "Nanowire Electronic Devices Including Memory and Switching Devices," filed May 18, 2001; and Ser. No. 60/291,896, entitled "Nanowire Devices Including Emissive Elements and Sensors," filed May 18, 2001, each of which is hereby incorporated by reference in its entirety.

FEDERALLY SPONSORED RESEARCH

This invention was made with government support under N00014-00-1-0476, N00014-99-1-0495, N00014-98-1-0499, and N00014-94-1-0302 awarded by the Office of Naval Research and DBI-98346603 awarded by the National Science Foundation. The government has certain rights in the invention.

BACKGROUND

Small-scale electronic technology relies to a large extent on doping of various materials. Doping of semiconductor materials to form n-type and p-type semiconductor regions for making a variety of devices such as field effect transistors, bipolar transistors, complementary inverters, tunnel diodes, and the like are well known.

Typical state-of-the-art semiconductor fabrication facilities involve relatively high cost, and require a clean room and the use of toxic chemicals such as hydrogen fluoride. While semiconductor and microfabrication technology is well-developed, there is a continuing need for improvements, preferably including smaller-scale, environmentally-friendly fabrication, at lower cost.

SUMMARY

In an embodiment, provided is a free-standing bulk-doped semiconductor comprising at least one portion having a smallest width of less than 500 nanometers.

In another aspect of this embodiment, the semiconductor comprises: an interior core comprising a first semiconductor; and an exterior shell comprising a different material than the first semiconductor.

In another aspect of this embodiment, the semiconductor is elongated. In various optional features of this aspect, at any point along a longitudinal section of the semiconductor, a ratio of the length of the section to a longest width is greater than 4:1, or greater than 10:1, or greater than 100:1, or even greater than 1000:1.

In various aspects of this embodiment, at least one portion of the semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the semiconductor comprises a semiconductor from a group consisting of: Si, Ge, Sn, Se, Te, B, Diamond, P, B—C, B—P ($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$, and an appropriate two or more such semiconductors.

In various aspects of this embodiment, the semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type selected from a group consisting of: Si, Ge, Sn, S, Se and Te.

In another aspect of this embodiment, the semiconductor is part of a device. In another aspect of this embodiment, the semiconductor is n-doped. In various optional features of this aspect, the semiconductor is either lightly n-doped or heavily n-doped.

In yet another aspect of this embodiment, the semiconductor is p-doped. In various optional features embodiments of this aspect, the semiconductor is either lightly p-doped or heavily p-doped.

In another aspect of this embodiment, the semiconductor is a single crystal.

In additional various aspects of this embodiment, the semiconductor is magnetic; the semiconductor comprises a dopant making the semiconductor magnetic the semiconductor is ferromagnetic; the semiconductor comprises a dopant that makes the semiconductor ferromagnetic; and/or the semiconductor comprises manganese.

In another embodiment, provided is an elongated and bulk-doped semiconductor that, at any point along its longitudinal axis, has a largest cross-sectional dimension less than 500 nanometers.

In an aspect of this embodiment, the semiconductor is free-standing.

In another aspect of this embodiment, the semiconductor comprises: an interior core comprising a first semiconductor; and an exterior shell comprising a different material than the first semiconductor.

In various aspects of this embodiment, at any point along the longitudinal axis of the semiconductor, a ratio of the length of the section to a longest width is greater than 4:1, or greater than 10:1, or greater than 100:1 or even greater than 1000:1.

In various aspects of this embodiment, at least one longitudinal section of the semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, at least one longitudinal section of the semiconductor has a largest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the semiconductor comprises a semiconductor from a group consisting of: Si, Ge, Sn, Se, Te, B, Diamond, P, B—C, B—P ($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$, and an appropriate combination of two or more such semiconductors.

In various aspects of this embodiment, the semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type dopant selected from a group consisting of: Si, Ge, Sn, S, Se and Te.

In another aspect of this embodiment, the semiconductor is part of a device.

In another aspect of this embodiment, the semiconductor is n-doped. In various optional features of this aspect, the semiconductor is either lightly n-doped or heavily n-doped.

In yet another aspect of this embodiment, the semiconductor is p-doped. In various optional features embodiments of this aspect, the semiconductor is either lightly p-doped or heavily p-doped.

In another aspect of this embodiment, the semiconductor is a single crystal.

In another embodiment, provided is a doped semiconductor comprising a single crystal.

In an aspect of this embodiment, the semiconductor is bulk-doped.

In an aspect of this embodiment, the semiconductor is elongated. In various optional features of this aspect, at any point along a longitudinal section of the semiconductor, a ratio of the length of the section to a longest width is greater than 4:1, or greater than 10:1, or greater than 100:1, or even greater than 1000:1.

In various aspects of this embodiment, at least one portion of the semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the semiconductor comprises a semiconductor from a group consisting of: Si, Ge, Sn, Se, Te, B, Diamond, P, B—C, B—P ($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$, and an appropriate combination of two or more such semiconductors.

In various aspects of this embodiment, the semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type dopant selected from a group consisting of: Si, Ge, Sn, S, Se and Te.

In yet another embodiment, provided is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, where a phenomena produced by a section of the bulk-doped semiconductor exhibits a quantum confinement caused by a dimension of the section.

In another aspect of this embodiment, the longitudinal section is capable of emitting light in response to excitation, wherein a wavelength of the emitted light is related to the width. In optional features of this aspect: the wavelength of the emitted light is a function of the width; the longitudinal section is capable of transporting electrical carriers without scattering; the longitudinal section is capable of transporting electrical carriers such that the electrical carriers pass through the longitudinal section ballistically; the longitudinal section is capable of transporting electrical carriers such that the electrical carriers pass through the longitudinal section coherently; the longitudinal section is capable of transporting electrical carriers such that the electrical carriers are spin-polarized; and/or the longitudinal section is capable of transporting electrical carriers such that the spin-polarized electrical carriers pass through the longitudinal section without losing spin information.

In another embodiment, provided is a solution comprising one or more doped semiconductors, wherein at least one of the semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In an aspect of this embodiment, the at least one semiconductor is elongated. In various optional features of this aspect, at any point along a longitudinal section of the semiconductor, a ratio of the length of the section to a longest width is greater than 4:1, or greater than 10:1, or greater than 100:1 or even greater than 1000:1.

In various aspects of this embodiment, at least one portion of the at least one semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the at least one semiconductor comprises a semiconductor from a group consisting of: Si, Ge, Sn, Se, Te, B, Diamond, P, B—C, B—P (BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO, and an appropriate combination of two or more such semiconductors.

In various aspects of this embodiment, the at least one semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type selected from a group consisting of: Si, Ge, Sn, S, Se and Te.

In another embodiment, provided is a device comprising one or more doped semiconductors, wherein at least one of the semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In an aspect of this embodiment, the device comprises at least two doped semiconductors, wherein both of the at least two doped semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein a first of the at least two doped semiconductors exhibits quantum confinement and a second of the at least two doped semiconductor manipulates the quantum confinement of the first.

In another aspect of this embodiment, the device comprises at least two doped semiconductor, wherein both of the at least two doped semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers. In various optional features of this embodiment: the at least two bulk-doped semiconductors are in physical contact with each other; a first of the at least two bulk-doped semiconductors is of a first conductivity type, and a second of the at least two bulk-doped semiconductors is of a second conductivity type; the first conductivity type is n-type, and the second type of conductivity type is p-type; and/or the at least two bulk-doped semiconductors form a p-n junction.

In various aspects of this embodiment, the device comprises one or more of the following: a switch; a diode; a Light-Emitting Diode; a tunnel diode; a Schottky diode; a Bipolar Junction Transistor; a Field Effect Transistor; an inverter; a complimentary inverter; an optical sensor; a sensor for an analyte (e.g., DNA); a memory device; a dynamic memory device; a static memory device; a laser; a logic gate; an AND gate; a NAND gate; an EXCLUSIVE-AND gate; an OR gate; a NOR gate; an EXCLUSIVE-OR gate; a latch; a register; clock circuitry; a logic array; a state machine; a programmable circuit; an amplifier; a transformer; a signal processor; a digital circuit; an analog circuit; a light emission source; a photoluminescent device; an electroluminescent device; a rectifier; a photodiode; a p-n solar cell.; a phototransistor; a single-electron transistor; a single-photon emitter; a single-photon detector; a spintronic device; an ultra-sharp tip for atomic force microscope; a scanning tunneling microscope; a field-emission device; a photoluminescence tag; a photovoltaic device; a photonic band gap materials; a scanning near field optical microscope tips; and a circuit that has digital and analog components.

In various aspects of this embodiment, for a device that includes one or more of the device components listed in the previous paragraph, one of the device components may include the at least one semiconductor. In an optional feature of this aspect, a plurality of the components of the device may include at least one semiconductor, where, for each device component, the at least one semiconductor is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In an aspect of this embodiment, the at least one semiconductor is elongated. In various optional features of this aspect, at any point along a longitudinal section of the semiconductor, a ratio of the length of the section to a longest width is greater than 4:1, or greater than 10:1, or greater than 100:1 or even greater than 1000:1.

In various aspects of this embodiment, at least one portion of the at least one semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the at least one semiconductor comprises a semiconductor from a group consisting of: Si, Ge, Sn, Se, Te, B, Diamond, P, B—C, B—P (BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCi, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO, and an appropriate combination of two or more such semiconductors.

In various aspects of this embodiment, the at least one semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type selected from a group consisting of: Si, Ge, Sn, S, Se and Te.

In another aspect of this embodiment, the device comprises another semiconductor that is electrically coupled to the at least one bulk-doped semiconductor.

In another aspect of this embodiment, the device comprises another semiconductor that is optically coupled to the at least one bulk-doped semiconductor. In yet another aspect of this embodiment, the device comprises another semiconductor that is magnetically coupled to the at least one bulk-doped semiconductor.

In another aspect of this embodiment, the device comprises another semiconductor that physically contacts the at least one bulk-doped semiconductor.

In various aspects of this embodiment, the at least one semiconductor is coupled to one or more of: an electrical contact; an optical contact; or a magnetic contact.

In another aspect of this embodiment, a conductivity of the at least one semiconductor is controllable in response to a signal. In various optional features of this aspect: the conductivity of the at least one semiconductor is controllable to have any value within a range of values; the at least one semiconductor is switchable between two or more states; the at least one semiconductor is switchable between a conducting state and an insulating state by the signal; two or more states of the at least one semiconductor are maintainable without an applied signal; the conductivity of the at least one semiconductor is controllable in response to an electrical signal; the conductivity of the at least one semiconductor is controllable in response to an optical signal; the conductivity of the at least one semiconductor is controllable in response to a magnetic signal; and/or the conductivity of the at least one semiconductor is controllable in response to a signal of a gate terminal.

In another aspect of this embodiment, at least two of the semiconductors are arranged in an array, and at least one of the semiconductors arranged in the array is a bulk-doped semiconductor comprising at least one portion having a smallest width of less than 500 nanometers. In an optional feature of this aspect, the array is an ordered array. In another optional feature of this embodiment, the array is not an ordered array.

In yet another aspect of this embodiment, the device comprises two or more separate and interconnected circuits, at least one of the circuits not comprising a bulk-doped semiconductor that comprises at least one portion having a smallest width of less than 500 nanometers.

In another aspect of this embodiment, the device is embodied on a chip having one or more pinouts. In an optional feature of this embodiment, the chip comprises separate and interconnected circuits, at least one of the circuits not comprising a bulk-doped semiconductor that comprises at least one portion having a smallest width of less than 500 nanometers.

In another embodiment, provided is a collection of reagents for growing a bulk-doped semiconductor that comprises at least one portion having a smallest width of less than 500 nanometers, the collection comprising a semiconductor reagent and a dopant reagent.

In an aspect of this embodiment, the at least one semiconductor is elongated. In various optional features of this aspect, at any point along a longitudinal section of the semiconductor, a ratio of the length of the section to a longest width is greater than 4:1, or greater than 10:1, or greater than 100:1 or even greater than 1000:1.

In various aspects of this embodiment, at least one portion of the at least one semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the at least one semiconductor comprises a semiconductor from a group consisting of: Si, Ge, Sn, Se, Te, B, Diamond, P, B—C, B—P ($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCi, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, $(Cu, Ag)(Al, Ga, In, Tl, Fe)(S, Se, Te)_2$, $Si_3N_4$, $Ge_3N_4$, $Al_2O_3$, $(Al, Ga, In)_2(S, Se, Te)_3$, $Al_2CO$, and an appropriate combination of two or more such semiconductors.

In various aspects of this embodiment, the at least one semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type selected from a group consisting of: Si, Ge, Sn, S, Se and Te.

In another embodiment, a semiconductor is doped during growth of the semiconductor.

In various aspects of this embodiment: the semiconductor is free-standing; the semiconductor has a smallest width of no more than 100 nanometers; an extent of the doping is controlled; the doped semiconductor is grown by applying energy to a collection of molecules, the collection of molecules comprising molecules of the semiconductor and molecules of a dopant; an extent of the doping is controlled; a ratio of an amount of the semiconductor molecules to an amount of the dopant molecules is controlled; the molecules are vaporized using a laser to form vaporized molecules; the semiconductor is grown from the vaporized molecules; the vaporized molecules are condensed into a liquid cluster; the semiconductor is grown from the liquid cluster; growing the semiconductor is performed using laser-assisted catalytic growth; the collection of molecules comprises a cluster of molecules of a catalyst material; a width of the semiconductor is controlled; and/or the width of the semiconductor is controlled by controlling a width of the catalyst cluster.

In additional aspects of this embodiment: the act of doping includes performing chemical vapor deposition on at least the molecules; the grown semiconductor has at least one portion having a smallest width of less than 20 nanometers; the grown semiconductor has at least one portion having a smallest width of less than 10 nanometers; and/or the grown semiconductor has at least one portion having a smallest width of less than 5 nanometers.

In yet other additional aspects of this embodiment: the grown semiconductor is magnetic; the semiconductor is doped with a material that makes the grown semiconductor magnetic; the grown semiconductor is ferromagnetic; the semiconductor is doped with a material that makes the grown semiconductor ferromagnetic; the semiconductor is doped with manganese.

In another aspect of this embodiment, the at least one semiconductor is elongated. In various optional features of this aspect, at any point along a longitudinal section of the semiconductor, a ratio of the length of the section to a longest width is greater than 4:1, or greater than 10:1, or greater than 100:1 or even greater than 1000:1.

In various aspects of this embodiment, at least one portion of the at least one semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the at least one semiconductor comprises a semiconductor from a group consisting of: Si, Ge, Sn, Se, Te, B, Diamond, P, B—C, B—P ($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, $(Cu, Ag)(Al, Ga, In, Tl, Fe)(S, Se, Te)_2$, $Si_3N_4$, $Ge_3N_4$, $Al_2O_3$, $(Al, Ga, In)_2(S, Se, Te)_3$, $Al_2CO$, and an appropriate combination of two or more such semiconductors.

In various aspects of this embodiment, the at least one semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type selected from a group consisting of: Si, Ge, Sn, S, Se and Te.

In another embodiment; a device is fabricated. One or more semiconductors are contacted to a surface, where at least one of the semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers. In various aspects of this embodiment: the surface is a substrate; prior to contacting the surface, at least one of the semiconductors is grown by applying energy to molecules of a semiconductor and molecules of a dopant; a solution is contacted comprising the one or more semiconductors to the surface; one or more of the semiconductors are aligned on the surface using an electric field; an electric field is generated between at least two electrodes and one or more of the semiconductors are positioned between the electrodes; another solution comprising one or more other semiconductors is contacted to the surface, where at least one of the other semiconductor is a bulk-doped semiconductor comprising at least one portion having a smallest width of less than 500 nanometers; the surface is conditioned to attach the one or more contacted semiconductors to the surface; forming channels on the surface; patterns are formed on the surface; one or more of the semiconductors are aligned on the surface using an electric field; the at least one semiconductor is elongated.

In various optional features of this aspect, at any point along a longitudinal section of the semiconductor, a ratio of the length of the section to a longest width is greater than 4:1, or greater than 10:1, or greater than 100:1 or even greater than 1000:1.

In various aspects of this embodiment, at least one portion of the at least one semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the at least one semiconductor comprises a semiconductor from a group consisting of: Si, Ge, Sn, Se, Te, B, Diamond, P, B—C, B—P ($BP_6$), B—Si, Si—C, Si—Ge, Si—Sn and Ge—Sn, SIC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, $(Cu, Ag)(Al, Ga, In, Tl, Fe)(S, Se, Te)_2$, $Si_3N_4$, $Ge_3N_4$, $Al_2O_3$, $(Al, Ga, In)_2(S, Se, Te)_3$, $Al_2CO$, and an appropriate combination of two or more such semiconductors.

In various aspects of this embodiment, the at least one semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type selected from a group consisting of: Si, Ge, Sn, S, Se and Te.

In another embodiment, generating light is generated by applying energy to one or more semiconductors causing the one or more semiconductors to emit light, wherein at least one of the semiconductors is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In an aspect of this embodiment, the at least one semiconductor is elongated. In various optional features of this aspect, at any point along a longitudinal section of the semiconductor, a ratio of the length of the section to a longest width is greater than 4:1, or greater than 10:1, or greater than 100:1 or even greater than 1000:1.

In various aspects of this embodiment, at least one portion of the at least one semiconductor has a smallest width of less than 200 nanometers, or less than 150 nanometers, or less than 100 nanometers, or less than 80 nanometers, or less than 70 nanometers, or less than 60 nanometers, or less than 40 nanometers, or less than 20 nanometers, or less than 10 nanometers, or even less than 5 nanometers.

In various aspects of this embodiment, the at least one semiconductor comprises a semiconductor from a group consisting of: Si, Ge, Sn, Se, Te, B, Diamond, P, B—C, B—P ($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$, and an appropriate combination of two or more such semiconductors.

In various aspects of this embodiment, the at least one semiconductor comprises a dopant from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; or an n-type selected from a group consisting of: Si, Ge, Sn, S, Se and Te.

In various aspects of this embodiment: the at least one semiconductor is a bulk-doped; the semiconductor comprises a direct-band-gap semiconductor; a voltage is applied across a junction of two crossed semiconductors, each semiconductor having a smallest width of less than 500 nanometers; each semiconductor has a smallest width of less than 100 nanometers; a wavelength of the emitted light is controlled by controlling a dimension of the at least one semiconductor having a smallest width of less than 100 nanometers; the semiconductor is elongated, and a width of the elongated semiconductor is controlled; the semiconductor has a property that a mass of the semiconductor emits light at a first wavelength if the mass has a minimum shortest dimension, and the controlled dimension of the semiconductor is less than the minimum shortest dimension.

In another embodiment, a device having at least a doped semiconductor component and one or more other components is fabricated. A semiconductor is doped during its growth to produce the doped semiconductor component, and the doped semiconductor component is attached to at least one of the one or more other components.

In an aspect of this embodiment, the doped semiconductor is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers.

In various aspects of this embodiment: the semiconductor component is at least part of a nanowire; the semiconductor is doped during growth of the semiconductor.

In another embodiment provided is a process for controllably assembling a semiconductor device having elongated elements with a characteristic dimension in a transverse direction of the element on a nanometer scale, the process comprising: producing at least one first elements of a first doping type, orienting said first element in a first direction, and connecting said first element to at least one first contact to allow an electrical current to flow through the first element.

In various aspects of this embodiment: the process further comprises producing at least one second elements of a second doping type, orienting said second element in a second direction different from the first direction, enabling an electrical contact between the first element and the second element, and connecting said second element to at least one second contact to allow an electrical current to flow between the first and second element; the process further comprises connecting said first element to spaced-apart contacts and arranging a gate electrode proximate to the first element between the spaced-apart contacts, thereby forming an FET; the first doping type is one of n-type or p-type; the second doping type is n-type if the first doping type is p-type, and p-type if the first doping type is n-type; the first element is oriented by applying at least one of an electric field or a fluid flow; the first element is suspended in the fluid flow; the first element is oriented by applying a mechanical tool; the second element is oriented by applying at least one of an electric field or a fluid flow; the second element is suspended in the fluid flow; the second element is oriented by applying a mechanical tool.

In yet another embodiment, provided is a semiconductor device, comprising: a silicon substrate having an array of metal contacts; a crossbar switch element formed in electrical communication with the array and having a first bar formed of a p-type semiconductor nanowire, and a second bar formed of an n-type semiconductor nanowire and being spaced away from the first bar and being disposed transversely thereto.

In an aspect of this embodiment, the second bar is spaces between 1-10 nm from the first bar.

In another embodiment, provided is a method for manufacturing a nanowire semiconductor device comprising positioning a first nanowire between two contact points by applying a potential between the contact points; and positioning a second nanowire between two other contact points.

In another embodiment, provided is a method for manufacturing a nanowire semiconductor device comprising forming a surface with one or more regions that selectively attract nanowires.

In another embodiment, provided is a method for manufacturing a light-emitting diode from nanowires, the diode having an emission wavelength determined by a dimension of a p-n junction between two doped nanowires.

In yet another embodiment, provided is a method for manufacturing a semiconductor junction by crossing a p-type nanowire and an n-type nanowire.

In another embodiment, provided is a method of assembling one or more elongated structures on a surface, where the method comprising acts of: flowing a fluid that comprises the one or more elongated structures onto the surface; and aligning the one or more elongated structures on the surface to form an array of the elongated structures.

In various embodiments of this method: flowing comprises flowing the fluid in a first direction and aligning comprises aligning the one or more elongated structures as the fluid flows in the first direction to form a first layer of arrayed structures, and the method further comprises changing a direction of the flow from the first direction to a second direction, and repeating the acts of flowing and aligning; at least a first elongated structure from the first layer contacts at least a second elongated structure from the second array; one of the first and second elongated structures is doped semiconductor of a first conductivity type and another of first and second elongated structures is doped semiconductor of a second conductivity type; the first conductivity type is p-type and the second conductivity type is n-type, and wherein the first and second elongated structures form a p-n junction; the surface is a surface of a substrate; the method further comprises transferring the array of elongated structures from the surface of the substrate to a surface of another substrate; transferring comprises stamping; the one or more elongated structured are aligned onto the surface while still comprised in the fluid; conditioning the surface with one or more functionalities that attract the one or more elongated structures to particular positions on the surface, and the act of aligning comprises attracting the one or more elongated structures to the particular positions using the one or more functionalities; the act of conditioning comprises conditioning the surface with one or more molecules; the act of conditioning comprises conditioning the surface with one or more charges; the act of conditioning comprises conditioning the surface with one or more magnetos; the act of conditioning comprises conditioning the surface with one or more light intensities; conditioning the surface with one or more functionalities that attract the one or more elongated structures to particular positions on the surface using chemical force; the act of conditioning comprises conditioning the surface with one or more functionalities that attract the one or more elongated structures to particular positions on the surface using optical force; the act of conditioning comprises conditioning the surface with one or more functionalities that attract the one or more elongated structures to particular positions on the surface using electrostatic force; the act of conditioning comprises conditioning the surface with one or more functionalities that attract the one or more elongated structures to particular positions on the surface using magnetic force; the method further comprises patterning the surface to receive the one or more elongated structures at particular positions on the surface; the act of patterning comprise creating physical patterns on the surface; the physical patterns are trenches; the physical patterns are steps; the surface is a surface of a substrate, and creating physical patterns on the surface comprises using crystal lattice steps of the substrate; the surface is a surface of a substrate, and creating physical patterns on the surface comprises using self-assembled di-block polymer strips; creating physical patterns on the surface comprises using patterns; creating physical patterns on the surface comprises using imprinted patterns; and/or the act of flowing comprises controlling the flow of the fluid using a channel.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P(BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Ti, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In another embodiment, disclosed is a method of assembling one or more elongated structures on a surface, wherein one or more of the elongated structures are at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the method comprises acts of conditioning the surface with one or more functionalities that attract the one or more elongated structures to particular positions on the surface, and aligning the one or more elongated structures by attracting the one or more elongated structures to the particular positions using the one or more functionalities.

In various aspects of this embodiment: the act of conditioning comprises conditioning the surface with one or more molecules; the act of conditioning comprises conditioning the surface with one or more charges; the act of conditioning comprises conditioning the surface with one or more magnetos; the act of conditioning comprises conditioning the surface with one or more light intensities; conditioning the surface with one or more functionalities that attract the one or more elongated structures to particular positions on the surface using chemical force; the act of conditioning comprises conditioning the surface with one or more functionalities that attract the one or more elongated structures to particular positions on the surface using optical force; the act of conditioning comprises conditioning the surface with one or more functionalities that attract the one or more elongated structures to particular positions on the surface using electrostatic force; and/or the act of conditioning comprises conditioning the surface with one or more functionalities that attract the one or more elongated structures to particular positions on the surface using magnetic force.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P(BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In another embodiment, disclosed is a method of assembling a plurality of elongated structures on a surface, wherein one or more of the elongated structures are at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the method comprises acts of: depositing the plurality of elongated structures onto the surface; and electrically charging the surface to produce electrostatic forces between two or more of the plurality of the elongated structures.

In various embodiments of this embodiment: the electrostatic forces cause the two or more elongated structures to align themselves; the electrostatic forces cause the two or more elongated structures to align themselves into one or more patterns; and/or the one or more patterns comprise a parallel array.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P(BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Ti, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In yet another embodiment, provided is a method of assembling a plurality of elongated structures on a surface, wherein one or more of the elongated structures are at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the method comprises acts of: dispersing the one or more elongated structures on a surface of a liquid phase to form a Langmuir-Blodgett film; compressing the Langmuir-Blodgett film; and transferring the compressed Langmuir-Blodgett film onto a surface.

In an aspect of this embodiment: the surface is the surface of a substrate.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P(BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In another embodiment, provided is a method of assembling a plurality of one or more elongated structures on a surface, wherein at least one of the elongated structures are at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the method comprises acts of: dispersing the one or more elongated structures in a flexible matrix; stretching the flexible matrix in a direction to produce a shear force on the one or more elongated structures that causes the at least one elongated structure to align in the direction; removing the flexible matrix; and transferring the at least one aligned elongated structure to a surface.

In various aspects of this embodiment: the direction is parallel to a plane of the surface the act of stretching comprises stretching the flexible matrix with an electrically-induced force; the act of stretching comprises stretching the flexible matrix with an optically-induced force; the act of stretching comprises stretching the flexible matrix with a mechanically-induced force; the act of stretching comprises stretching the flexible matrix with a magnetically-induced force; the surface is a surface of a substrate; the flexible matrix is a polymer.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type dopant selected from a group consisting of: Si, Ge, Sn, S, Se and Te; the doped semiconductor is doped during growth of the semiconductor.

In another embodiment, provided is a system for growing a doped semiconductor, the system comprising: means for providing a molecules of the semiconductor and molecules of a dopant; and means for doping the molecules of the semiconductor with the molecules of the dopant during growth of the semiconductor to produce the doped semiconductor.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type dopant selected from a group consisting of: Si, Ge, Sn, S, Se and Te; the doped semiconductor is doped during growth of the semiconductor.

In another embodiment, provided is a system for assembling one or more elongated structures on a surface, the system comprising: means for flowing a fluid that comprises the one or more elongated structures onto the surface; and means for aligning the one or more elongated structures on the surface to form an array of the elongated structures.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P(BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In yet another embodiment, provided is a system for assembling one or more elongated structures on a surface, wherein one or more of the elongated structures are at least one of the following: is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the system comprises: means for conditioning the surface with one or more functionalities that attract the one or more elongated structures to particular positions on the surface, and means for aligning the one or more elongated structures by attracting the one or more elongated structures to the particular positions using the one or more functionalities.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P(BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In another embodiment, provided is a system for assembling a plurality of elongated structures on a surface, wherein one or more of the elongated structures are at least one of the following: is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the system comprises means for depositing the plurality of elongated structures onto the surface; and means for electrically charging the surface to produce electrostatic forces between two or more of the plurality of the elongated structures.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P(BP$_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BNlBP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, BeSiN$_2$, CaCN$_2$, ZnGeP$_2$, CdSnAs$_2$, ZnSnSb$_2$, CuGeP$_3$, CuSi$_2$P$_3$, (Cu, Ag)(Al, Ga, In, Tl, Fe)(S, Se, Te)$_2$, Si$_3$N$_4$, Ge$_3$N$_4$, Al$_2$O$_3$, (Al, Ga, In)$_2$(S, Se, Te)$_3$, Al$_2$CO; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In another embodiment, provided is a system for assembling a plurality of elongated structures on a surface, wherein one or more of the elongated structures are at least one of the following: is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the system comprises: means for dispersing the one or more elongated structures on a surface of a liquid phase to form a Langmuir-Blodgett film; means for compressing the Langmuir-Blodgett film; and means for transferring the compressed Langmuir-Blodgett film onto a surface.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

In another embodiment, provided is a system for assembling a plurality of one or more elongated structures on a surface, wherein at least one of the elongated structures are at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers, and wherein the system comprises: means for dispersing the one or more elongated structures in a flexible matrix; means for stretching the flexible matrix in a direction to produce a shear force on the one or more elongated structures that causes the at least one elongated structure to align in the direction; means for removing the flexible matrix; and means for transferring the at least one aligned elongated structure to a surface.

In additional aspects of this embodiment: at least one of the elongated structures are semiconductors; at least one of the elongated structures are doped semiconductors; at least one of the elongated structures are bulk-doped semiconductors; at least one of the structures is a doped single-crystal semiconductor; at least one of the structures is an elongated and bulk-doped semiconductor that, at any point along its longitudinal axis, has a largest cross-sectional dimension less than 500 nanometers; at least one of the structures is a free-standing and bulk-doped semiconductor with at least one portion having a smallest width of less than 500 nanometers; at least one of the structures is a doped semiconductor that is at least one of the following: a single crystal, an elongated and bulk-doped semiconductor that, at any point along its longitudinal axis, has a largest cross-sectional dimension less than 500 nanometers, and a free-standing and bulk-doped semiconductor with at least one portion having a smallest width of less than 500 nanometers; the doped semiconductor comprises a semiconductor selected from a group consisting of: Si, Ge, Sn, Se, Te, B, Diamond, P, B—C, B—P($BP_6$), B—Si, Si—C, Si—Ge, Si—Sn and Ge—Sn, SiC, BN/BP/BAs, AlN/AlP/AlAs/AlSb, GaN/GaP/GaAs/GaSb, InN/InP/InAs/InSb, BN/BP/BAs, AlN/AlP/AlAs/AlSb, GaN/GaP/GaAs/GaSb, InN/InP/InAs/InSb, ZnO/ZnS/ZnSe/ZnTe, CdS/CdSe/CdTe, HgS/HgSe/HgTe, BeS/BeSe/BeTe/MgS/MgSe, GeS, GeSe, GeTe, SnS, SnSe, SnTe, PbO, PbS, PbSe, PbTe, CuF, CuCl, CuBr, CuI, AgF, AgCl, AgBr, AgI, $BeSiN_2$, $CaCN_2$, $ZnGeP_2$, $CdSnAs_2$, $ZnSnSb_2$, $CuGeP_3$, $CuSi_2P_3$, (Cu, Ag)(Al, Ga, In, Tl, Fe)(S, Se, Te)$_2$, $Si_3N_4$, $Ge_3N_4$, $Al_2O_3$, (Al, Ga, In)$_2$(S, Se, Te)$_3$, $Al_2CO$; the doped semiconductor comprises a dopant selected from a group consisting of: a p-type dopant from Group III of the periodic table; an n-type dopant from Group V of the periodic table; a p-type dopant selected from a group consisting of: B, Al and In; an n-type dopant selected from a group consisting of: P, As and Sb; a p-type dopant from Group II of the periodic table; a p-type dopant selected from a group consisting of: Mg, Zn, Cd and Hg; a p-type dopant from Group IV of the periodic table; a p-type dopant selected from a group consisting of: C and Si; and an n-type selected from a group consisting of: Si, Ge, Sn, S, Se and Te; the doped semiconductor is doped during growth of the semiconductor.

The features and advantages of the embodiments described above and other features and advantages of these embodiments will be more readily understood and appreciated from the detailed description below, which should be read together with the accompanying drawing Figures.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
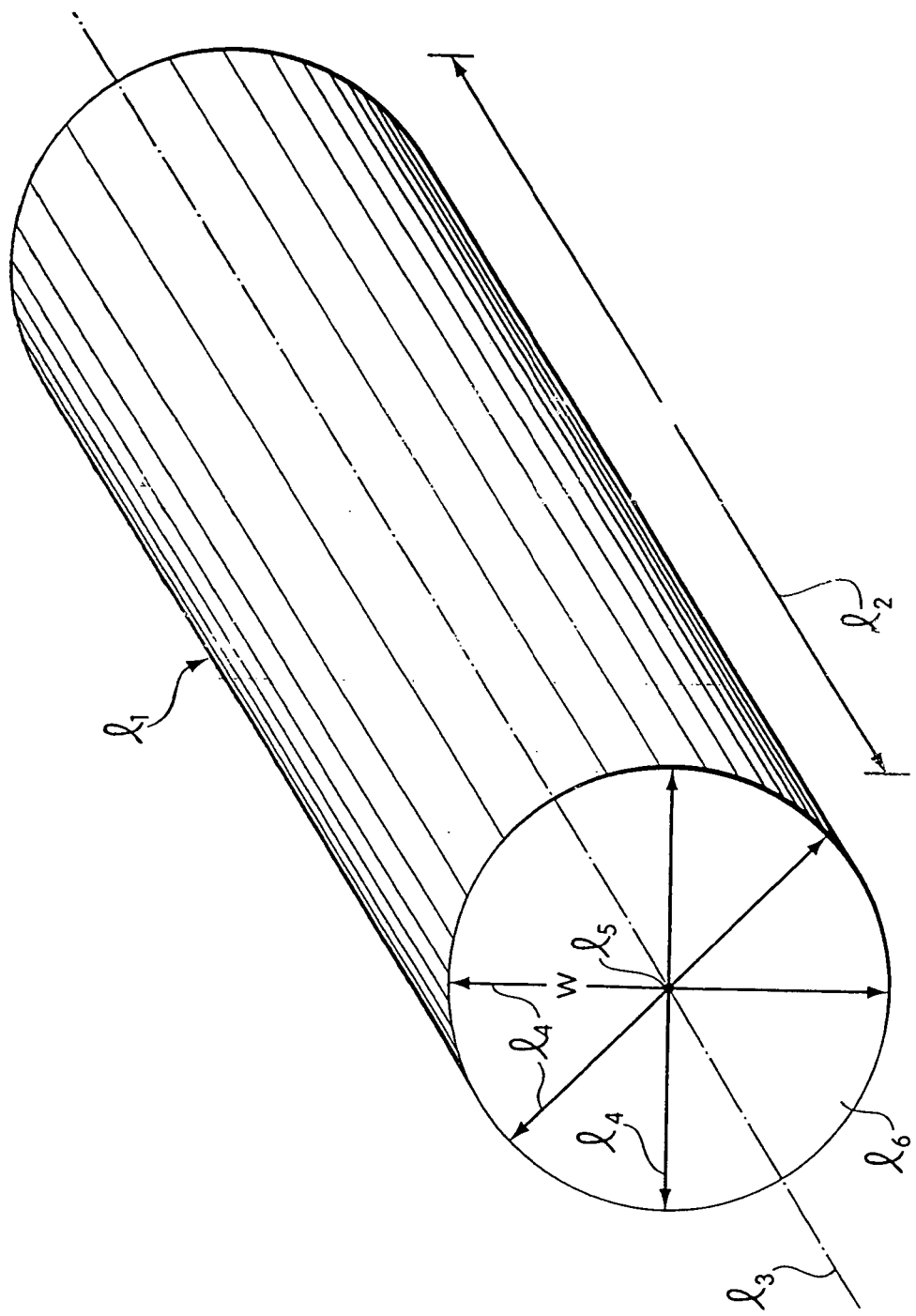
FIG. 1 is a perspective view of an example of a semiconductor article, or nanowire, in accordance with an embodiment of the invention.

The present invention provides, in one aspect, techniques for controlled doping of materials such as semiconductors at a very small spatial scale, and arrangement of doped materials in position relative to each other to create useful devices. One set of embodiments involves doping of a semiconductor, with a dopant (e.g., boron, aluminum, phosphorous, arsenic, etc.) selected according to whether an n-type or p-type semiconductor is desired.

In various embodiments, this invention involves controlled doping of semiconductors selected from among indium phosphide, gallium arsenide, gallium nitride, cadmium selenide, and zinc selenide. Dopants including, but not limited to, zinc, cadmium, or magnesium can be used to form p-type semiconductors in this set of embodiments, and dopants including, but not limited to, tellurium, sulfur, selenium, or germanium can be used as dopants to form n-type semiconductors from these materials. These materials define direct band gap semiconductor materials and these and doped silicon are well known to those of ordinary skill in the art. The present invention contemplates use of any doped silicon or direct band gap semiconductor materials for a variety of uses.

As used herein, a "width" of an article is a distance of a straight line from a point on a perimeter of the article through the center of the article to another point on the perimeter of the article. As used herein, a "width" or "cross-sectional dimension" at a point along the longitudinal axis of an elongated article is a distance along a straight line that passes through the center of the cross-section at the point and that connects two points on the perimeter of the cross section.

As used herein, an "elongated" article (e.g., semiconductor or section thereof) is an article for which, at any point along the longitudinal axis of the article, a ratio of the length of the article to the largest width at the point is greater than 2:1.

As used herein, the "longitudinal axis" of an elongated article is an axis along a largest dimension of the article.

As used herein, the "length" of an elongated article is a distance along the longitudinal axis from end to end of the article.

As used herein, a "longitudinal section" of an elongated article is a portion of the elongated article along the longitudinal axis of the elongated article than can have any length greater than zero and less than or equal to the length of the article.

As used herein, a "cross-section" at a point along the longitudinal axis of an elongated article is a plane at the point across the elongated article that is orthogonal to the longitudinal axis of the article.

As used herein, a "cylindrical" article is an article having an exterior shaped like a cylinder, but does not define or reflect any properties regarding the interior of the article. In other words, a cylindrical article may have a solid interior or may have a hollowed-out interior.

As used herein, a "nanowire" or "NW" is an elongated semiconductor, i.e., a nanoscale semiconductor, that at any point along its length has at least one cross-sectional dimension and, in some embodiments, two orthogonal cross-sectional dimensions less than 500 nanometers, preferably less than 200 nanometers, more preferably less than 150 nanometers, still more preferably less than 100 nanometers, even more preferably less than 70, still more preferably less than 50 nanometers, even more preferably less than 20 nanometers, still more preferably less than 10 nanometers, and even less than 5 nanometers. The cross-section of the elongated semiconductor may have any arbitrary shape, including, but not limited to, circular, square, rectangular, elliptical. Regular and irregular shapes are included.

As used herein, a "nanotube" or "NT" is a nanowire that has a hollowed-out core.

As used herein, a "bulk-doped" article (e.g. semiconductor or section thereof) is an article for which a dopant is incorporated substantially throughout the crystalline lattice of the article, as opposed to an article in which a dopant is only incorporated in particular regions. For example, some articles such as carbon NTs typically are doped after the base material is grown, and thus the dopant only extends a finite distance from the surface or exterior of the carbon NT into the interior of the crystal line lattice. Further, carbon NTs are often combined as nested tubes forming alternating layers of base material and doped base material such that the dopant is not incorporated throughout the crystal line lattice of the base material.

As used herein to describe a "nanowire" or "NW", "doped" means bulk-doped. Accordingly, as used herein, a "doped nanowire" or "doped NW" is a bulk-doped nanowire As used herein, an "array" of articles (e.g., nanowires) comprises a plurality of the articles. As used herein, a "crossed array" is an array where at least one of the articles contacts either another of the articles or a signal node (e.g., an electrode).

As used herein, a first article (e.g., a nanowire or larger-sized structure) "coupled" to a second article is disposed such that the first article either physically contacts the second article or is proximate enough to the second article to influence a property (e.g., electrical property, optical property, magnetic property) of the second article.

Thus, the present invention contemplates, in one aspect, an elongated semiconductor that has a smallest width of less than 500 nanometers that is doped in any way (n-type or p-type). In other embodiments, the semiconductor may have a smallest width less than about 200 nanometers, less than about 150 nanometers, or less than about 100 nanometers. Preferably, the semiconductor has a smallest width of less than about 80 nanometers, more preferably less than about 70 nanometers, preferably less than about 50 nanometers. Smaller widths, such as those with at least one dimension of less than about 20 nanometers, less than about 10 nanometers, or less than about 5 nanometers also are included. In some embodiments, two orthogonal cross-sectional dimensions of the elongated semiconductor may be less than the values given above. The aspect ratio, i.e., the ratio of semiconductor length to largest width, is greater than 2:1. In other embodiments, the aspect ratio may be greater than 4:1, greater than 10:1, greater than 100:1 or even greater than 1000:1. Semiconductors such as these, at very small dimensions, find a variety of uses as described below.

FIG. 1 is a perspective diagram illustrating an example of a cylindrical semiconductor L1, for example, a wire-like semiconductor such as a nanowire. The cylindrical semiconductor L1 has a length L2 and a longitudinal axis L3. At a point L5 along the longitudinal axis L3, the cylindrical semiconductor L1 has a plurality of widths L4 across cross-section L6, where one of the widths L4 is a smallest width at the point L5.

Such semiconductors may be free-standing. As used herein, a "free-standing" article is an article that at some point in its life is not attached to another article or that is in solution.

Further, such a semiconductor may be a bulk-doped semiconductor. As used herein, a "bulk-doped semiconductor" article (e.g. article or section of an article) is a semiconductor for which a dopant is incorporated substantially throughout the crystalline lattice of the semiconductor, as opposed to a semiconductor in which a dopant is only incorporated in particular regions. For example, some semiconductors such as NTs typically are doped after the semiconductor is grown, and thus the dopant only extends a finite distance from the surface or exterior of the nanotube into the interior of the crystalline lattice. Further, NTs are often combined as nested tubes (i.e. cylinders) forming alternating layers of semiconductor and doped semiconductor such that the dopant is not incorporated throughout the crystalline lattice of the semiconductor. It should be understood that "bulk-doped" does not define or reflect a concentration or amount of doping in a semiconductor, nor does it indicate that the doping is necessarily uniform.

For a doped semiconductor, the semiconductor may be doped during growth of the semiconductor. Doping the semiconductor during growth may result in the property that the doped semiconductor is bulk-doped. Further, such doped semiconductors may be controllably doped, such that a concentration of a dopant within the doped semiconductor can be controlled and therefore reproduced consistently, making possible the commercial production of such semiconductors.

A variety of devices may be fabricated using semiconductors such as those described above. Such devices include electrical devices, optical devices, mechanical devices or any combination thereof, including opto-electronic devices and electromechanical devices.

In an embodiment a field effect transistor (FET) is produced using a doped semiconductor having a smallest width of less than 500 nanometers or other width described above. The doped semiconductor can be either a p-type or n-type semiconductor, as is known by those of ordinary skill in the art in FET fabrication. While FETs are known using nanotubes, to the inventors' knowledge, prior arrangements select nanotubes at random, without control over whether the nanotube is metallic or semiconducting. In such a case a very low percentage of devices are functional, perhaps less than one in twenty, or one in fifty, or perhaps approximately one in one hundred. The present invention contemplates controlled doping of nanowires such that a fabrication process can involve fabricating functional FETs according to a technique in which much greater than one in fifty devices is functional. For example, the technique can involve doping a nanowire, then fabricating an FET therefrom.

The invention also provides lightly-doped complementary inverters (complementary metal oxide semiconductors) arranged simply by contact of an n-type semiconductor with a p-type semiconductor, for example by arrangement of crossed n-type and p-type semiconducting nanowires as shown below.

Also provided in accordance with the invention are tunnel diodes with heavily-doped semiconducting components. A tunnel diode can be arranged similarly or exactly the same as a complementary inverter, with the semiconductors being heavily doped rather than lightly doped. "Heavily doped" and "lightly doped" are terms the meaning of which is clearly understood by those of ordinary skill in the art.

One important aspect of the present invention is the ability to fabricate essentially any electronic device that can benefit from adjacent n-type and p-type semiconducting components, where the components are pre-fabricated (doped, in individual and separate processes with components separate from each other when doped) and then brought into contact after doping. This is in contrast to typical prior art arrangements in which a single semiconductor is n-doped in one region and p-doped in an adjacent region, but the n-type semiconductor region and p-type semiconducting regions are initially adjacent prior to doping and do not move relative to each other prior to or after doping. That is, n-type and p-type semiconductors, initially in non-contacting arrangement, are brought into contact with each other to form a useful electronic device. Essentially any device can be made in accordance with this aspect of the invention that one of ordinary skill in the art would desirably make using n-type and p-type semiconductors in combination. Examples of such devices include, but are not limited to, field effect transistors (FETs), bipolar junction transistors (BJTs), tunnel diodes, complementary inverters, light emitting devices, light sensing devices, gates, inverters, AND, NAND, OR, and NOR gates, latches, flip-flops, registers, switches, clock circuitry, static or dynamic memory devices and arrays, state machines, gate arrays, and any other dynamic or sequential logic or other digital devices including programmable circuits. Also included are analog devices and circuitry, including but not limited to, amplifiers, switches and other analog circuitry using active transistor devices, as well as mixed signal devices and signal processing circuitry.

Electronic devices incorporating semiconductor nanowires can be controlled, for example, by electrical, optical or magnetic signals. The control may involve switching between two or more discrete states or may involve continuous control of nanowire current, i.e., analog control. In addition to electrical signals, optical signals and magnetic signals, the devices may be controlled as follows:

(1) The device is switchable in response to biological and chemical species, for example, DNA, protein, metal ions. In more general sense, these species are charged or have dipole.
(2) The device is switchable in response to the mechanical stretching, vibration and bending.
(3) The device is switchable in response to the temperature.
(4) The device is switchable in response to the environmental pressure.
(5) The device is switchable in response to the movement of environmental gas or liquid.

Many devices of the invention make particular use of crossed p/n junctions which can be junctions of crossed n-type and p-type nanowires. Crossed p/n junctions are defined by at least one n-type semiconductor and at least one p-type semiconductor, at least one portion of each material contacting at least one portion of the other material, and each semiconductor including portions that do not contact the other component. They can be arranged by pre-doping the nanowires, then bringing them into proximity with each other using techniques described below.

Light-emission sources are provided in accordance with the invention as well, in which electrons and holes combine, emitting light. One type of light-emission source of the invention includes at least one crossed p/n junction, in particular, crossed p-type and n-type nanowires. In this and other arrangements of the invention using crossed nanowires, the wires need not be perpendicular, but can be. When forward biased (positive charge applied to the p-type wire and a negative charge applied to the n-type wire) electrons flow toward the junction in the n-type wire and holes flow toward the junction in the p-type wire. At the junction, holes and electrons combine, emitting light. Other techniques may be used to cause one or more nanowires, or other semiconductors to emit light, as described below in more detail.

At the size scale of the invention (nanoscale) the wavelength of light emission can be controlled by controlling the size of at least one, and preferably both components that are crossed to form the light-emitting junction. For example, where nanowires are used, a nanowire with larger smallest dimension (broader wire) will provide emission at a lower frequency. For example, in the case of indium phosphide, at size scales associated with typical fabrication processes, the material emits at 920 nanometers. At the size scales of the present invention the wavelength of emission can be controlled to be at wavelengths shorter than 920 nanometers, for example between 920 and 580 nanometers. Wavelengths can be selected within this range, such as 900, 850, 800, 750, 700 nanometers, etc., depending upon wire size.

Thus, one aspect of the invention involves a semiconductor light-emission source that emits at a higher frequency than the semiconductor causing emission emits in its bulk state such increase of the frequency of emission of light is often referred to herein as quantum confinement. "Bulk state", in this context, means a state in which it is present as a component, or a portion of a component having a smallest dimension of greater than 500 nanometers. "Bulk state" also can be defined as that state causing a material's inherent wavelength or frequency of emission. The present invention provides for such control over emission frequency of essentially any semiconducting or doped semiconducting material.

Assembly, or controlled placement of nanowires on surfaces can be carried out by aligning nanowires using an electrical field. An electrical field is generated between electrodes, nanowires are positioned between the electrodes (optionally flowed into a region between the electrodes in a suspending fluid), and will align in the electrical field and thereby can be made to span the distance between and contact each of the electrodes.

In another arrangement individual contact points are arranged in opposing relation to each other, the individual contact points being tapered to form a point directed towards each other. An electric field generated between such points will attract a single nanowire spanning the distance between, and contacting each of, the electrodes. In this way individual nanowires can readily be assembled between individual pairs of electrical contacts. Crossed-wire arrangements, including multiple crossings (multiple parallel wires in a first direction crossed by multiple parallel wires in a perpendicular or approximately perpendicular second direction) can readily be formed by first positioning contact points (electrodes) at locations where opposite ends of the crossed wires desirably will lie. Electrodes, or contact points, can be fabricated via typical microfabrication techniques.

These assembly techniques can be substituted by, or complemented with, a positioning arrangement involving positioning a fluid flow directing apparatus to direct fluid containing suspended nanowires toward and in the direction of alignment with locations at which nanowires are desirably positioned. A nanowire solution can be prepared as follows. After nanowires are synthesized, they are transferred into a solvent (e.g., ethanol), and then are sonicated for several seconds to several minutes to obtain a stable suspension.

Another arrangement involves forming surfaces including regions that selectively attract nanowires surrounded by regions that do not selectively attract them. For example, —$NH_2$ can be presented in a particular pattern at a surface, and that pattern will attract nanowires or nanotubes having surface functionality attractive to amines. Surfaces can be patterned using known techniques such as electron-beam patterning, "soft-lithography" such as that described in International Patent Publication No. WO 96/29629, published Jul. 26, 1996, or U.S. Pat. No. 5,512,131, issued Apr. 30, 1996, each of which is incorporated herein by reference. Additional techniques are described in U.S. patent application Ser. No. 60/142,216, filed Jul. 2, 1999, by Lieber, et al., incorporated herein by reference. Fluid flow channels can be created at a size scale advantageous for placement of nanowires on surfaces using a variety of techniques such as those described in International Patent Publication No. WO 97/33737, published Sep. 18, 1997, and incorporated herein by reference. Other techniques include those described in U.S. patent application Ser. No. 09/578,589, filed May 25, 2000, and incorporated herein by reference.

FIGS. 7A-7E show one such technique for creating a fluid flow channel using a polydimethyl siloxane (PDMS) mold. Channels can be created and applied to a surface, and a mold can be removed and re-applied in a different orientation to provide a cross flow arrangement or different arrangement.

The flow channel arrangement can include channels having a smallest width of less than 1 millimeter, preferably less than 0.5 millimeter, 200 microns or less. Such channels are easily made by fabricating a master by using photolithography and casting PDMS on the master, as described in the above-referenced patent applications and international publications. Larger-scale assembly is possible as well. The area that can be patterned with nanowire arrays is defined only by the feature of the channel which can be as large as desired.

Semiconductor nanowires have a crystalline core sheathed with 1-10 nm thick of amorphous oxide. This allows surface modification to terminate the surface with various functional groups. For example, we can use molecules, one end of which is alkyloxysilane group (e.g. —$Si(OCH_3)$) reacting with nanowire surface, the other end of which comprise (1) —$CH_3$, —$COOH$, —$NH_2$, —$SH$, —$OH$, hydrazide, and aldehyde groups; (2) light activatable moieties: aryl azide, fluorinated aryl azide, benzophenone etc. The substrate and electrodes are also modified with certain functional groups to allow nanowires to specifically bind or not bind onto the substrate/electrodes surface based on the their interaction.

Surface-functionalized nanowires can also be coupled to the substrate surface with functional cross-linkers, e.g. (1) Homobifunctional cross-linkers, comprising homobifunctional NHS esters, homobifunctional imidoesters, homobifunctional sulfhydryl-reactive linkers, difluorobenzene derivatives, homobifunctional photoactive linkers, homobifunctional aldehyde, bis-epoxides, homobifunctional hydrazide etc. (2) Heterobifunctional cross-linkers (3) Trifunctional cross-linkers.

The assembly of nanowires onto substrate and electrodes can also be assisted using bimolecular recognition. For example, we can immobilize one biological binding partner onto the nanowire surface and the other one onto substrate or electrodes using physical adsorption or covalently linking. Some good bio-recognitions are: DNA hybridization, antibody-antigen binding, biotin-avidin (or streptavidin) binding.

There are many techniques that may be used to grow bulk-doped semiconductors, such as nanowires, and for doping such nanowires during growth.

Figure 2:
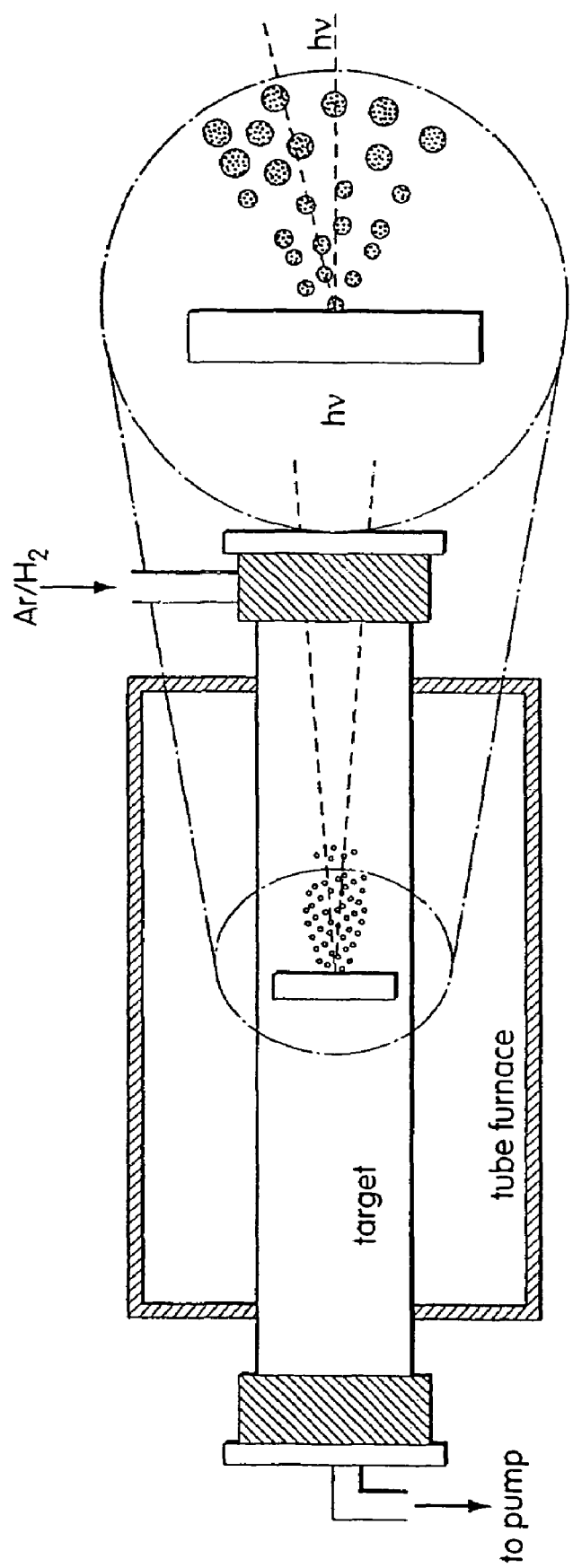
FIG. 2 is a simplified schematic diagram of an example of a laser assisted catalytic growth process for fabrication of semiconductor nanowires.
Figure 3:
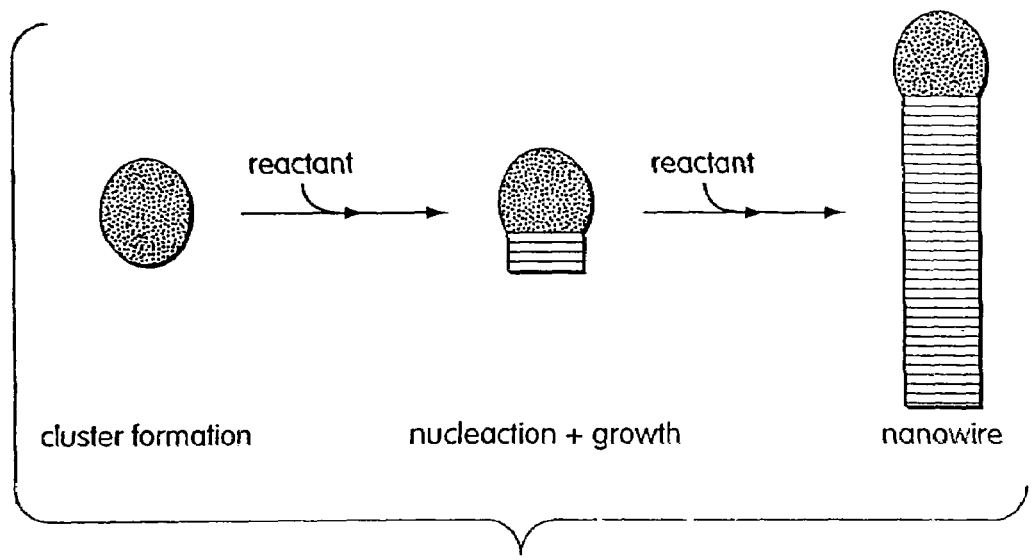
FIG. 3 is a schematic diagram that illustrates nanowire growth.

For example, SiNWs (elongated nanoscale semiconductors) may be synthesized using laser assisted catalytic growth (LCG). As shown in FIGS. 2 and 3, laser vaporization of a composite target that is composed of a desired material (e.g. InP) and a catalytic material (e.g. Au) creates a hot, dense vapor which quickly condenses into liquid nanoclusters through collision with the buffer gas. Growth begins when the liquid nanoclusters become supersaturated with the desired phase and continues as long as the reactant is available. Growth terminates when the nanowires pass out of the hot reaction zone or when the temperature is turned down. Au is generally used as catalyst for growing a wide range of elongated nanoscale semiconductors. However, The catalyst is not limited to Au only. A wide rage of materials such as (Ag, Cu, Zn, Cd, Fe, Ni, Co . . . ) can be used as the catalyst. Generally, any metal that can form an alloy with the desired semiconductor material, but doesn't form more stable compound than with the elements of the desired semiconductor can be used as the catalyst. The buffer gas can be Ar, $N_2$, and others inert gases. Sometimes, a mixture of $H_2$ and buffer gas is used to avoid un-desired oxidation by residue oxygen. Reactive gas can also be introduced when desired (e.g. ammonia for GaN). The key point of this process is laser ablation generates liquid nanoclusters that subsequently define the size and direct the growth direction of the crystalline nanowires. The diameters of the resulting nanowires are determined by the size of the catalyst cluster, which in turn can be varied by controlling the growth conditions (e.g. background pressure, temperature, flow rate . . . ). For example, lower pressure generally produces nanowires with smaller diameters. Further diameter control can be done by using uniform diameter catalytic clusters.

Figure 4:
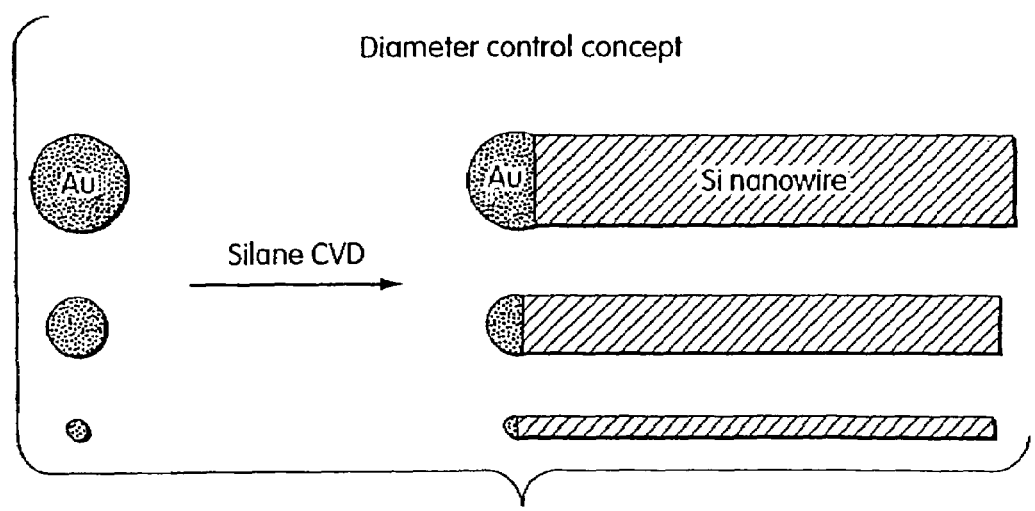
FIG. 4 is a schematic diagram that illustrates an example of a method for controlling nanowire diameter.

With same basic principle as LCG, if uniform diameter nanoclusters (less than 10-20% variation depending on how uniform the nanoclusters are) are used as the catalytic cluster, nanowires with uniform size (diameter) distribution can be produced, where the diameter of the nanowires is determined by the size of the catalytic clusters, as illustrated in FIG. 4. By controlling the growth time, nanowires with different lengths can be grown.

With LCG, nanowires can be flexibly doped by introducing one or more dopants into the composite target (e.g. Ge for n-type doping of InP). The doping concentration can be controlled by controlling the relative amount of doping element, typically 0-20%, introduced in the composite target.

Laser ablation may be used as the way to generate the catalytic clusters and vapor phase reactant for growth of nanowires and other related elongated nanoscale structures. but fabrication is not limited to laser ablation. Many ways can be used to generate vapor phase and catalytic clusters for nariowire growth (e.g. thermal evaporation).

Another technique that may be used to grow nanowires is catalytic chemical vapor deposition (C-CVD). C-CVD utilizes the same basic principles as LCG, except that in the C-CVD method, the reactant molecules (e.g., silane and the dopant) are from vapor phase molecules (as opposed to vapor source from laser vaporization).

In C-CVD, nanowires can be doped by introducing the doping element into the vapor phase reactant (e.g. diborane and phosphane for p-type and n-type doped nanowire). The doping concentration can be controlled by controlling the relative amount of the doping element introduced in the composite target. It is not necessary to obtain elongated nanoscale semiconductors with the same doping ratio as that in the gas reactant. However, by controlling the growth conditions (e.g. temperature, pressure . . . ), nanowires with same doping concentration can be reproduced. And the doping concentration can be varied over a large range by simply varying the ratio of gas reactant (e.g. 1 ppm-10%).

Figure 5:
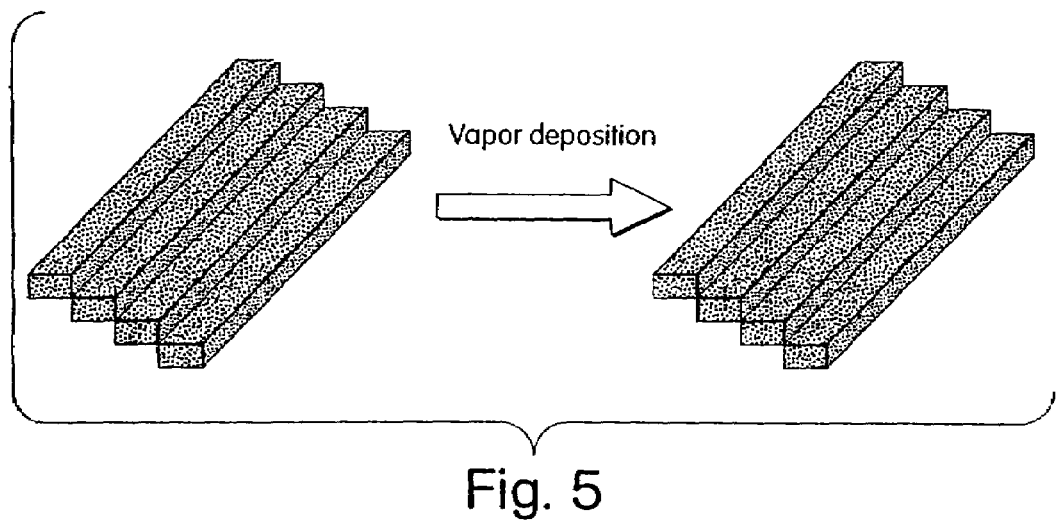
FIG. 5 is a schematic diagram that illustrates nanowire fabrication by deposition on the edge of surface steps.
Figure 6:
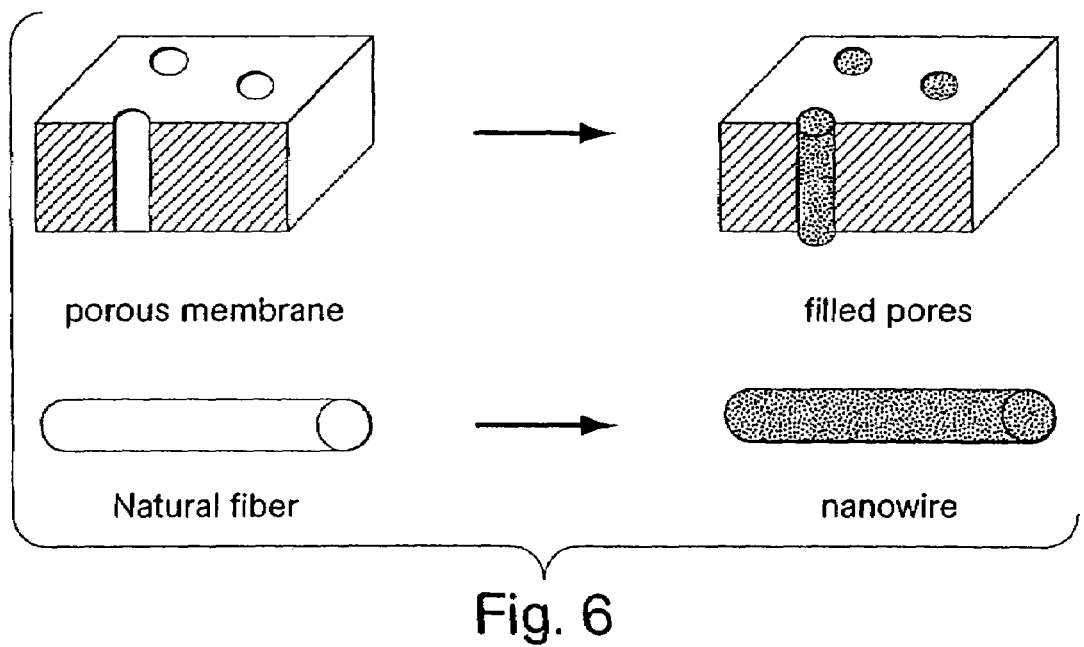
FIG. 6 is a schematic diagram that illustrates nanowire growth by vapor deposition in or on an elongated template.
Figure 7A:
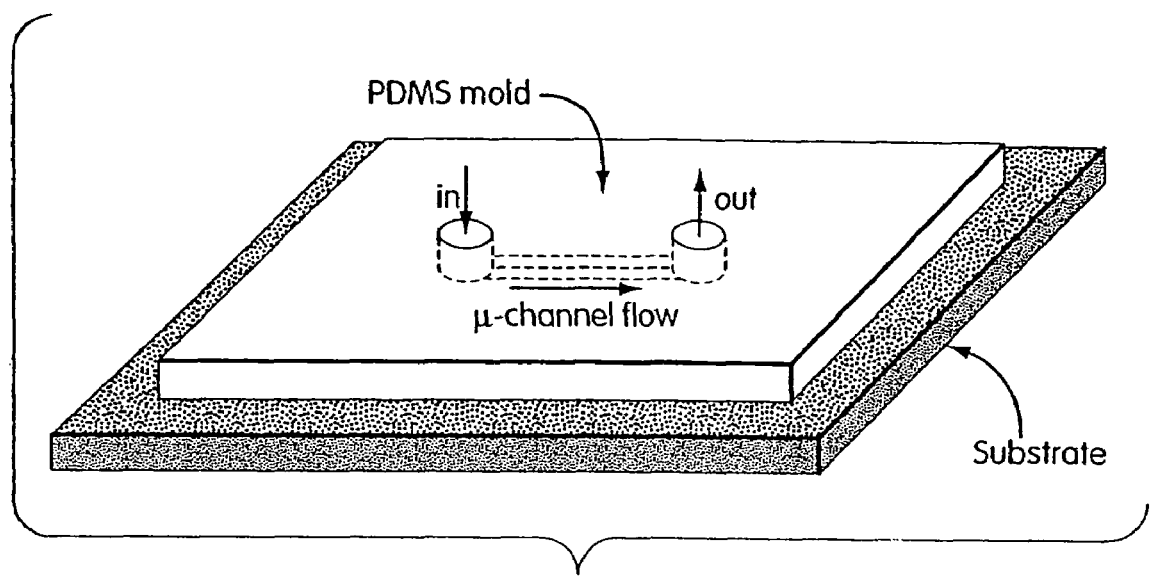
FIGS. 7A-7E illustrate orthogonal assembly of semiconductor nanowires to form devices.
Figure 7B:
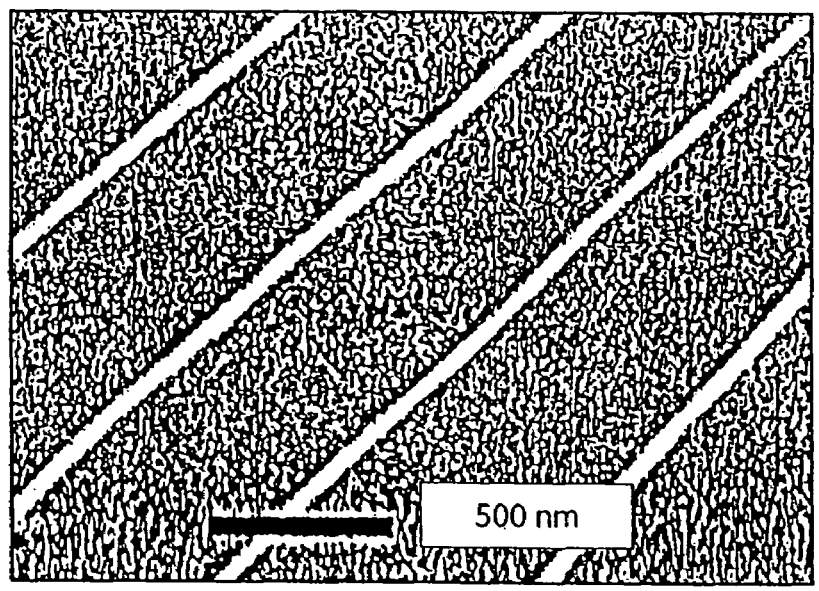
Figure 7C:
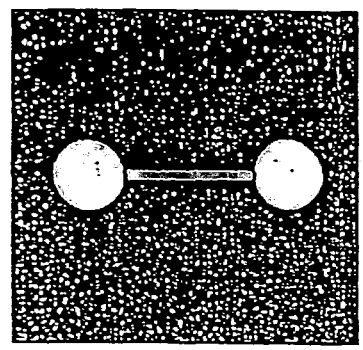
Figure 7D:
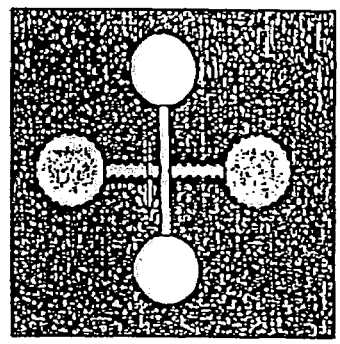
Figure 7E:
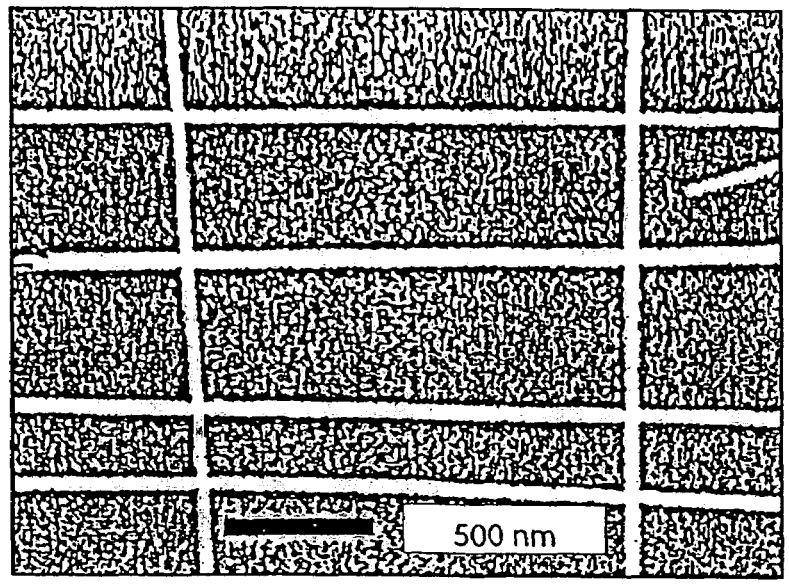

There are several other techniques that may be used to grow elongated nanoscale semiconductors such as nanowires. For example, nanowires of any of a variety of materials can be grown directly from vapor phase through a vapor-solid process. Also, nanowires can also be produced by deposition on the edge of surface steps, or other types of patterned surfaces, as shown in FIG. 5. Further, nanowires can be grown by vapor deposition in/on any general elongated template, for example, as shown in FIG. 6. The porous membrane can be porous silicon, anodic alumina or diblock copolymer and any other similar structure. The natural fiber can be DNA molecules, protein molecules carbon nanotubes, any other elongated structures. For all the above described techniques, the source materials can be came from a solution phase rather than a vapor phase. While in solution phase, the template can also be column micelles formed by surfactant molecules in addition to the templates described above.

Using one or more of the above techniques, elongated nanoscale semiconductors, including semiconductor nanowires and doped semiconductor nanowires, can be grown. Such bulk-doped semiconductors may include various combinations of materials, including semiconductors and dopants. The following are non-comprehensive lists of such materials. Other materials may be used. Such materials include, but are not limited to:

Elemental Semiconductors
  Si, Ge, Sn, Se, Te, B, Diamond, P

Solid Solution of Elemental Semiconductors
  B—C, B—P(BP$_6$), B—Si, Si—C, Si—Ge, Si—Sn, Ge—Sn IV-IV Group Semiconductors
  SiC III-V Semiconductors
  BN/BP/BAs, AlN/AlP/AlAs/AlSb, GaN/GaP/GaAs/GaSb, InN/InP/InAs/InSb, Alloys of III-V Group
  any combination of two or more of the above compound (e.g.: AlGaN, GaPAs, InPAs, GaInN, AlGaInN, GaInAsP . . . )

II-VI Semiconductors
  ZnO/ZnS/ZnSe/ZnTe, CdS/CdSe/CdTe, HgS/HgSe/HgTe, BeS/BeSe/BeTe/MgS/MgSe Alloys of II-VI Group
  any combination of two or more of the above compound (e.g.: (ZnCd)Se, Zn(SSe) . . . )

Alloy of II-VI and III-V Semiconductors
  combination of any one II-VI and one III-V compounds, eg.(GaAs)$_x$(ZnS)$_{1-x}$ IV-VI Semiconductors
  GeS, GeSe, GeTe, SnS, SnSe, SnTe, PbO, PbS, PbSe, PbTe I-VII Semiconductors
  CuF, CuCl, CuBr, CuI, AgF, AgCl, AgBr, AgI Other Semiconductor Compounds
  II-IV-V$_2$: BeSiN$_2$, CaCN$_2$, ZnGeP$_2$, CdSnAs$_2$, ZnSnSb$_2$ . . .
  I-IV$_2$-V$_3$: CuGeP$_3$, CuSi$_2$P$_3$ . . .
  I-III-VI$_2$: (Cu, Ag)(Al, Ga, In, Tl, Fe)(S, Se, Te)$_2$
  IV$_3$-V$_4$: Si$_3$N$_4$, Ge$_3$N$_4$ . . .
  III$_2$-VI$_3$: Al$_2$O$_3$, (Al, Ga, In)$_2$(S, Se, Te)$_3$ . . .
  III$_2$-IV-VI: Al$_2$CO . . .

For Group IV semiconductor materials, a p-type dopant may be selected from Group III, and an n-type dopant may be selected from Group V. For silicon semiconductor materials, a p-type dopant may be selected from the group consisting of B, Al and In, and an n-type dopant may be selected from the group consisting of P, As and Sb. For Group III-V semiconductor materials, a p-type dopant may be selected from Group II, including Mg, Zn, Cd and Hg, or Group IV, including C and Si. An n-type dopant may be selected from the group consisting of Si, Ge, Sn, S, Se and Te. It will be understood that the invention is not limited to these dopants.

EXAMPLES

Doping and Electrical Transport in Nanowires

Single crystal n-type and p-type silicon nanowires (SiNWs) have been prepared and characterized by electrical transport measurements. As used herein, a "single crystal" item is an item that has covalent bonding, ionic bonding, or a combination thereof throughout the item. Such a single crystal item may include defects in the crystal, but is distinguished from an item that includes one or more crystals, not ionically or covalently bonded, but merely in close proximity to one another. Laser catalytic growth was used to introduce controllably either boron or phosphorous dopants during the vapor phase growth of SiNWs. Two terminal, gate-dependent measurements made on individual boron-doped and phosphorous-doped SiNWs show that these materials behave as p-type and n-type materials, respectively. Estimates of the carrier mobility made from gate-dependent transport measurements are consistent with diffusive transport. In addition, these studies show it is possible to heavily dope SiNWs and approach a metallic regime. Temperature-dependent measurements made on heavily doped SiNWs show no evidence for coulomb blockade at temperature down to 4.2 K, and thus testify to the structural and electronic uniformity of the SiNWs. Potential applications of the doped SiNWs are discussed.

Currently, there is intense interest in one dimensional (1D) nanostructures, such as nanowires and nanotubes, due to their potential to test fundamental concepts about how dimensionality and size affect physical properties, and to serve as critical building blocks for emerging nanotechnologies. Of particular importance to 1D nanostructures is the electrical transport through these "wires", since predictable and controllable conductance will be critical to many nanoscale electronics applications. To date, most efforts have focused on electrical transport in carbon nanotubes. These studies have shown interesting fundamental features, including the existence of coherent states extending over hundreds of nanometers, ballistic conduction at room temperature, and Luttinger liquid behavior, and have demonstrated the potential for devices such as field effect transistors. However, there are important limitations of nanotubes. First, the specific growth of metallic or semiconducting tubes, which depends sensitively on diameter and helicity, is not possible. Studies dependent on the specific conducting behavior must thus rely on chance I observation. Second, controlled doping of semiconducting nanotubes is not possible, although it is potentially critical for devices applications. Semiconductor nanowires, however, can overcome these limitations of carbon nanotubes. These nanowires will remain semiconducting independent of diameter, and moreover, it should be possible to take advantage of the vast knowledge from the semiconductor industry to dope the nanowires.

To this end, we here report the first demonstration of controlled doping of SiNWs and the characterization of the electrical properties of these doped nanowires using transport measurements. Gate-dependent, two terminal measurements demonstrate that boron-doped (B-doped) and phosphorous-doped (P-doped) SiNWs behave as p-type and n-type materials, respectively, and estimates of the carrier mobilities suggest diffusive transport in these nanowires. In addition, temperature dependent measurements made on heavily doped SiNWs show no evidence for coulomb blockade at temperatures down to 4.2 K.

SiNWs were synthesized using the laser-assisted catalytic growth (LCG) we have described previously. Briefly, a Nd-YAG laser (532 nm; 8 ns pulse width, 300 mJ/pulse, 10 Hz) may be used to ablate a gold target, which produces gold nanocluster catalyst particles within a reactor. The SiNWs may be grown in a flow of $SiH_4$ as the reactant. Such SiNWs may be doped with boron by incorporating $B_2H_6$ in the reactant flow, and may be doped with phosphorous using a Au-P target (99.5:0.5 wt %, Alfa Aesar) and additional red phosphorous (99%, Alfa Aesar) at the reactant gas inlet. Transmission electron microscopy (TEM) measurements demonstrate that doped SiNWs grown using this technique have a single crystal silicon core that is covered by a dense $SiO_x$ sheath as described previously.

Electrical contact to individual SiNWs were made using standard electron beam lithography methods using a JEOL 6400 writer. The nanowires were supported on oxidized Si substrate (1-10 $\Omega$-cm resistivity, 600 nm $SiO_2$, Silicon Sense, Inc.) with the underlying conducting Si used as a back gate. The contacts to the SiNWs were made using thermally evaporated Al (50 nm) and Au (150 nm). Electrical transport measurements were made using a homebuilt system with less than or equal to 1 pA noise under computer control. The temperature-dependent measurements were made in a Quantum Design magnetic property measurement system.

TEM studies show that the boron and phosphorous-doped SiNWs are single crystals, although these measurements do not have sufficient sensitivity to quantify the boron or phosphorous doping level in individual wires. We can, however, demonstrate unambiguously the presence of p-type (boron) or n-type (phosphorous) dopants and the relative doping levels using electrical transport spectroscopy. In these measurements, a gate electrode is used to vary the electrostatic potential of the SiNW while measuring current versus voltage of the nanowire. The change in conductance of SiNWs as function of gate voltage can be used to distinguish whether a given nanowire is p-type or n-type since the conductance will vary oppositely for increasing positive (negative) gate voltages.

Figure 8A:
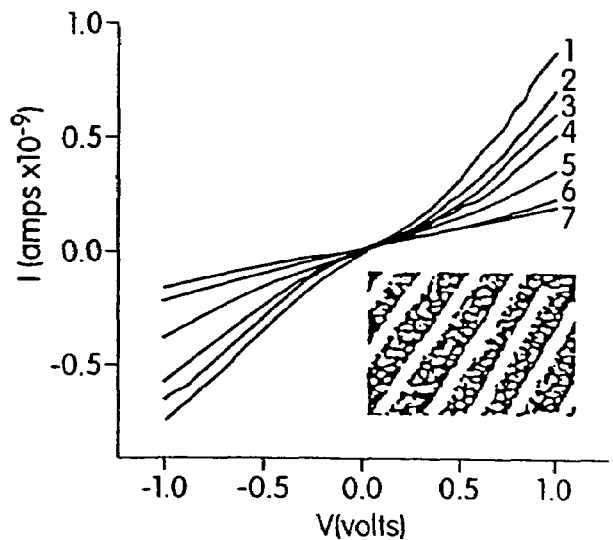
FIGS. 8A-8C show silicon nanowire current as a function of bias voltage for different doping levels and gate voltages.
Figure 8B:
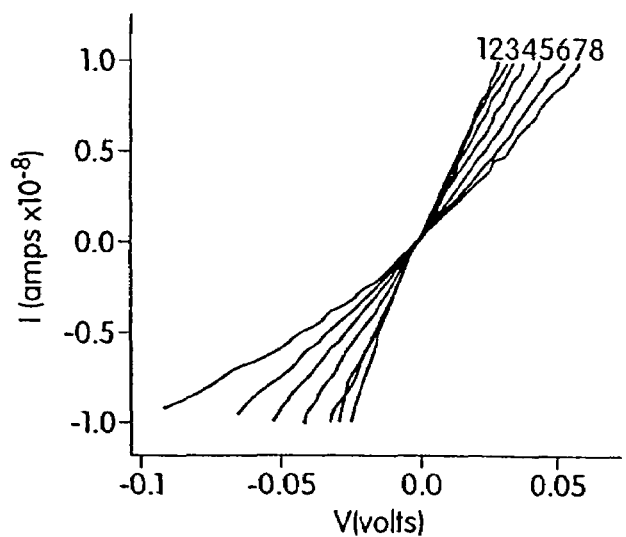
Figure 8C:
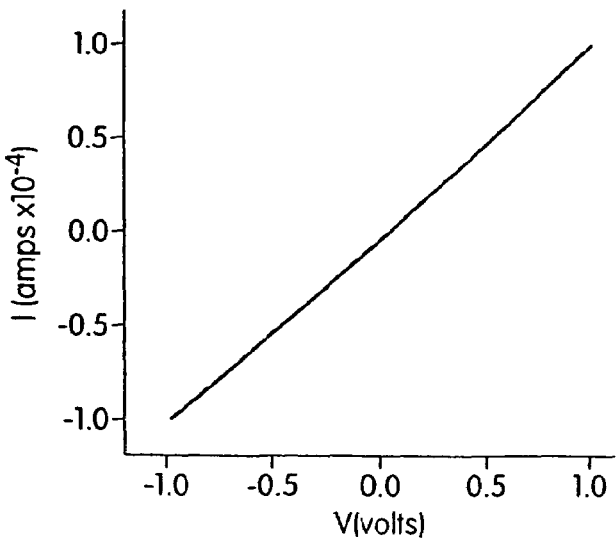

Typical gate-dependent current versus bias voltage (I-V) curves recorded on intrinsic and B-doped SiNWs are shown in FIGS. 8A-8C. The two B-doped wires shown in FIGS. 8B and 8C were synthesized using $SiH_4$: $B_2H_6$ ratios of 1000:1 and 2:1, respectively. In general, the two terminal I-V curves are linear and thus suggest that the metal electrodes make ohmic contacts to the SiNWs. The small nonlinearity observed in the intrinsic nanowire indicates that this contact is slightly nonohmic. Analysis of I-V data, recorded at zero gate voltage ($V_g$=0), which accounts for contributions from the contact resistance and oxide coating on the SiNW, yield a resistivity of $3.9 \times 10^2$ $\Omega$-cm. Significantly, when $V_g$ is made increasingly negative (positive), the conductance increases (decreases). This gate dependence shows that the SiNW is a p-doped semiconductor (discussion below). Similar I-V versus $V_g$ curves were recorded for the lightly B-doped SiNW, and show that it is also p-type. Moreover, the $V_g$=0 resistivity of this B-doped SiNW (1 $\Omega$-cm) is more than two orders of magnitude smaller than the intrinsic SiNW, and demonstrates clearly our ability to control conductivity chemically. This latter point is further supported by I-V measurements on the heavily B-doped SiNWs show in FIG. 8C. This wire has a very low resistivity of $6.9 \times 10^{-3}$ $\Omega$-cm and shows no dependence on $V_g$; that is, I-V data recorded with $V_g$ of 0 and 20 V are overlapping. These results are consistent with a high carrier concentration that is near the metallic limit.

We have also measured $V_g$-dependent transport in lightly and heavily P-doped SiNWs. The I-V recorded on the lightly doped nanowire (FIG. 9A) is somewhat nonlinear, which indicates nonideal contact between the electrodes and nanowire, and the $V_g$ dependence is opposite of that observed for the B-doped SiNWs. Significantly, this observed gate dependence is consistent with n-type material as expected for P-doping. The estimated resistivity of this wire at $V_g$=0 is $2.6 \times 10^2$ $\Omega$-cm. This relatively high resistivity is suggestive of a low doping level and/or low mobility. In addition, heavily P-doped SiNWs have also been made and studied. The I-V data recorded on a typical heavily P-doped wire are linear, have a resistivity of $2.3 \times 10^2$ $\Omega$-cm, and shows no dependence on $V_g$. The low resistivity (four orders of magnitude smaller than the lightly P-doped sample) and $V_g$ independence demonstrate that high carrier concentrations can also be created via P-doping of the SiNWs.

The above results demonstrate that boron and phosphorous can be used to change the conductivity of SiNWs over many orders of magnitude and that the conductivity of the doped SiNWs respond oppositely to positive (negative) $V_g$ for boron and phosphorous dopants. Indeed, the $V_g$-dependence provides strong proof for p-type (holes) doping with boron and n-type (electrons) doping with phosphorous in the SiNWs. The observed gate dependencies can be understood by referring to the schematics shown in FIGS. 10A and 10B, which show the effect of the electrostatic potential on the SiNW bands. In these diagrams, a p-type nanowire (a) and n-type nanowire (b) are contacted at both ends to metal electrodes. As for a conventional metal-semiconductor interface, the SiNW bands bend (up for p-type; down for n-type) to bring the nanowire Fermi level in line with that of the metal contacts. When $V_g$>0, the bands are lowered, which depletes the holes in B-doped SiNWs and suppress conductivity, but leads to an accumulation of electrons in P-doped SiNWs and enhance the conductivity. Conversely, $V_g$<0 will raise the bands and increase the conductivity of B-doped (p-type) SiNWs and decrease the conductivity of the P-doped (n-type) nanowires.

In addition, it is possible to estimate the mobility of carriers from the transconductance, $dI/dV_g = \mu C/L^2$) V, where $\mu$ is the carrier mobility, C is the capacitance, and L is the length of the SiNW. The SiNW capacitance is given by $C \approx 2\pi\epsilon\epsilon_o L/\ln(2h/r)$, where $\epsilon$ is the dielectric constant, h is the thickness of the silicon oxide layer, and r is the SiNW radius. Plots of $dI/dV_g$ versus V were found to be linear for the intrinsic (FIG. 8A) and lightly B-doped (FIG. 8B) SiNWs, as expected for this model. The slopes of $dI/dV_g$ for the intrinsic ($2.13 \times 10^{-11}$) and B-doped ($9.54 \times 10^{-9}$) SiNW yield mobilities of $5.9 \times 10^{-3}$ $cm^2$/V-s and 3.17 $cm^2$/V-s, respectively. The mobility for the B-doped nanowire is comparable to that expected in bulk Si at a doping concentration of $10^{20}$ $cm^{-3}$. We also note that the mobility is expected to increase with decreasing dopant concentration, although in our intrinsic (low dopant concentration) SiNW the mobility is extremely low. It is possible that the reduced mobility is due to enhanced scattering in the smaller diameter (intrinsic) SiNW. We believe that future studies of the mobility as a function of diameter (for constant dopant concentration) should illuminate this important point.

Figure 11A:
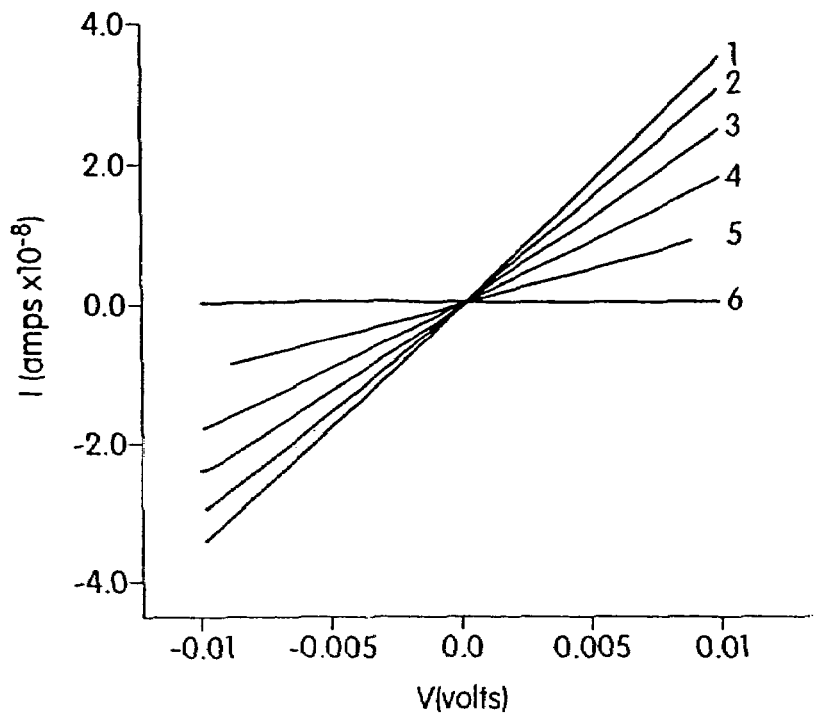
FIGS. 11A and 11B show temperature dependent current-voltage curves recorded on a heavily boron doped silicon nanowire.
Figure 11B:
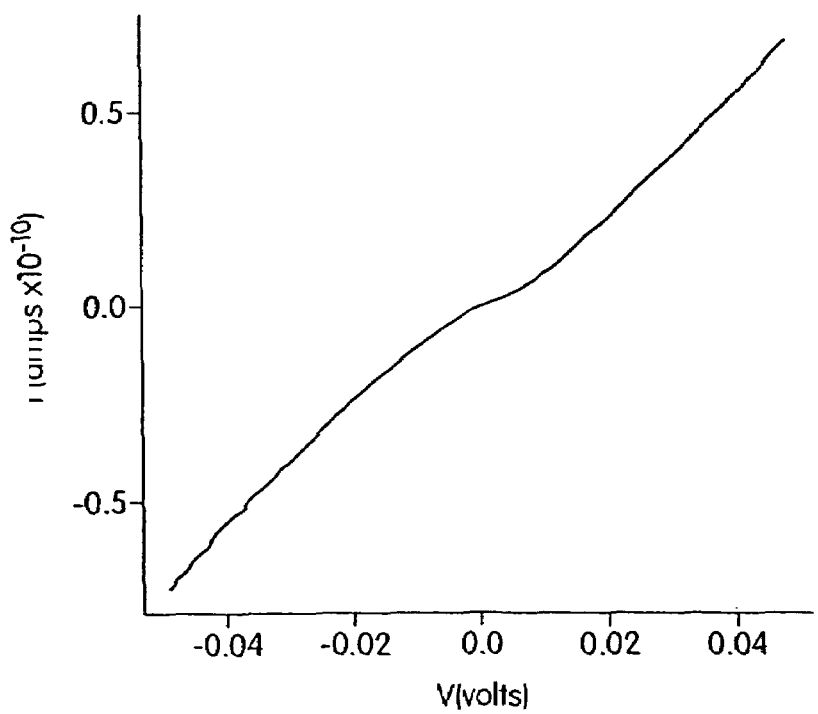

Lastly, we have carried out preliminary temperature-dependent studies of heavily B-doped SiNWs. Temperature dependent I-V curves show that the conductance decreases with decreasing temperature, as expected for a doped semiconductor (FIGS. 11A and 11B). More importantly, we see no evidence for a coulomb blockade down to our lowest accessible temperature (FIG. 11B). The small nonlinearity near V=0 is attributed to a contact effect since high resolution I-V versus $V_g$ measurements show no signature for coulomb blockade. Coulomb charging effect in this homogenous wire between the electrodes (a 150 nm thick 2.3 μm long wire) would require a temperature below about 26 mK estimated from $kT=e^2/2C$. This indicates strongly that variations in SiNW diameter and defects are sufficiently small that they do not effectively "break up" the SiNW into small islands, which would exhibit coulomb blockade at these temperatures. These results contrast studies of lithographically patterned SiNWs, which show coulomb blockade, and testify to the high quality of our free standing nanowires.

Single crystal n-type and p-type silicon nanowires (SiNWs) have been prepared and characterized by electrical transport measurements. Laser catalytic growth was used to introduce controllably either boron or phosphorous dopants during the vapor phase growth of SiNWs. Two-terminal, gate-dependent measurements made on individual boron-doped and phosphorous-doped SiNWs show that these materials behave as p-type and n-type materials, respectively. Estimates of the carrier mobility made from gate-dependent transport measurements are consistent with diffusive transport, and show an indication for reduced mobility in smaller diameter wires. In addition, these studies show it is possible to incorporate high dopant concentrations in the SiNWs and approach the metallic regime. Temperature-dependent measurements made on heavily doped SiNWs show no evidence for single electron charging at temperatures down to 4.2 K, and thus suggest that the SiNWs possess a high degree of structural and doping uniformity.

We believe that our successful doping of SiNWs to create n-type and p-type materials will open up exciting opportunities in nanoscale science and technology. Doped SiNWs will be candidates for investigating fundamental issues of transport in ID nanostructures. The structures studies in this paper are also field effect transistors (FETs), and it will be possible using self-assembly techniques to integrate many SiNW FETs into structures perhaps for nanoelectronics applications. It should also be possible to combine p-type and n-type SiNWs, for example in crossed arrays, to create p-n junctions that could also be considered for devices and sensors in the future.

Crossed SiNW p-n junctions have been formed by directed assembly of p-type (n-type) SiNWs over n-type (p-type) SiNWs. Transport measurements exhibit rectification in reverse bias and a sharp current onset in forward bias. Simultaneous measurements made on the p-type and n-type SiNWs making up the junction demonstrate that the contacts to these nanowires are ohmic (nonrectifying), and thus that the rectifying behavior is due to the p-n junction between the two SiNWs.

FIG. 8A shows current (I) vs bias voltage (V) curves recorded on a 70 nm diameter intrinsic SiNW at different gate voltages ($V_g$). Curves 1, 2, 3, 4, 5, 6, and 7 correspond to $V_g$=−30, −20, −10, 0 V, 10, 20, and 30 V, respectively. The inset is a typical scanning electron micrograph of the SiNW with metal contacts (scale bar=10 μm). FIG. 8B shows I-V data recorded on a 150 nm diameter B-doped SINW; curves 1-8 correspond to $V_g$=−20, −10, −5, 0, 5, 10, 15 and 20 V, respectively. FIG. 8C shows I-V curves recorded on a 150 nm diameter heavily B-doped SiNW; $V_g$=20 V (solid line) and 0 V (heavy dashed line).

Figure 9A:
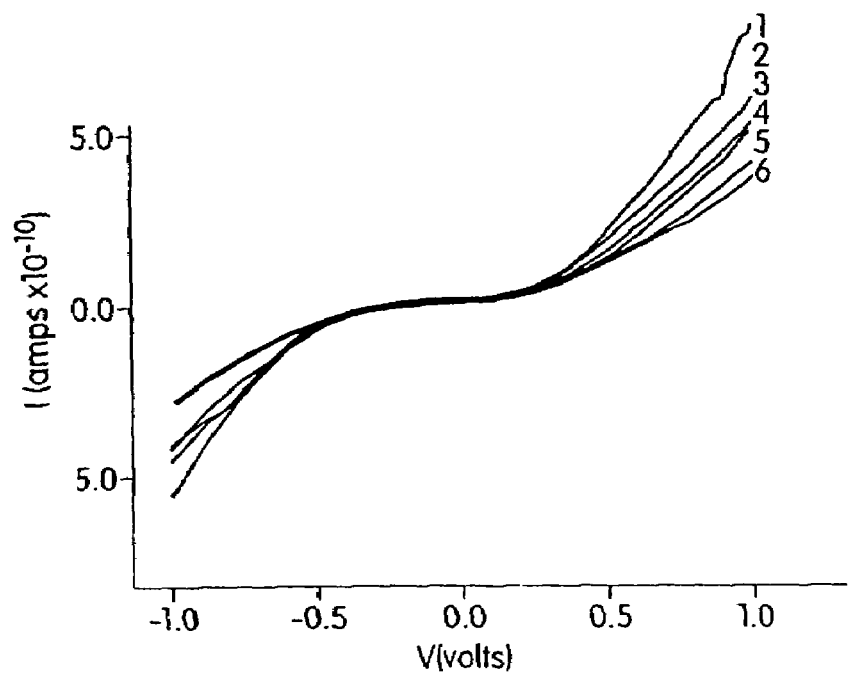
FIGS. 9A and 9B show silicon nanowire current as a function of bias voltage for different phosphorous doping levels and gate voltages.
Figure 9B:
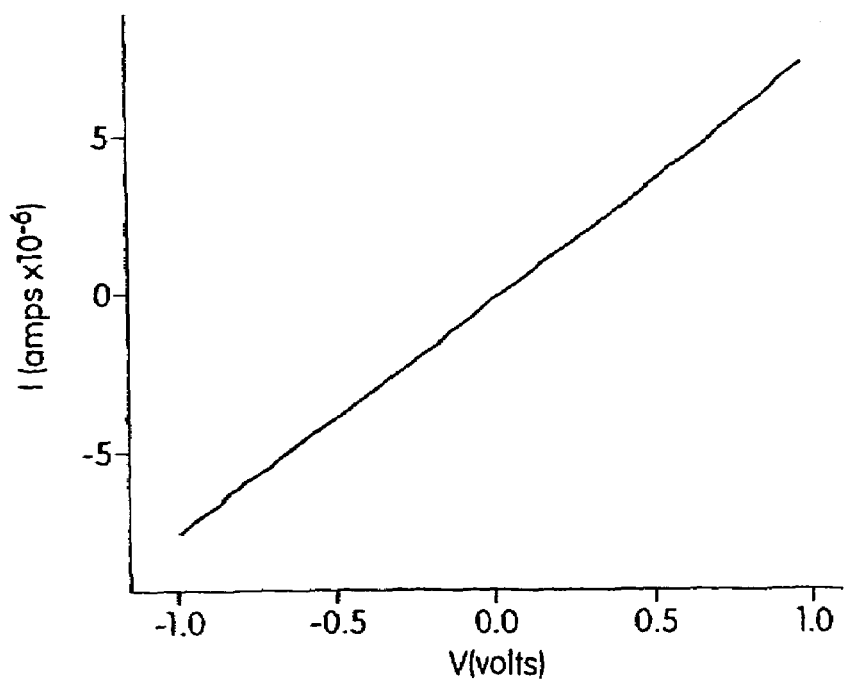

FIG. 9A shows I-V data recorded on a 60 nm diameter P-doped SiNW. Curves 1, 2, 3, 4, 5, and 6 correspond to $V_g$=20, 5, 1, 0, −20, and −30 V, respectively. FIG. 9B shows I-V curves recorded on a 90 nm diameter heavily P-doped SiNW; $V_g$=0 V (solid line) and −20 V (heavy dash line).

Figure 10A:
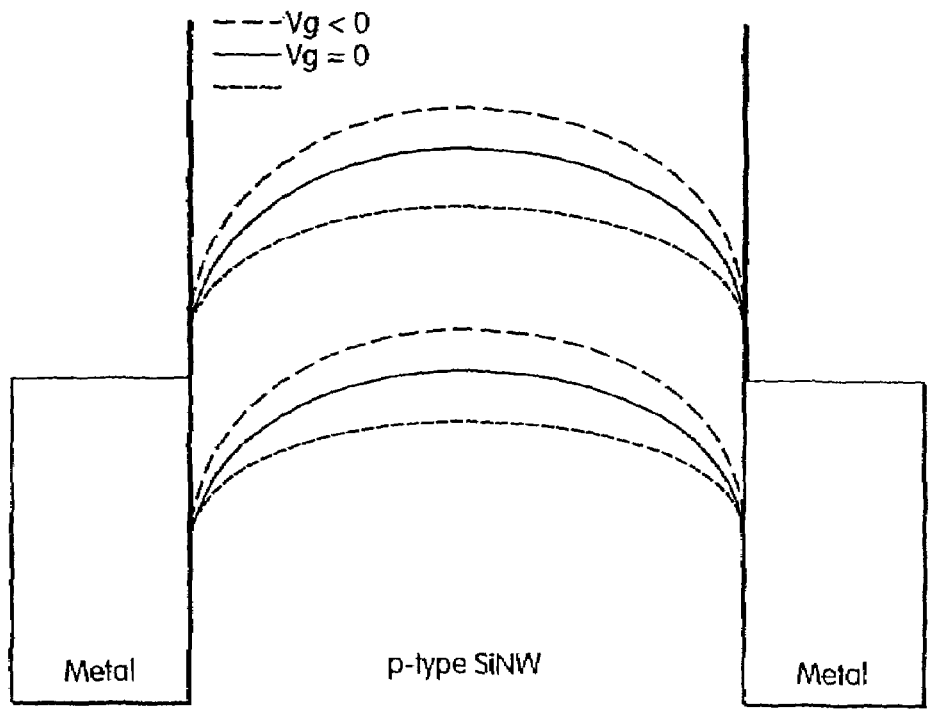
FIGS. 10A and 10B show energy band diagrams for p-type and n-type silicon nanowire devices, respectively.
Figure 10B:
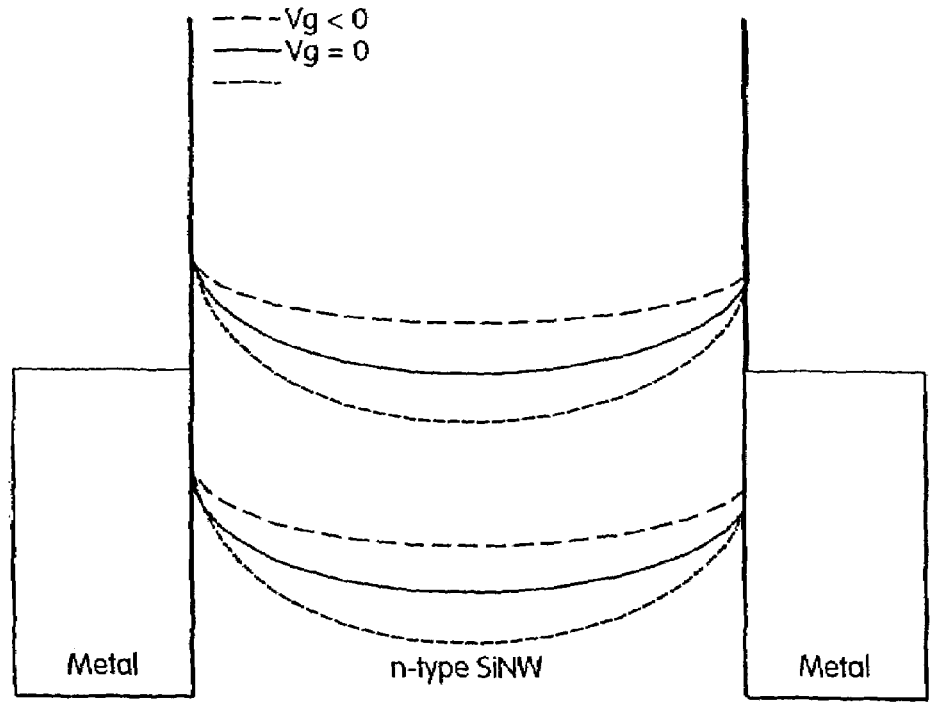

FIG. 10A shows energy band diagrams for p-type SiNW devices. FIG. 10B shows energy band diagrams for n-type SiNW devices. The diagrams show schematically the effect of $V_g$ on the electrostatic potential for both types of nanowires.

FIGS. 11A and 11B show temperature dependent I-V curves recorded on a heavily B-doped SiNW. In FIG. 11A, curves 1, 2, 3, 4, 5, and 6 correspond to temperatures of 295, 250, 200, 150, 100, and 50 K, respectively. FIG. 11B shows I-V data recorded on the nanowire at 4.2 K.

Diameter Selective Synthesis of Semiconductor Nanowires

Nearly monodisperse samples of single crystalline GaP nanowires have been synthesized with diameters of 10, 20, and 30 nm and lengths greater than 10 μm by exploiting well-defined gold colloids as catalysts in our laser catalytic growth (LCG) process. In this method, the Ga and P reactants generated by laser ablation of solid GaP are subsequently directed into a nanowire structure by gold nanocluster catalysts. Transmission electron microscopy (TEM) studies of nanowires prepared in this way demonstrate that the distributions of nanowire diameters are defined by those of the nanocluster catalysts. High-resolution TEM shows that the wires are a single crystal zinc blend with a [111] growth direction, and energy dispersive X-ray analysis confirms that the nanowire composition is stoichiometric GaP. The use of monodisperse nanocluster catalysts combined with the LCG method will enable the growth of a wide range of semiconductor nanowires with well-defined and controlled diameters, and thus opens up opportunities from fundamental properties of one-dimensional (1D) systems to the assembly of functional nanodevices.

Nearly monodisperse samples of single crystalline GaP nanowires have been synthesized with diameters of 10, 20, and 30 nm and lengths greater than 10 μm by exploiting well-defined gold colloids as catalysts in our laser catalytic growth (LCG) synthetic methodology. Transmission electron microscopy (TEM) studies of nanowires prepared in this way demonstrate that the distributions of nanowire diameters are defined by those of the nanocluster catalysts. High-resolution TEM shows that the wires are a single crystal zinc blende with a [111] growth direction, and energy dispersive X-ray analysis (EDAX) confirms that the nanowire composition is stoichiometric GaP.

Recent interest in low-dimensional semiconductor materials has been motivated by the push for miniaturization of electronic and optoelectronic devices and a need to understand the fundamentals of nanoscale chemistry and physics. In particular, one-dimensional (1D) systems are exciting from both fundamental and applied viewpoints. Fascinating physical phenomena, such as Luttinger liquid behavior, and numerous applications from interconnects to scanning probe microscopies, require high-quality, well-defined 1D nanostructures. Experimental progress in the field of 1D nanostructures has often been limited by the ability to create new materials in this size regime with controlled size, structure, and composition.

Early approaches to 1D nanostructure synthesis employed thin film growth and lithographic techniques. In particular, "T-wires" have been fabricated by growing semiconductor quantum wells via molecular beam epitaxy, followed by cleavage and overgrowth on the cleaved surface, while "V-groove" nanowires have been prepared by etching trenches on a surface and then depositing a small amount of material into the resulting grooves. One of the significant limitations of these approaches is that the nanowires are embedded in a substrate, which precludes the assembly of complex 2D and 3D nanostructures. Template approaches have also been used for growing a wide-range of nanowires. These methods can provide good control over the length and diameter of nanowires, although they are limited in that polycrystalline structures are often produced.

Figure 12:
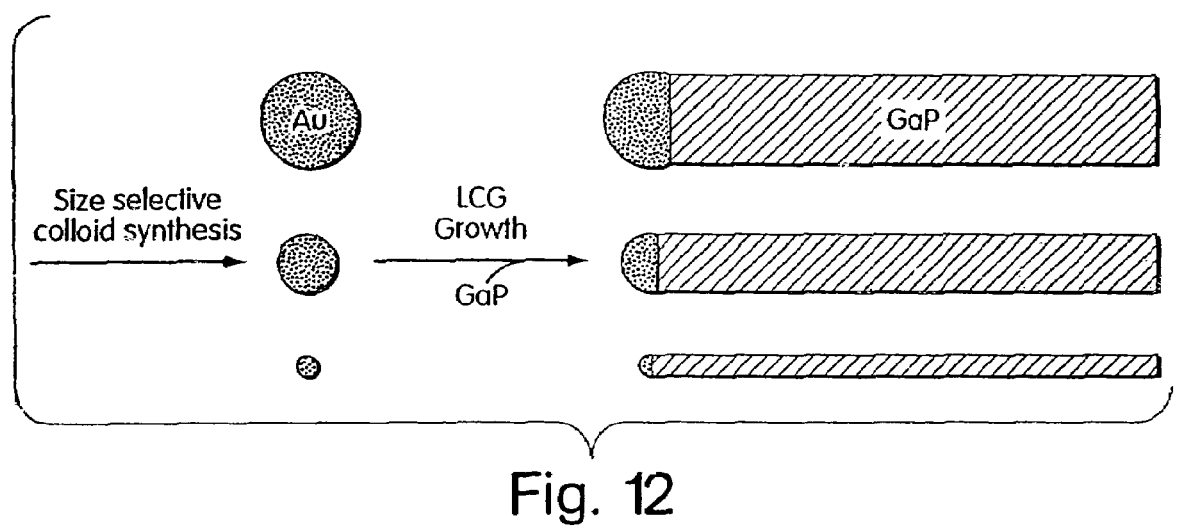
FIG. 12 is a schematic diagram that depicts the use of monodispersed gold colloids as catalysts for the growth of well-defined GaP semiconductor nanowires.

Our laboratory has made significant progress toward the development of a general synthetic approach to free-standing single-crystal semiconductor nanowires via the LCG method. In LCG, laser ablation of a solid target is used to simultaneously generate nanoscale metal catalyst clusters and reactive semiconductor atoms that produce nanowires via a vapor-liquid-solid growth mechanism. This method has been used to produce a wide range of group IV, III-V, and II-VI nanowires. We have suggested that the size of the catalyst nanocluster determines the size of the wire during growth, and thus one can envision creating wires with a narrow size distribution by exploiting monodisperse catalyst nanoclusters (FIG. 12). Here we utilize nanometer diameter gold colloids to explore this approach.

Figure 13A:
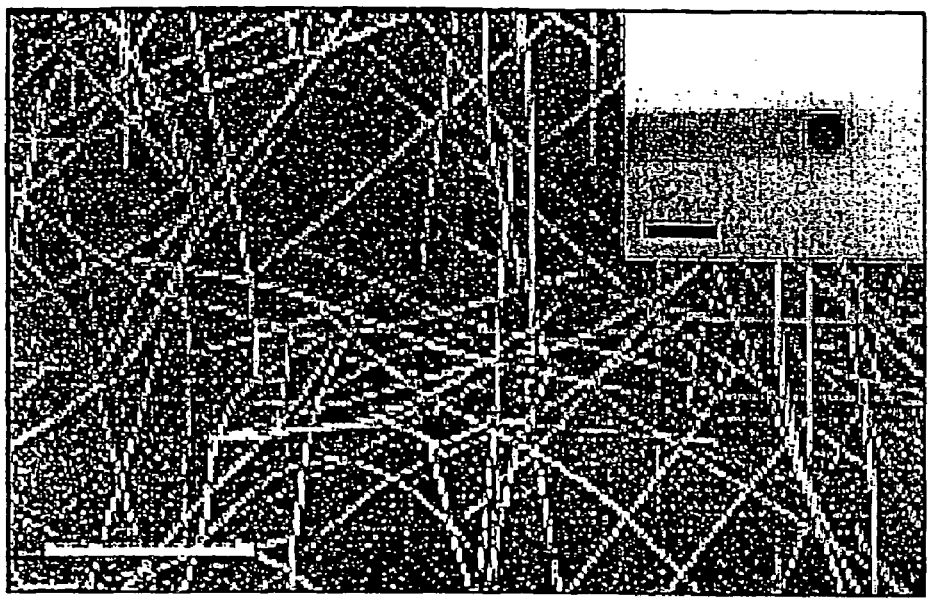
FIG. 13A shows a FE-SEM image of nanowires synthesized from 28.2 nanometer colloids.

GaP nanowires were grown by LCG using 8.4, 18.5, and 28.2 nm diameter gold colloids. In these experiments the catalyst nanoclusters are supported on a $SiO_2$ substrate and laser ablation is used to generate the Ga and P reactants from a solid target of GaP. Field emission scanning electron microscopy (FESEM) demonstrates that nanowires with lengths exceeding 10 μm (FIG. 13A) were obtained using all three sizes of catalyst. Examination of the nanowire ends also shows the presence of the nanocluster catalyst (FIG. 13A, inset). Control experiments carried out without the Au colloids did not produce nanowires. The FESEM images show that the nanowire diameter distributions are narrower than obtained in experiments without the colloid catalysts, although FESEM is not a good method for quantifying these distributions since small variations in the focal plane can produce significant changes in the observed diameter.

The growth apparatus used in these experiments is similar to that reported. Substrates were made by placing a silicon wafer with 600 nm of thermal oxide (Silicon Sense) into a solution of 95:5 EtOH:$H_2O$ with 0.4% N-[3-(Trimethoxysilyl)propyl]-ethylenediamine for 5 minutes, followed by curing at 100-110° C. for 10 minutes. Solutions of Au colloids (Ted Pella) were diluted to concentrations of $10^9$-$10^{11}$ particles/mL to minimize aggregation and were deposited on the substrates. Substrates were placed in a quartz tube at the downstream end of the furnace with a solid target of GaP placed 3-4 cm outside of the furnace at the upstream end. The chamber was evacuated to less than 100 mTorr, and then maintained at 250 Torr with an Airflow of 100 sccm. The furnace was heated to 700° C. and the target was ablated for 10 minutes with an ArF excimer laser ($\lambda$=193 nm, 100 mJ/pulse, 10 Hz). After cooling, the substrates were examined by FESEM (LEO 982). For TEM (JEOL 200CX and 2010) and EDAX analysis, nanowires were deposited onto copper grids after removal from the substrates by sonication in ethanol.

To obtain a quantitative measure of the nanowire diameter distributions produced using the gold colloids, and to better characterize their structure and composition, we used TEM. High resolution TEM shows that the wires are single crystal (FIG. 13B), growing in the [111] direction, and EDAX confirms the composition to be stoichiometric GaP (Ga:P 1.00: 0.94), within the limits of this technique. Significantly, extensive TEM analysis of nanowire diameters demonstrates the extremely good correlation with the colloid catalyst diameters and dispersion (FIGS. 14A and 14B); that is, for wires grown from 28.2±2.6, 18.5±0.9, and 8.4±0.9 nm colloids we observe mean diameters of 30.2±2.3, 20.0±1.0, and 11.4±1.9 nm, respectively. The mean nanowire diameter is generally 1-2 nm larger than that of the colloids. We believe that this increase is due to alloying of the Ga and P reactants with the colloids before nucleation of the nanowire occurs. For the 30 nm and 20 nm wires (FIGS. 14A and 14B) it is clear that the width of the nanowire distributions mirrors those of the colloid, suggesting that the monodispersity of the wires is limited only by the dispersity of the colloids. For the 10 nm diameter wires (FIG. 14C), a small broadening (1 nm) of the wire distribution can be attributed to aggregation of the colloids. The mean diameter and distribution width increased as more concentrated solutions of the colloid were dispersed onto the substrate. The fact that the distribution has peaks separated by ~2.5 nm suggests that some of the wires grow from aggregates of two colloids, although additional work is required to substantiate this point. In all cases, the distribution of wire diameters is more than an order of magnitude narrower than those grown without the use of colloid catalyst (FIG. 14D): 43±24 nm.

We believe that this work demonstrates clearly for the first time an ability to exert systematic control over the diameter of semiconductor nanowires for a variety of colloids. Previous attempts to grow nanowires on surfaces with poorly defined catalysts resulted in nanowires with non-uniform diameters greater than 50 nm. Other attempts to control the diameter of nanowires by varying the background carrier gas merely shifted the mean diameter of the wires slightly and yielded much broader distributions of wires than we have achieved with colloid-mediated growth.

In summary, we have demonstrated the controlled synthesis of semiconductor wires with monodisperse diameter distributions. These high-quality, single crystalline wires represent good candidates for both further studies of low-dimensional physics as well as for applications in various fields of nanoscale science and technology. In particular, we believe that the synthesis of controlled diameter samples will greatly facilitate the assembly of these nanoscale building blocks into complex and functional 2D and 3D nanosystems.

FIG. 12 is a schematic depicting the use of monodisperse gold colloids as catalysts for the growth of well-defined GaP semiconductor nanowires.

Figure 13B:
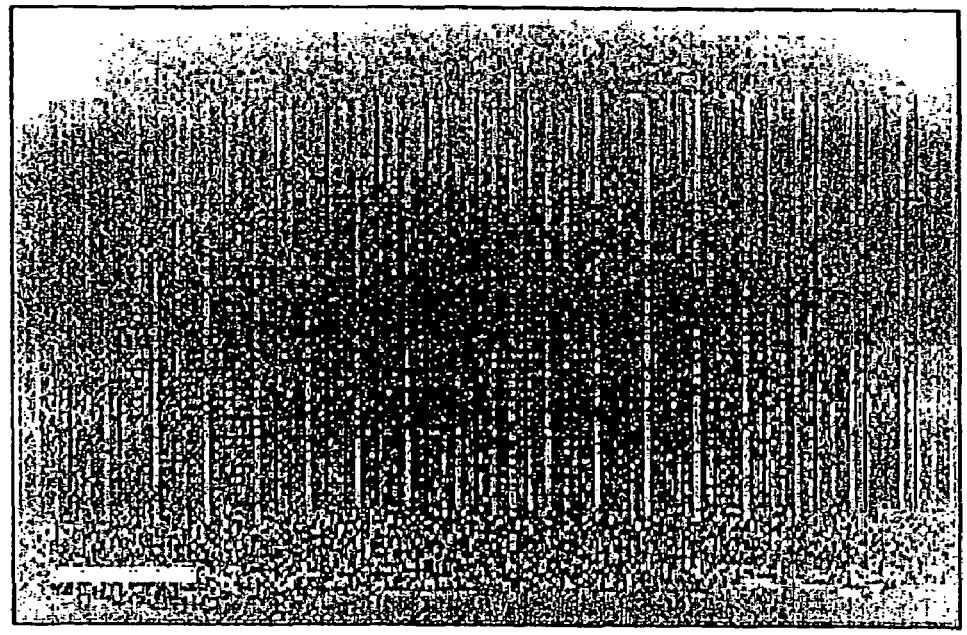
FIG. 13B shows a TEM image of another wire in the sample.

FIG. 13A shows a FESEM image of nanowires synthesized from 28.2 nm colloids (scale bar is 5 μm). The inset is a TEM image of the end of one of these wires (scale bar is 50 nm). The high contrast feature corresponds to the colloid catalyst at the end of the wire. FIG. 13B shows a TEM image of another wire in this sample (scale bar is 10 nm). The [111] lattice planes are resolved, showing that wire growth occurs along this axis, in agreement with earlier work. Measurement of the inter-plane spacing gives a lattice constant of 0.54 nm (±0.05 nm) for the wire, in agreement with the bulk value for GaP, 0.5451 nm.

Figure 14A:
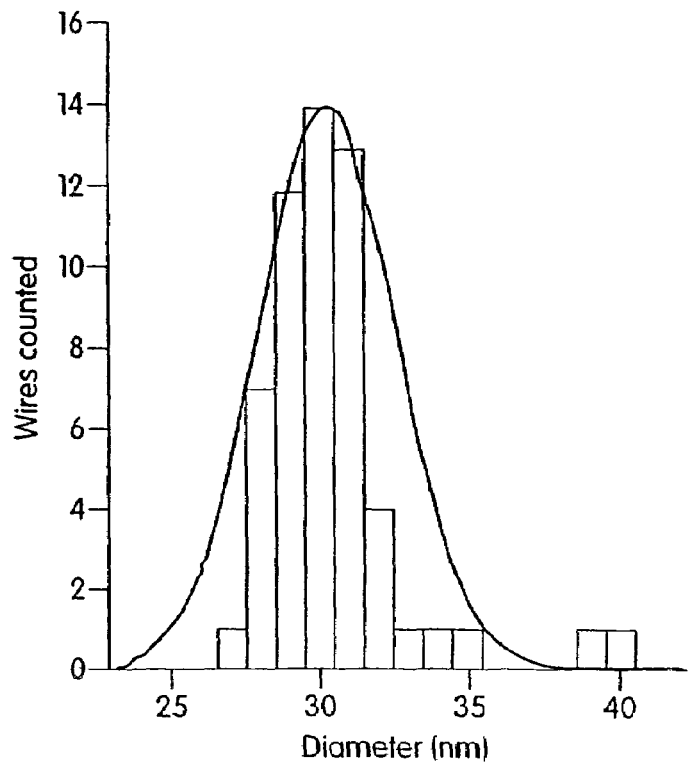
FIGS. 14A-14C show histograms of measured diameters for wires grown from different diameter colloids.
Figure 14B:
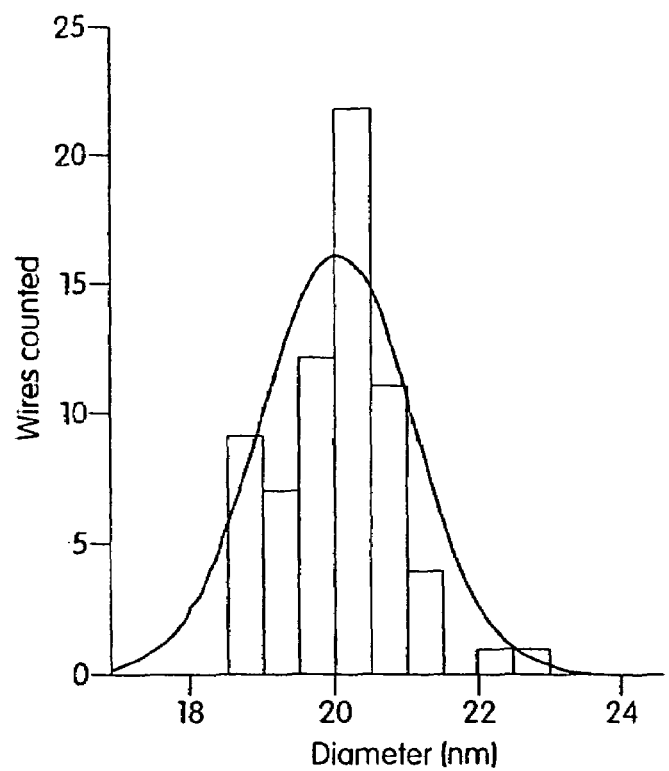
Figure 14C:
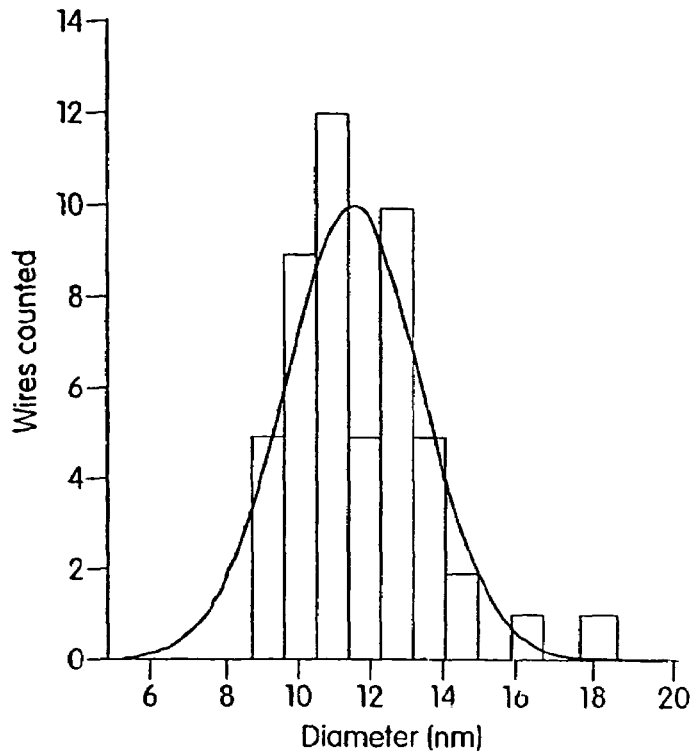
Figure 14D:
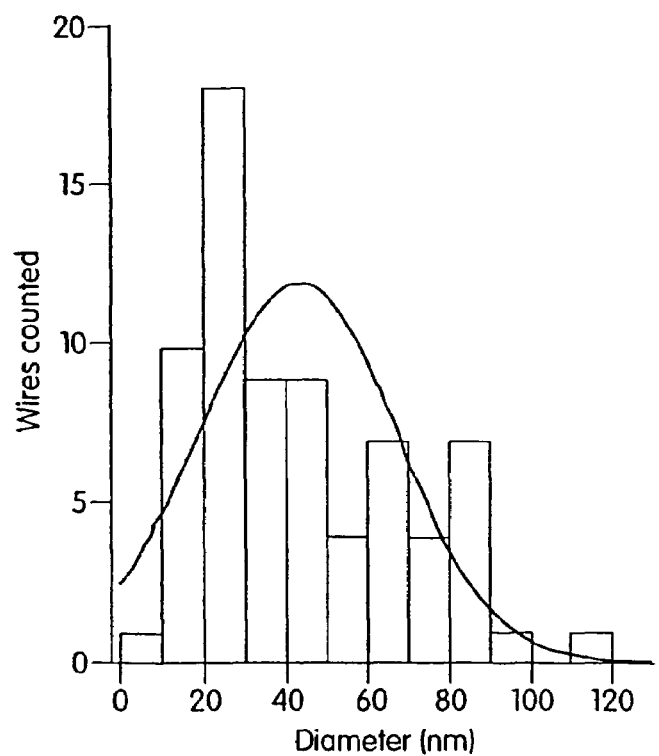
FIG. 14D shows a histogram of diameters for wires grown using the previous method without colloids, in which the laser is used to both generate the gold nanoclusters and the GaP reactants.

FIGS. 14A-14C show histograms of measured diameters for wires grown from 28.2 nm (FIG. 14A), 18.5 nm (FIG. 14B), and 8.4 nm (FIG. 14C) colloids. The solid line shows the distribution of wire. FIG. 14D shows a histogram of diameters for wires grown using the previous method without colloids, in which the laser is used to both generate the Au nanoclusters and the GaP reactants. The distribution is very broad (stan. dev. 23.9 nm) and the mean diameter (42.7 nm) greater than those synthesized using the predefined colloid catalyst. In all cases, the reported nanowire diameters correspond to the crystalline cores. The amorphous oxide layers on the surface of all nanowires are relatively uniform from wire to wire within the same experiment, but vary from 2-6 nm in thickness between syntheses.

General Synthesis of Compound Semiconductor Nanowires

The predictable synthesis of a broad range of multicomponent semiconductor nanowires has been accomplished using laser-assisted catalytic growth. Nanowires of binary group III-V materials (GaAs, GaP, InAs and InP), ternary III-V materials (GaAs/P, InAs/P), binary II-VI compounds (ZnS, ZnSe, CdS, and CdSe) and binary SiGe alloys have been prepared in bulk quantities as high purity (>90%) single crystals. The nanowires have diameters varying from three to tens of nanometers, and lengths extending to tens of micrometers. The synthesis of this wide range of technologically important semiconductor nanowires can be extended to many other materials and opens up significant opportunities in nanoscale science and technology.

The synthesis of nanoscale materials is critical to work directed towards understanding fundamental properties of small structures, creating nanostructured materials and developing nanotechnologies. Nanowires and nanotubes have been the focus of considerable attention, because they have the potential to answer fundamental questions about one-dimensional systems and are expected to play a central role in applications ranging from molecular electronics to novel scanning microscopy probes. To explore such diverse and exciting opportunities requires nanowire materials for which the chemical composition and diameter can be varied. Over the past several years considerable effort has been placed on the bulk synthesis of nanowires, and while advances have been made using template, laser ablation, solution, and other methods, in no case has it been demonstrated that one approach could be exploited in a predictive manner to synthesize a wide range of nanowire materials. Here we describe the predictable synthesis of a broad range of binary and ternary III-V, II-VI and IV-IV group semiconductor nanowires using a laser-assisted catalytic growth (LCG) method.

Recently, we reported the growth of elemental Si and Ge nanowires using the LCG method, which exploits laser ablation to generate nanometer diameter catalytic clusters that define the size and direct the growth of the crystalline nanowires by a vapor-liquid-solid (VLS) mechanism. A key feature of the VLS growth process and our LCG method is that equilibrium phase diagrams can be used to predict catalysts and growth conditions, and thereby enable rational synthesis of new nanowire materials. Significantly, we show here that semiconductor nanowires of the III-V materials GaAs, GaP, GaAsP, InAs, InP and InAsP, the II-VI materials ZnS, ZnSe, CdS and CdSe, and IV-IV alloys of SiGe can be synthesized in high yield and purity using this approach. Compound semiconductors, such as GaAs and CdSe, are especially intriguing targets since their direct band gaps give rise to attractive optical and electrooptical properties. The nanowires have been prepared as single crystals with diameters as small as 3 nm, which places them in a regime of strong radial quantum confinement, and lengths exceeding 10 μm. These studies demonstrate that LCG represents a very general and predictive approach for nanowire synthesis, and moreover, we believe that the broad-range of III-V, II-VI and IV-IV nanowires prepared will open up many new opportunities in nanoscale research and technology.

Figure 15:
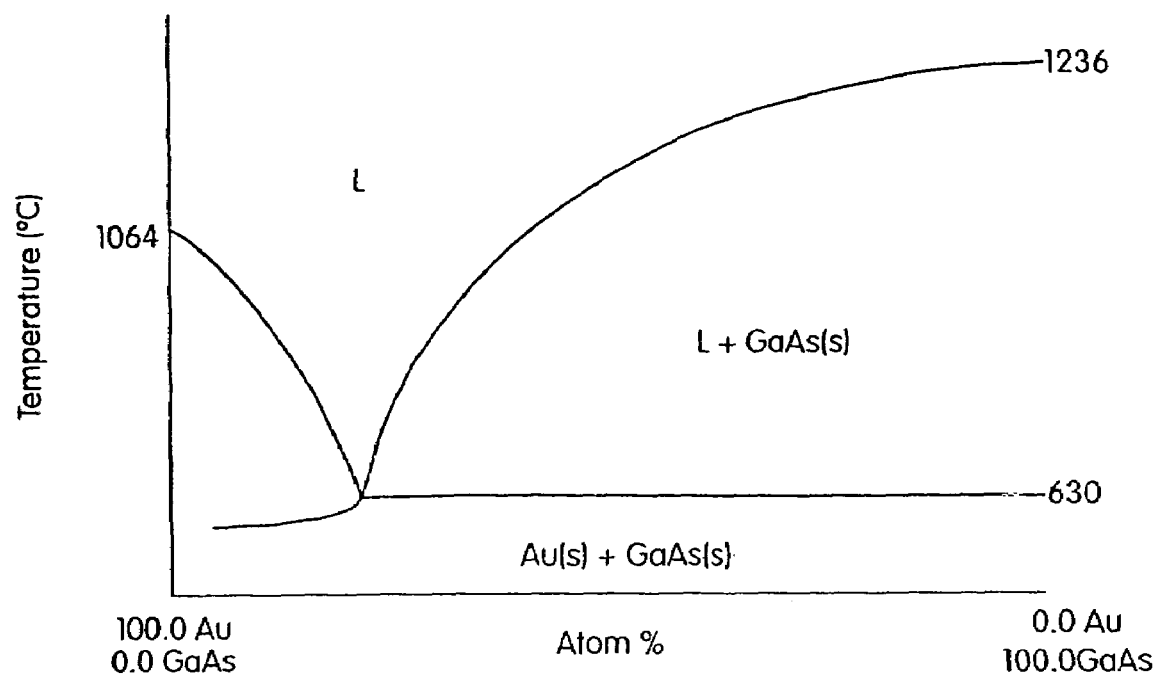
FIG. 15 shows a pseudobinary phase diagram for gold and gallium arsenide.

The prediction of growth conditions for binary and more complex nanowires using the LCG method is, in principle, significantly more difficult than previous studies of elemental Si and Ge nanowires due to the complexity of ternary and higher order phase diagrams. However, this complexity can be greatly reduced by considering pseudobinary phase diagrams for the catalyst and compound semiconductor of interest. For example, the pseudobinary phase diagram of Au—GaAs shows that Au—Ga—As liquid and GaAs solid are the principle phases above 630° C. in the GaAs rich region (FIG. 15). This implies that Au can serve as a catalyst to grow GaAs nanowires by the LCG method, if the target composition and growth temperature are set to this region of the phase diagram. Indeed, we find that LCG using $(GaAs)_{0.95}Au_{0.05}$ targets produces samples consisting primarily of nanowires. A typical field-emission scanning electron microscopy (FE-SEM) image of material prepared at 890° C. (FIG. 16A) shows that the product is wire-like with lengths extending to 10 μm or more. Analyses of these high-resolution SEM images shows that at least 90% of the product produced by the LCG method is nanowire with only a small amount of particle material. X-ray diffraction data from bulk samples can be indexed to the zinc-blende (ZB) structure with a lattice constant consistent with bulk GaAs, and also show that the material is pure GaAs to the 1% level. Lastly, we note that high yields of GaAs nanowires were also obtained using Ag and Cu catalysts. These data are consistent with the fact that these metals (M=Ag, Cu) exhibit M—Ga—As liquid and GaAs solid phase in the GaAs rich regions of the psuedobinary phase diagrams, and furthermore, demonstrate the predictability of the LCG approach to nanowire growth.

The structure and composition of the GaAs nanowires have been characterized in detail using transmission electron microscopy (TEM), convergent beam electron diffraction (ED) and energy dispersive X-ray fluorescence (EDX). TEM studies show that the nanowires have diameters ranging from 3 nm to ca 30 nm. A typical diffraction contrast image of a single 20 nm diameter wire (FIG. 17A) indicates that the wire is single crystal (uniform contrast) and uniform in diameter. The Ga:As composition of this wire determined by EDX, 51.4:48.6, is the same, within limits of instrument sensitivity, as the composition obtained from analysis of a GaAs crystal standard. Moreover, the ED pattern recorded perpendicular to the long axis of this nanowire (inset, FIG. 17A) can be indexed for the <112> zone axis of the ZB GaAs structure, and thus shows that growth occurs along the [111] direction. Extensive measurements of individual GaAs nanowires show that growth occurs along the <111> directions in all cases. This direction and the single crystal structure are further confirmed by lattice resolved TEM images (e.g., FIG. 17B) that show clearly the (111) lattice planes (spacing 0.32+/−0.01 nm; bulk GaAs, 0.326 nm) perpendicular to the wire axis. Lastly, the TEM studies reveal that most nanowires terminate at one end with a nanoparticle (inset, FIG. 16A). EDX analysis indicates that the nanoparticles are composed mainly of Au. The presence of Au nanoparticles at the ends of the nanowires is consistent with the pseudobinary phase diagram, and represents strong evidence for a VLS growth mechanism proposed for LCG.

The successful synthesis of binary GaAs nanowires by LCG is not an isolated case but general to a broad range of binary and more complex nanowire materials (Table-1). To extend our synthetic approach to the broadest range of nanowires, we recognize that catalysts for LCG can be chosen in the absence of detailed phase diagrams by identifying metals in which the nanowire component elements are soluble in the liquid phase but that do not form solid compounds more stable than the desired nanowire phase; that is, the ideal metal catalyst should be physically active but chemically stable. From this perspective the noble metal Au should represent a good starting point for many materials. This noble metal also has been used in the past for the VLS growth of surface supported nanowires by metal-organic chemical vapor deposition (MOCVD). The nanowires produced by MOCVD method are distinct from the materials reported in this communication in several regards, including (1) the MOCVD nanowires are produced on surfaces and not in the bulk quantities required for assembly, (2) the MOCVD nanowires taper significantly from the base to their ends (that is, they do not have uniform diameters), and (3) the smallest nanowire diameters, 10-15 nm, are significantly larger than the 3-5 nm diameters achieved in our work. Lastly, as described below, it is important to recognize that our LCG method is readily extended to many different materials (e.g., Table-1) simply by producing solid targets of the material of interest and catalyst.

First, we have extended significantly our work on GaAs to include GaP and ternary alloys $GaAs_{1-x}P_x$. FE-SEM images of the product obtained by LCG from $(GaP)_{0.95}Au_{0.05}$ targets exhibit high purity nanowires with lengths exceeding 10 μm (FIG. 16B). Extensive TEM characterization shows that these nanowires (i) are single crystal GaP, (ii) grow along the <111> directions, and (iii) terminate in Au nanoparticles (inset, FIG. 16B) as expected for the LCG mechanism. We have further tested the limits of our LCG approach through studies of ternary GaAsP alloy nanowires. The synthesis of ternary III-V alloys is of particular interest for band gap engineering that is critical for electronic and optical devices. LCG of GaAsP nanowires using a $GaAs_{0.6}P_{0.4}$ target with a Au catalyst yielded nearly pure nanowires (FIG. 16C). TEM images, ED and EDX show that these nanowires are single crystals, grow along the <111> directions, have a Ga:As:P ratio, 1.0: 0.58:0.41, that is essentially the same as the starting target composition, and terminate in nanoclusters that are composed primarily of Au (inset, FIG. 16C). High-resolution TEM images recorded on nanowires with diameters of ca. 10 and 6 nm (FIGS. 17C and 17D) show well-ordered (111) lattice planes and no evidence for compositional modulation. We believe the observation that the ternary nanowire composition can be controlled by target composition is especially important, because it provides an opportunity to explore exciton energy changes due to both band-gap variations (composition) and quantum confinement (size).

Figure 18A:
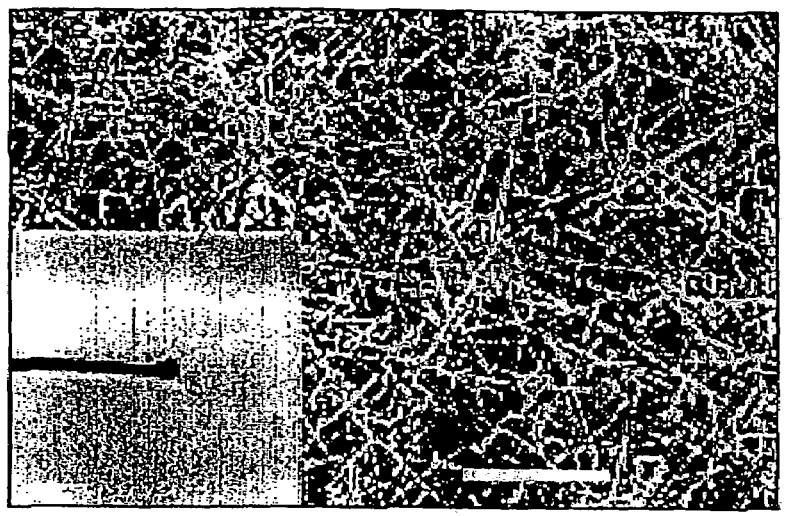
FIG. 18A shows a FE-SEM image of CdSe nanowires prepared by laser assisted catalytic growth.

Based on the above results, it is perhaps not surprising that we have also successfully used LCG to prepare III-V binary and ternary materials containing In—As—P (Table-1). We believe that a more significant point is that this synthetic approach can also be easily extended to the preparation of many other classes of nanowires, including the II-VI materials ZnS, ZnSe, CdS and CdSe (Table-1), IV-IV SiGe alloys. The cases of the II-VI nanowires CdS and CdSe are especially important, because a stable structural phase of these materials, wurtzite (W), is distinct from the ZB structure of the III-V materials described above and the ZB structure of ZnS and ZnSe. Significantly, we find that nanowires of CdS and CdSe can be synthesized in high yield using the LCG approach with a Au catalyst (FIG. 18A). TEM and ED data obtained on individual CdSe nanowires (for example, FIGS. 18B and 18C) demonstrate that these materials are single crystals with a W-type structure and <110> growth direction that is clearly distinguished from the <111> direction of ZB structures. Studies of CdS nanowires (Table-1) show somewhat more complex behavior; that is, W-type nanowires with growth along two distinct <100> and <002> directions. It is possible that the <002> direction assigned for a minority of CdS nanowires could correspond to the <111> direction of a ZB structure. However, X-ray diffraction measurements made on bulk nanowire samples are consistent with the W assignment. In addition, previous studies of W-type CdS and CdSe nanoclusters showed elongation along the <002> direction. We believe that systematic studies of nanowire structure as a function of growth temperature should help to elucidate the origin of these results for CdS, and could also provide insight into how nanowire growth direction might be controlled.

Lastly, we have used LCG to prepare nanowires of IV-IV binary Si—Ge alloys (Table-1). Using a Au catalyst, it was possible to synthesize single crystal nanowires over the entire $Si_{1-x}Ge_x$ composition range. Unlike the case of GaAsP discussed above, the Si—Ge alloys do not exhibit the same compositions as the starting targets. Rather, the composition varies continuously within the growth reactor with Si rich materials produced in the hotter central region and Ge rich materials produced at the cooler end. Specifically, LCG growth from a $(Si_{0.70}Ge_{0.30})_{0.95}Au_{0.05}$ target at 1150° C. produced nanowires with a Si:Ge ratio of 95:5, 81:19, 74:26, 34:66 and 13:87 from the furnace center to end, respectively. This composition variation arises from the fact that the optimal growth temperatures of the two individual nanowire materials are quite different. Such differences can increase the difficulty in synthesizing controlled composition alloys, although our results also show that this can be exploited to prepare a range of alloy compositions in a single growth experiment.

In conclusion, we have synthesized a wide-range of single crystal binary and ternary compound semiconductor nanowires using our LCG technique. We believe that these results demonstrate clearly the generality of this approach for rational nanowire synthesis. The availability of these high-quality, single crystal semiconductor nanowires is expected to enable fascinating opportunities in nanometer scale science and technology.

For example, these nanowires can be used to probe the confinement, dynamics and transport of excitons in 1D, and can serve as optically-active building blocks for nanostructured materials. Moreover, by further controlling growth, we believe that our LCG approach can be used to synthesize more complex nanowire structures, including single wire homo- and heterojunctions and superlattices, and thus may enable the synthesis of nanoscale light-emitting diodes and laser devices.

The apparatus and general procedures for LCG growth of nanowires have been described previously. The targets used in syntheses consisted of $(material)_{0.95}Au_{0.05}$. Typical conditions used for synthesis were (i) 100-500 torr $Ar:H_2$ (95:5), (ii) 50-150 sscm gas flow, and (iii) ablation with a pulsed Nd:YAG laser (λ=1064 nm; 10 Hz pulse rate; 2.5 W average power). Specific temperatures used for the growth of different nanowire materials are given in Table-1. The nanowire products were collected at the down-stream cold end of the furnace.

The nanowire samples were characterized using X-ray diffraction (SCINTAG XDS 2000), FE-SEM (LEO 982), and TEM (Philips 420 and JEOL 2010). Electron diffraction and composition analysis (EDX) measurements were also made on the TEMs. Samples for TEM analysis were prepared as follows: samples were briefly sonicated in ethanol, which suspended the nanowire material, and then a drop of suspension was placed on a TEM grid and allowed to dry.

Template mediated methods using membranes and nanotubes have been used to prepare a number of materials. However, these nanowires typically have diameters >10 nm, which are larger than those desired for strong quantum confinement effects, and often have polycrystalline structures that make it difficult to probe intrinsic physical properties.

Table 1 is a summary of single crystal nanowires synthesized. The growth temperatures correspond to ranges explored in these studies. The minimum (Min.) and average (Ave.) nanowire diameters (Diam.) were determined from TEM and FE-SEM images. Structures were determined using electron diffraction and lattice resolved TEM imaging: ZB, zinc blende; W, wurtzite; and D, diamond structure types.

Compositions were determined from EDX measurements made on individual nanowires. All of the nanowires were synthesized using Au as the catalyst, except GaAs, for which Ag and Cu were also used. The GaAs nanowires obtained with Ag and Cu catalysts have the same size, structure and composition as those obtained with the Au catalyst.

nanowire exhibiting well-resolved (100) lattice planes. The experimental lattice spacing, 0.36±0.01 nm is consistent with the 0.372 nm separation in bulk crystals. The 30° orientation (100) lattice planes with respect to the nanowire axis is consistent with the [110] growth direction determined by ED. The scale bar corresponds to 5 nm.

| Material | Growth Temp. (° C.) | Min. Diam. (nm) | Ave. Diam. (nm) | Structure | Growth Direction | Ratio of Components |
|---|---|---|---|---|---|---|
| GaAs | 800-1030 | 3 | 19 | ZB | <111> | 1.00:0.97 |
| GaP | 870-900 | 3-5 | 26 | ZB | <111> | 1.00:0.98 |
| GaAs$_{0.6}$P$_{0.4}$ | 800-900 | 4 | 18 | ZB | <111> | 1.00:0.58:0.41 |
| InP | 790-830 | 3-5 | 25 | ZB | <111> | 1.00:0.98 |
| InAs | 700-800 | 3-5 | 11 | ZB | <111> | 1.00:1.19 |
| InAs$_{0.5}$P$_{0.5}$ | 780-900 | 3-5 | 20 | ZB | <111> | 1.00:0.51:0.51 |
| ZnS | 990-1050 | 4-6 | 30 | ZB | <111> | 1.00:1.08 |
| ZnSe | 900-950 | 3-5 | 19 | ZB | <111> | 1.00:1.01 |
| CdS | 790-870 | 3-5 | 20 | W | <100>, <002> | 1.00:1.04 |
| CdSe | 680-1000 | 3-5 | 16 | W | <110> | 1.00:0.99 |
| Si$_{1-x}$Ge$_x$ | 820-1150 | 3-5 | 18 | D | <111> | Si$_{1-x}$Ge$_x$ |

FIG. 15 shows a pseudobinary phase diagram for Au and GaAs. The liquid Au—Ga—As component is designated by L.

Figure 16A:
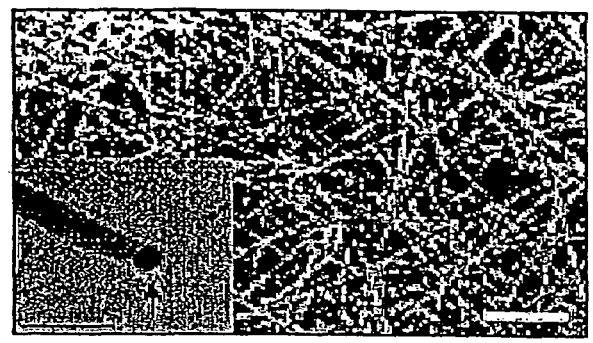
FIGS. 16A-16C show FE-SEM images of different nanowires prepared by laser assisted catalytic growth.
Figure 16B:
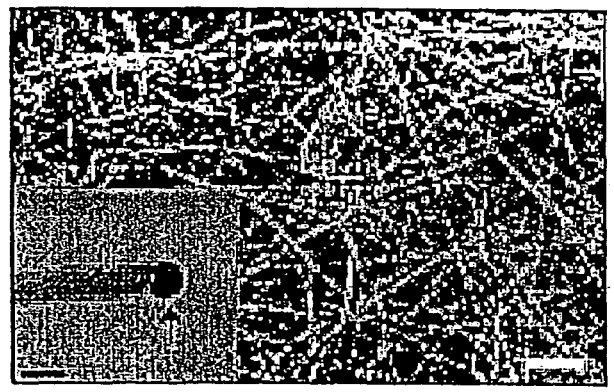
Figure 16C:
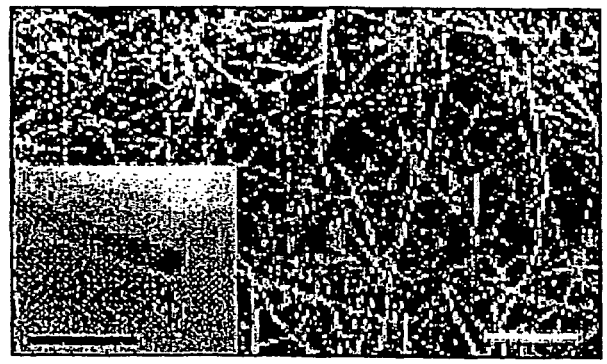

FIGS. 16A-16C show FE-SEM images of GaAs (FIG. 16A), GaP (FIG. 16B) and GaAs$_{0.6}$P$_{0.4}$ (FIG. 16C) nanowires prepared by LCG. The scale bars in FIGS. 16A-16C are 2 μm. The insets in FIGS. 16A-16C are TEM images of GaAs, GaP and GaAs$_{0.6}$P$_{0.4}$ nanowires, respectively. The scale bars in are all 50 nm. The high contrast (dark) features correspond to the solidified nanocluster catalysts.

Figure 17A:
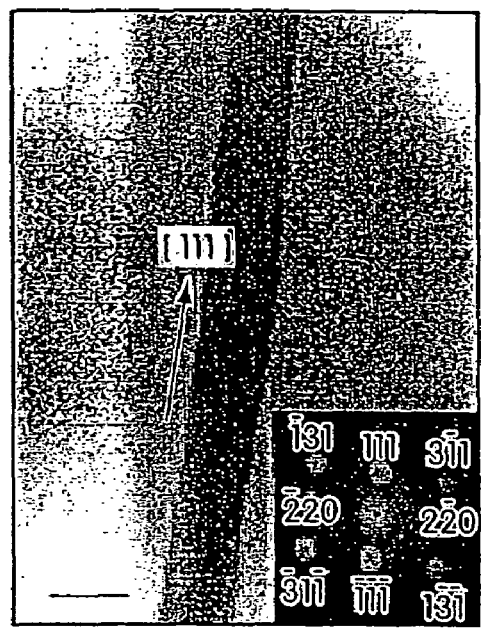
FIG. 17A shows a diffraction contrast TEM image of an approximately 20 nanometer diameter gallium arsenide nanowire.
Figure 17B:
FIGS. 17B-17D show high resolution TEM images of different diameter nanowires.
Figure 17C:
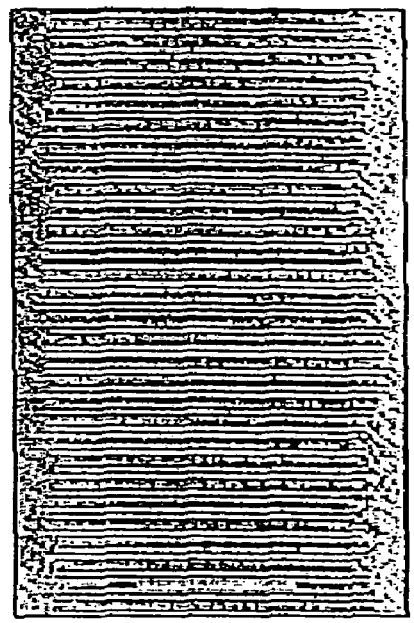
Figure 17D:
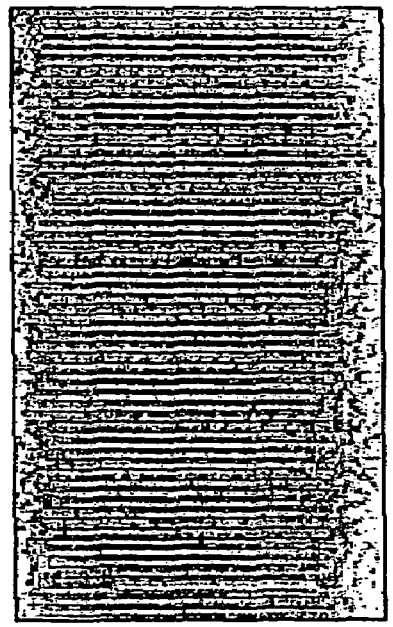

FIG. 17A shows a diffraction contrast TEM image of a ca. 20 nm diameter GaAs nanowire. The inset shows a convergent beam electron diffraction pattern (ED) recorded along the <112> zone axis. The [111] direction of the ED pattern is parallel to the wire axis, and thus shows that growth occurs along the [111] direction. The scale bar corresponds to 20 nm. FIG. 17B shows a high-resolution TEM image of a ca. 20 nm diameter GaAs nanowire. The lattice spacing perpendicular to the nanowire axis, 0.32±0.01 nm, is in good agreement with the 0.326 nm spacing of (111) planes in bulk GaAs. The scale bar corresponds to 10 nm. FIGS. 17C and 17D show high-resolution TEM images of 10 and 6 nm diameter, respectively, GaAs$_{0.6}$P$_{0.4}$ nanowires. The (111) lattice planes (perpendicular to the wire axes) are clearly resolved in all three nanowires. The scale bars in FIGS. 17C and 17D are 5 nm.

Figure 18B:
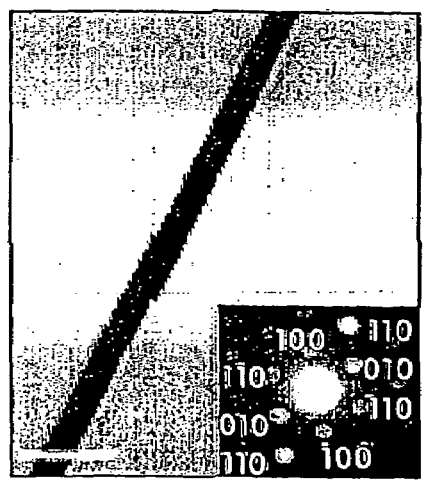
FIG. 18B shows a diffraction contrast TEM image of an 18 nanometer diameter CdSe nanowire.
Figure 18C:
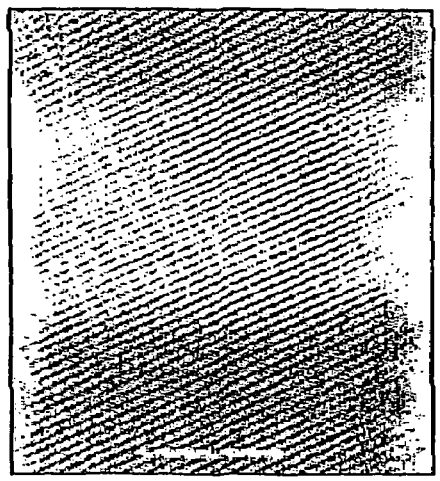
FIG. 18C shows a high resolution TEM image of an approximately 13 nanometer diameter CdSe nanowire.

FIG. 18A shows a FE-SEM image of CdSe nanowires prepared by LCG. The scale bar corresponds to 2 μm. The inset in FIG. 18A is a TEM image of an individual CdSe nanowire exhibiting nanocluster (dark feature) at the wire end. EDX shows that the nanocluster is composed primarily of Au. The scale bar is 50 nm. FIG. 18B shows a diffraction contrast TEM image of a 18 nm diameter CdSe nanowire. The uniform contrast indicates that the nanowire is single crystal. The inset in FIG. 18B is an ED pattern, which has been indexed to the wurtzite structure, recorded along the <001> zone axis. The [110] direction of the ED pattern is parallel to the wire axis, and thus shows that growth occurs along the [110] direction. The scale bar is 50 nm. FIG. 18C shows a high-resolution TEM image of a ca. 13 nm diameter CdSe Laser-Assisted Catalytic Growth of Single Crystal GaN Nanowires Single crystalline GaN nanowires have been synthesized in bulk quantities using laser-assisted catalytic growth (LCG). Laser ablation of a (GaN, Fe) composite target generates liquid nanoclusters that serve as catalytic sites confining and directing the growth of crystalline nanowires. Field emission scanning electron microscopy shows that the product primarily consists of wire-like structures, with diameters on the order of 10 nm, and lengths greatly exceeding 1 μm. Powder X-ray diffraction analyses of bulk nanowire samples can be indexed to the GaN wurtzite structure, and indicate >95% phase purity. Transmission electron microscopy, convergent beam electron diffraction, and energy dispersive X-ray fluorescence analyses of individual nanowires show that they are GaN single crystals with a [100] growth direction. The synthesis of bulk quantities of single crystal nanowires of GaN and other technologically important semiconducting nitride materials should open up many opportunities for further fundamental studies and applications.

Herein we report the bulk synthesis of single crystalline GaN nanowires. Laser ablation of a composite target of GaN and a catalytic metal generates liquid nanoclusters that serve as reactive sites confining and directing the growth of crystalline nanowires. Field emission scanning electron microscopy (FE-SEM) shows that the product primarily consists of wire-like structures. Powder X-ray diffraction (PXRD) analyses of bulk nanowire sample can be indexed to the GaN wurtzite structure, and indicate >95% phase purity. Transmission electron microscopy (TEM), convergent beam electron diffraction (CBED), and energy dispersive X-ray fluorescence (EDX) analyses of individual nanowires show that they are GaN single crystals with a [100] growth direction.

Nanostructured GaN materials have attracted extensive interest over the past decade due to their significant potential for optoelectronics. These studies have primarily focused on zero dimensional (0D) quantum dots and two dimensional (2D) quantum well structures, which can be readily synthesized using established methods. Investigations of one dimensional (1D) GaN nanowires, which could enable unique opportunities in fundamental and applied research, have been limited due to difficulties associated with their synthesis. Specifically, there has been only one report of GaN nanowire growth. In this work, carbon nanotubes were used as templates in the presence of Ga-oxide and $NH_3$ vapor to yield GaN nanowires. We have exploited predictable synthetic approach for GaN nanowire growth called laser-assisted catalytic growth (LCG). In this method, a pulsed laser is used to vaporize a solid target containing desired material and a catalyst, and the resulting liquid nanoclusters formed at elevated temperature direct the growth and define the diameter of crystalline nanowires through a vapor-liquid-solid growth mechanism. A key feature of this method is that the catalyst used to define 1D growth can be selected 5 from phase diagram data and/or knowledge of chemical reactivity. A related approach termed solution-liquid-solid phase growth has been used by Buhro and coworkers to prepare nanowires of several III-V materials in solution, although not nitrides.

Figure 19:
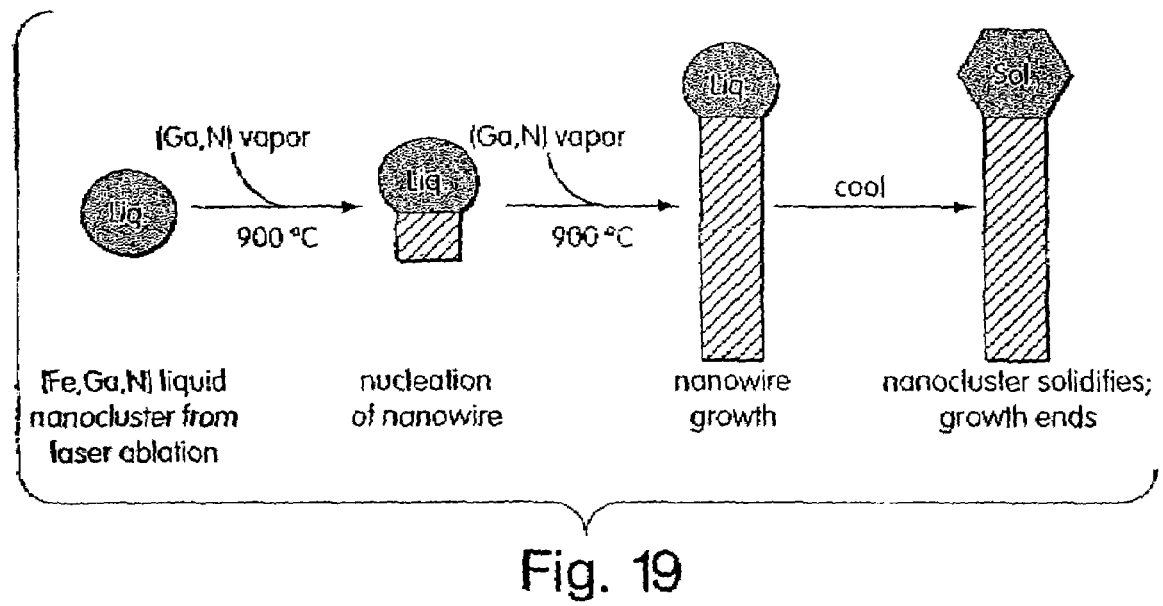
FIG. 19 is a schematic diagram showing GaN nanowire growth by laser assisted catalytic growth.

In the case of GaN, detailed information on ternary phase diagrams relevant to LCG (i.e., catalyst-Ga—N) is unavailable. However, we can use knowledge of the growth process to choose rationally a catalyst. Specifically, the catalyst should form a miscible liquid phase with GaN but not form a more stable solid phase under the nanowire growth conditions. The guiding principle suggests that Fe, which dissolves both Ga and N, and does not form a more stable compound than GaN will be a good catalyst for GaN nanowire growth by LCG. The overall evolution of nanowire growth following the generation of the catalytic nanocluster by laser ablation is illustrated in FIG. 19.

Figure 20A:
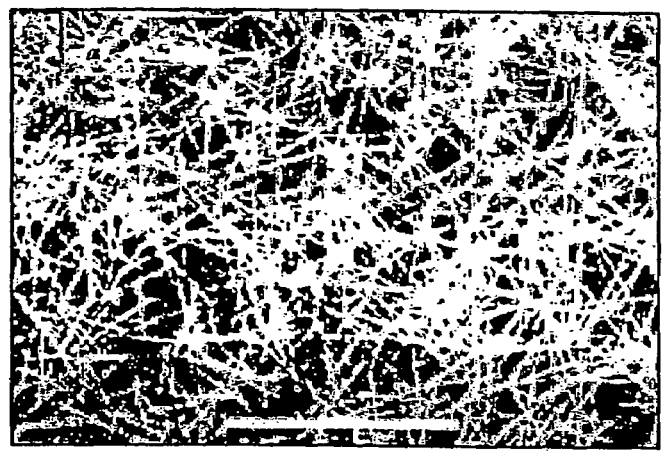
FIG. 20A shows a FE-SEM image of bulk GaN nanowire synthesized by laser assisted catalytic growth.
Figure 20B:
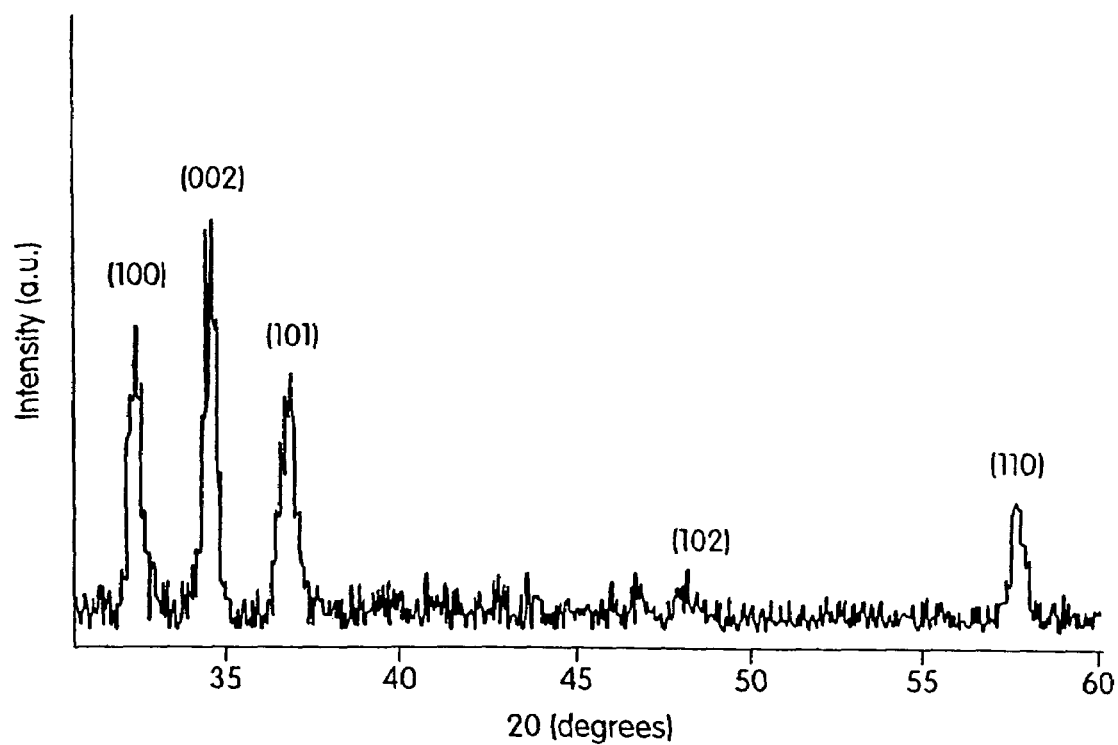
FIG. 20B shows a PXRD pattern recorded on bulk GaN nanowires.

Significantly, we find that LCG using a GaN/Fe target produces a high yield of nanometer diameter wire-like structures. A typical FE-SEM image of the product produced by LCG (FIG. 20A) shows that the product consists primarily of 1D structures with diameters on the orders of 10 nm and lengths greatly exceeding 1 μm; that is, high aspect ratio nanowires. The FE-SEM data also show that the products consist of ca. 90% nanowires, with the remaining being nanoparticles. We have also assessed the overall crystal structure and phase purity of the bulk nanowire samples using PXRD (FIG. 20B). All the relatively sharp diffraction peaks in the PXRD pattern can be indexed to a wurtzite structure with lattice constants of a=3.187 and c=5.178 Å. These values are in good agreement with literature values for bulk GaN: a=3.189, c=5.182 Å. In addition, comparison of the background signal and observed peaks indicates that the GaN wurtzite phase represents >95% of the crystalline material produced in our syntheses.

The LCG experimental apparatus is similar to that reported previously. A GaN/Fe (atomic ratio (GaN):Fe=0.95:0.05) composite target was positioned with a quartz tube at the center of a furnace. The experimental system was evacuated to 30 mtorr, and then refilled with anhydrous ammonia gas. While the pressure and flow rate were maintained at ca. 250 torr and 80 sccm, respectively, the furnace temperature was increased to 900° C. at 30° C./min. A pulsed Nd-YAG laser (1064 nm, 8 ns pulse width, 10 Hz repetition, 2.5 W average power) was then used to ablate the target with a typical ablation duration of 5 min. After ablation, the furnace was turned off and allowed to cool to room temperature. The system was then vented and light yellowish powders were collected from the end of inner quartz tube wall. The product was used directly for FE-SEM and PXRD studies. The product was suspended in ethanol and then transferred onto TEM grids for TEM, CBED and EDX measurements.

The morphology, structure and composition of the GaN nanowires have been characterized in further detail using TEM, CBED and EDX. TEM studies show that the nanowires are straight with uniform diameters, and typically terminate in a nanoparticle at one end. FIG. 20A shows a representative diffraction contrast image of one nanowire. The uniform contrast along the wire axis indicates that the nanowire is a single crystal. The nanoparticle (dark, high contrast feature) observed at the nanowire end is faceted as expected following crystallization of the liquid nanocluster (FIG. 19). We have also used EDX to address the composition of the nanowires and terminal nanoparticles. Data recorded on the nanowire show only Ga and N in a ratio ca. the same as a GaN standard, while the nanoparticles contain Ga, N, and Fe. The presence of Fe (with Ga and N) only in the terminal nanoparticle confirms the catalytic nature of Fe in the synthesis.

To probe further the importance of the catalyst, we have also investigated GaN nanowire growth using a Au catalyst. Gold has been used recently as a catalyst for growth of a number of nanowires of III-V and II-VI material, and as such might be expected to also function effectively in the growth of GaN nanowires. However, Au exhibits poor solubility of N and thus may not transport N efficiently to the liquid/solid growth interface. Consistent with this analysis, we have been unable to obtain GaN nanowire using the Au catalyst. We believe that this highlights the important role of the catalyst and how it can be rationally chosen.

Lastly, we have characterized the structure of GaN nanowires in greater detail using CBED and high resolution TEM (HRTEM). A typical CBED pattern (inset, FIG. 21A) of a nanowire exhibits a sharp diffraction pattern consistent with the single crystal structure inferred from the diffraction contrast images. Indexing this pattern further demonstrates that the [100] direction is aligned along the wire axis. In addition, FIG. 21B shows a lattice resolved HRTEM image of a GaN nanowire with a ca. 10 nm diameter. The image, which was recorded along the <001> zone axis, shows clearly the single crystal structure of the nanowire and the lattice planes along the [100], [010] and [−110] directions. This image demonstrates that the [100] direction runs parallel to the wire axis, and thus confirms the [100] growth direction in GaN nanowires.

In conclusion, we have exploited the LCG method for the rational synthesis of GaN nanowires. Highly pure GaN nanowires were obtained as single crystals with a unique [100] growth direction. We believe that this approach, which is based on the predictable-choice of catalyst and growth conditions, can be readily extended to the synthesis of InN, (GaIn)N alloys and related nitride nanowires. The synthesis of bulk quantities of single crystal nanowires of GaN and other technologically important semiconducting nitride materials is expected to open up many opportunities for further fundamental studies and applications.

FIG. 19 is a schematic diagram showing GaN nanowire growth by laser-assisted catalytic growth.

FIG. 20A shows a FE-SEM (LEO 982) image of bulk GaN nanowires synthesized by LCG. The scale bar corresponds to 1 μm. FIG. 20B shows a PXRD (Scintag, XDS2000) pattern recorded on bulk GaN nanowires. The numbers above the peaks correspond to the (hkl) values of the wurtzite structure.

Figure 21A:
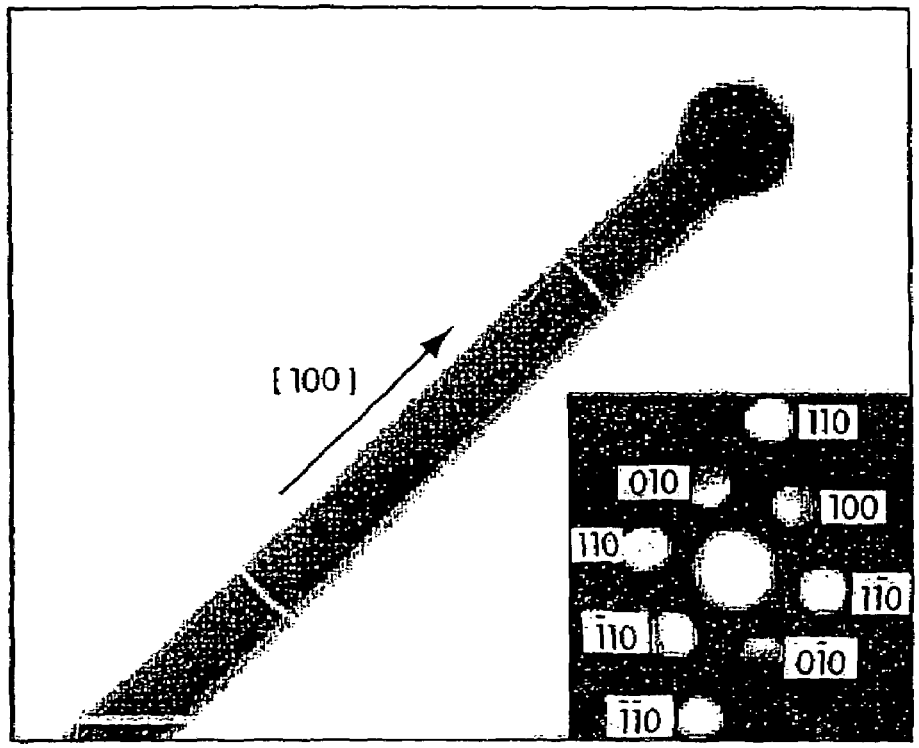
FIG. 21A shows a diffraction contrast TEM image of a GaN nanowire that terminates in a faceted nanoparticle of higher contrast.
Figure 21B:
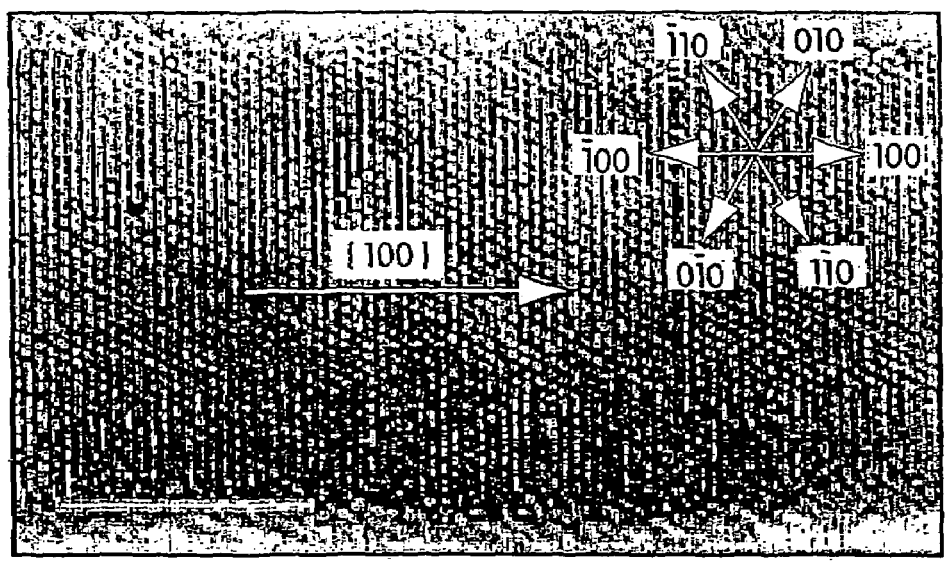
FIG. 21B shows an HRTEM image of another GaN nanowire with a diameter of approximately 10 nanometers.

FIG. 21 A shows a diffraction contrast TEM (Philips, EM420) image of a GaN nanowire that terminates in a faceted nanoparticle of higher (darker) contrast. The inset in FIG. 21A shows a CBED pattern recorded along <001> zone axis over the region indicated by the white circle. The white scale bar corresponds to 50 nm. FIG. 21B shows a HRTEM (JEOL 2010) image of another GaN nanowire with a diameter of ca. 10 nm. The image was taken along <001> zone axis. The [100], [010] and [−110] directions are indicated with the [100] parallel to the wire axis. The white scale bar corresponds to 5 nm.

Nanoscale Electronic and Optoelectronic Devices Assembled from Indium Phosphide Nanowire Building Blocks One dimensional nanostructures, such as nanowires (NWs) and nanotubes (NTs), are ideally suited for efficient transport of charge carriers and excitons, and thus are expected to be critical building blocks for nanoscale electronics and optoelectronics. Studies of electrical transport in carbon NTs have led to the creation of field effect transistors (FETs), single electron transistors, rectifying junctions and chemical sensors. These results indicate exciting applications possible from such materials, although the use of NT building blocks is quite limited in that selective growth and/or assembly of semiconducting or metallic NTs is not currently possible. The use of nanoscale structures as building blocks for bottom-up assembly of active devices and device arrays, which can eliminate the need for costly fabrication lines, will require that the electronic properties of the different blocks be both defined and controllable. To this end we report the rational assembly of functional nanoscale devices from compound semiconductor NW building blocks in which the electrical properties have been controlled by doping. Gate-dependent transport measurements demonstrate that indium phosphide (InP) NWs can be synthesized with controlled n-type and p-type doping, and can function as nanoscale FETs. In addition, the availability of well-defined n- and p-type materials has enabled the creation of p-n junctions by forming crossed NW arrays. Transport measurements reveal that the nanoscale p-n junctions exhibit well-defined current rectification. Significantly, forward biased InP p-n junctions exhibit strong, quantum confined light emission making these structures perhaps the smallest light emitting diodes created to date. Lastly, electric field directed assembly is shown to be one strategy capable of creating highly integrated and functional devices from these new nanoscale building blocks.

Single crystal InP NWs have been prepared by a laser-assisted catalytic growth (LCG), which has been described previously. The n-type and p-type InP NWs were prepared using tellurium (Te) and zinc (Zn) as dopants, respectively, and found to be of similar high quality as NWs produced without the addition of dopants. Field emission scanning electron microscopy (FE-SEM) images of as-synthesized Zn-doped InP NWs (FIG. 22A) demonstrate that the wires extend up to tens of micrometers in length with diameters on the order of 10 nanometers. High-resolution transmission electron microscopy (TEM) images (inset, FIG. 22A) further show that the doped NWs are single crystals with <111> growth directions. Generally, a 1-2 nm amorphous over-layer on the NWs is visible in TEM images. This thin layer is attributed to oxides formed when the NWs are exposed to air after synthesis. The overall composition of individual NWs determined by energy dispersive X-ray (EDX) analysis was found to be 1:1 In:P, thus confirming the stoichiometric composition of the NWs. EDX and other elemental analytic methods are, however, insufficiently sensitive to determine the doping level in individual NWs.

To confirm the presence and type of dopants in the NWs, we have performed gate-dependent, two terminal transport measurements on individual NWs. In these measurements, the NW conductance will respond in an opposite way to change in gate voltage ($V_g$) for n-and p-type NWs. Specifically, $V_g>0$ will lead to an accumulation of electrons and an increase in conductance for n-type NWs, while the same applied gate will deplete holes and reduce conductance for p-type NWs. FIGS. 22B and 22C and 100c show the typical gate-dependent I-V curves obtained from individual Te- and Zn-doped NWs respectively. The I-V curves are nearly linear for both types of NWs at $V_g=0$, indicating the metal electrodes make ohmic contact to the NWs. The transport data (FIG. 22B) recorded on Te-doped NWs show an increase in conductance for $V_g>0$, while the conductance decreases for $V_g<0$. These data clearly show that Te-doped InP NWs are n-type. Gate-dependent transport data recorded on Zn-doped NWs show opposite changes in conductance with variation in $V_g$ compared to the n-type, Te-doped InP NWs. Specifically, for $V_g>0$, conductance decreases and for $V_g<0$ conductance increases (FIG. 22C). These results demonstrate that the Zn-doped InP NWs are p-type.

Our results are quite reproducible. Measurements made on over twenty individual NWs, with diameters ranging from 20 nm to 100 nm, show gate effects in each case that are consistent with the dopant used during InP NW synthesis. In addition, the gate voltage can be used to completely deplete electrons and holes in n- and p-type NWs such that the conductance becomes immeasurably small. For example, the conductance of the NW in FIG. 22B can be switched from a conducting (on) to an insulating (off) state when $V_g$ is less than or equal to −20 V, and thus it functions as a FET. The conductance modulation can be as large as 4-5 orders of magnitude for some of the NWs. The relatively large switching voltage is related to the thick (600 nm) oxide barrier used in our measurements. This gate-dependent behavior is similar to that of metal-oxide-semiconductor (MOS) FETs and recent studies of semiconducting NT FETs. An important distinction of our work with respect to NTs is that predictable semiconducting behavior can be achieved in every NW. Taken together, these results clearly illustrate that single crystal InP NWs can be synthesized with controlled carrier type. Because these NWs are produced in bulk quantities, they represent a readily available material for assembling devices and device arrays.

Figure 23A:
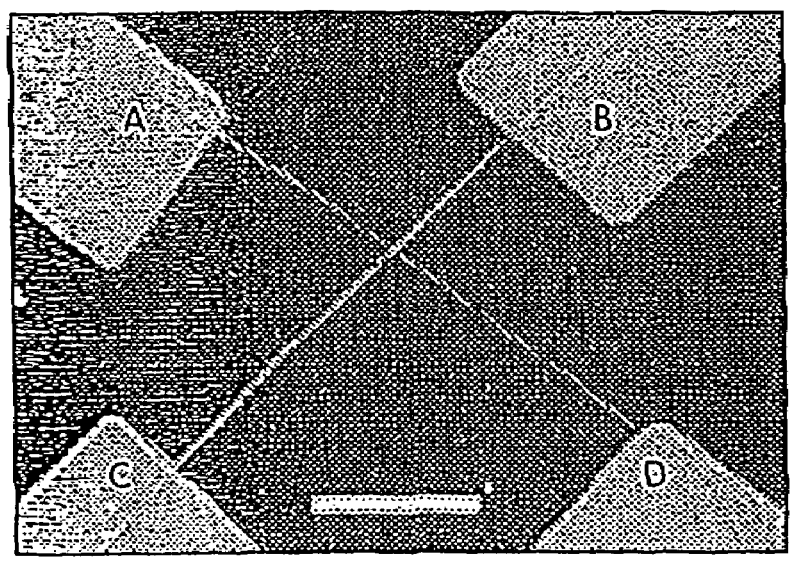
FIGS. 23A-23D illustrate crossed nanowire junctions and electrical properties.

The availability of well-defined n-and p-type NW building blocks opens up the possibility of creating complex functional devices by forming junctions between two or more wires. To explore this exciting opportunity, we have studied the transport behavior of n-n, p-p and p-n junctions formed by crossing two n-type, two p-type, and one n-type and one p-type NW, respectively. FIG. 23A shows a representative crossed NW device formed with a 29 nm and 40 nm diameter NW. The four arms are designated as A, B, C, D for the simplicity of discussion below. Significantly, the types of junctions studied are controllable for every experiment since we can select the types of NWs used to produce the crossed junction prior to assembly.

Figure 23B:
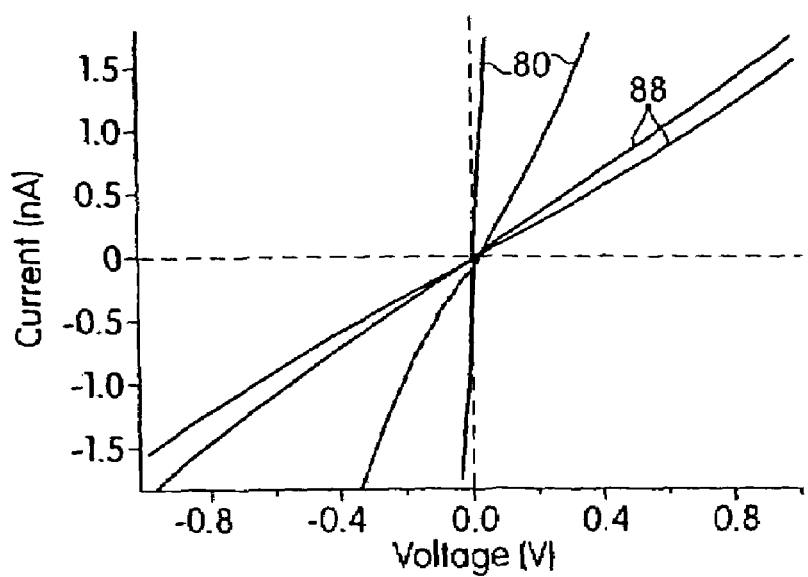
Figure 23C:
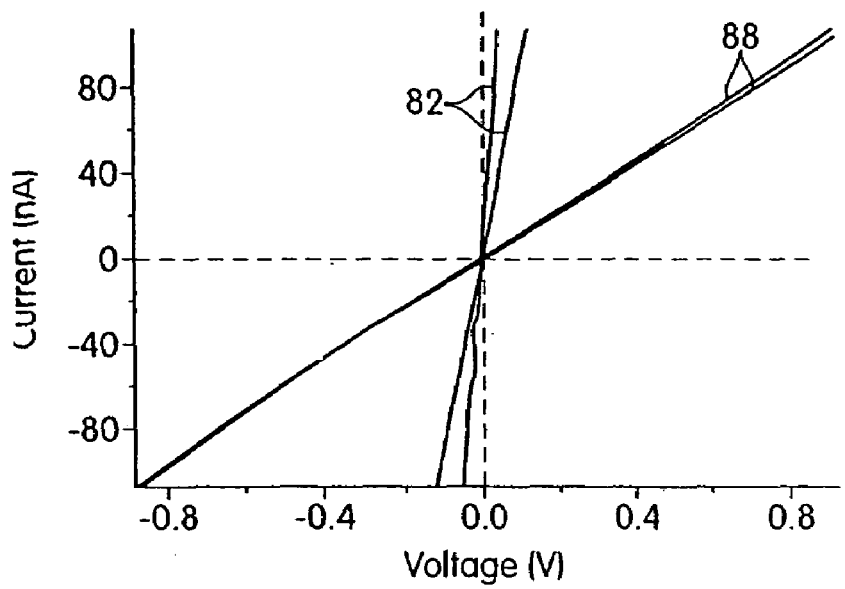

FIGS. 23B and 23C show the current-voltage (I-V) data recorded on n-n and p-p junctions, respectively. For both types of junctions, the transport data recorded on the individual NWs (AC, BD) show linear or nearly linear I-V behavior (curves 80, FIG. 23B and curve 82, FIG. 23C). These results show that the metal electrodes used in the experiments make ohmic or nearly ohmic contact to the NWs, and will not make nonlinear contributions to the I-V measurements across junctions. In general, transport measurements made across the n-n and p-p junctions show linear or nearly linear behavior, and allow us to infer two important points about junctions made in this way. First, interface oxide between individual NWs does not produce a significant tunneling barrier, since such a barrier will lead to highly non-linear I-V behavior. Second, the I-V curves recorded through each pair (AB, AD, CB, CD) of adjacent arms shows a similar current level, which is smaller than that of the individual NWs themselves. These results demonstrate that the junction dominates the transport behavior. Lastly, our data indicate that individual NWs make reasonably good electrical contact with each other, despite the small contact area ($10^{-12}$-$10^{-10}$ cm$^2$) and simple method of junction fabrication.

Figure 23D:
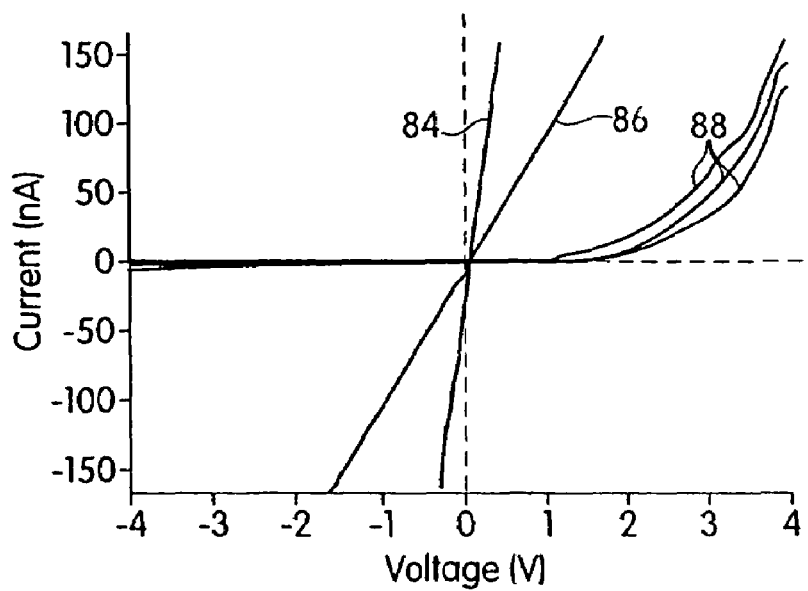

The good contact between individual NWs provides the basis for exploring these NW to make functional devices. As an example, we have made p-n junctions from crossed p- and n-type NWs. These junctions can be made reproducibly by sequential deposition of dilute solutions of n- and p-type NWs with intermediate drying. FIG. 23D shows typical I-V behavior of a crossed NW p-n junction. The linear I-V of the individual n- and p-type NWs components (curves 84 and 86) indicates ohmic contact between the NWs and metal electrodes. Transport behavior across the p-n junction (curves 88) shows clear current rectification; i.e., little current flows in reverse bias, while there is a sharp current onset in forward bias. Significantly, the behavior is similar to bulk semiconductor p-n junctions, which form the basis for many critical electronic and optoelectronic devices. In a standard p-n junction, rectification arises from the potential barrier formed at the interface between p- and n-type materials. When the junction is forward biased (p-side positively biased), the barrier is reduced and a relatively large current can flow through the junction; on the other hand, only small current can flow in reverse bias since the barrier is further increased.

There are several reasons we believe that the observed rectification is due to the p-n junction formed at the crossing point between p- and n-type InP NWs. First, the linear or nearly linear I-V behavior of individual p- and n-type NWs used to make the junction shows that ohmic contact have been made between the NWs and metal electrodes. This excludes the possibility that rectification arises from metal-semiconductor Schottky diodes. Second, the I-V behavior of the junction determined through every pair (AB, AD, CD, CD) of adjacent electrodes (curves 88 in FIG. 23D) exhibits a similar rectification effect and current level, which is also much smaller than the current level through the individual NWs. These results demonstrate that the junction dominates the I-V behavior. Third, four terminal measurements in which current is passed through two adjacent electrodes (e.g., A-B) while the junction voltage drop is measured across two independent electrodes (e.g., C-D) exhibit similar I-V and rectification with only a slightly smaller voltage drop (0.1-0.2V) compared to two terminal measurements at the same current level. Lastly, measurements made on ten independent p-n junctions showed similar rectification in the I-V data; i.e., significant current can only flow through p-n junctions when the p-type NW is positively biased.

Figure 24A:
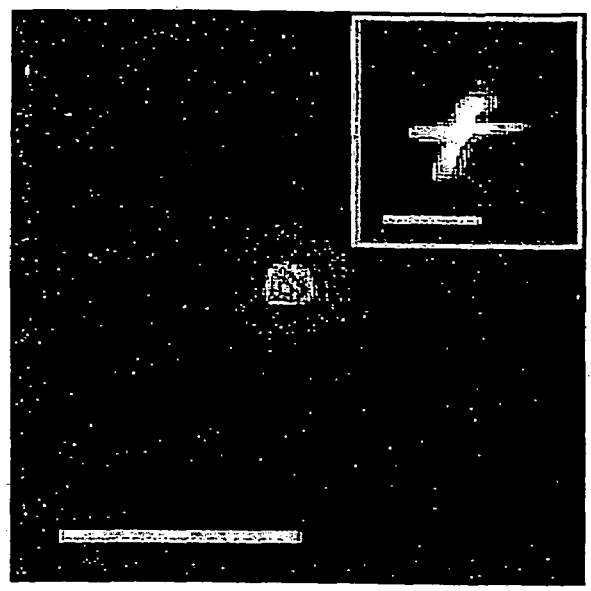
FIGS. 24A-24D illustrate optoelectrical characterization of nanowire P—N junctions.

The above data show unambiguously that we can now rationally fabricate nanoscale p-n junctions. In direct band gap semiconductors like InP, the p-n junction forms the basis for the critical optoelectronics devices, including light emitting diodes (LED) and lasers. To assess whether our nanoscale devices might behavior similarly, we have studied the photoluminescence (PL) and electroluminescence (EL) from crossed NW p-n junctions. Significantly, EL can be readily observed from these nanoscale junctions in forward bias. FIG. 24A shows an EL image taken from a typical NW p-n junction at forward bias, and the inset shows the PL image of a crossed NW junction. The PL image clearly shows two elongated wire-like structures, and the EL image shows that the light comes from a point-like source. Comparison of the EL and PL images shows that the position of the EL maximum corresponds to the crossing point in the PL image, thus demonstrating the light indeed comes out from the NW p-n junction.

The I-V characteristic of the junction (inset, FIG. 24B) shows clear rectification with a sharp current onset at ~1.5 volts. The EL intensity versus voltage curve of the junction shows significant light can be detected with our system at a voltage as low as 1.7 volts. The EL intensity increases rapidly with the bias voltage, and resembles the I-V behavior. The EL spectrum (FIG. 24C) shows a maximum intensity around 820 nm, which is significantly blue shifted relative to the bulk band gap of InP (925 nm). The blue-shift is due in part to quantum confinement of the excitons, although other factors may also contribute. The importance of quantum confinement can be seen clearly in EL results recorded from p-n junctions assembled from smaller (and larger) diameter NWs (FIG. 24D), which show larger (smaller) blue-shifts. The ability to tune color with size in these nanoLEDs might be especially useful in the future. The quantum efficiency (electron to photon) of these initial devices is relatively low, ~0.001%, which is not surprising since we have paid little attention to optimization. The efficiency is actually comparable to that (~0.002%) of early bulk InP LEDs. We attribute the low quantum efficiency to non-radiative recombination via surface states, and believe that this deleterious process can be reduced by surface passivation.

GaN is a direct wide bandgap semiconductor material, which emits light in the short wavelength (UV and blue) region at room temperature. Blue LEDs are important as emitters where strong, energy efficient and reliable light source are needed. Also it is important to enable production of full color LED displays and LED white lamp, since blue is one of the three primary colors (red, green and blue).

Here we report the first made BLUE/UV nanoLEDs (light emitting region on the order of 10 nm's), which is constructed with P-type Si and N-type (unintentionally doped) GaN nanowires. Together with the nanoLED we reported before which emits light in the near IR region, we show the great potential of making LEDs with different materials that would cover the full color spectrum.

Figure 25A:
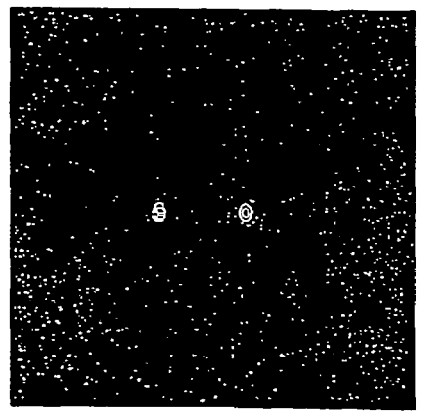
FIG. 25A shows an EL image taken from a p-type Si and n-type GaN nanojunction.
Figure 25B:
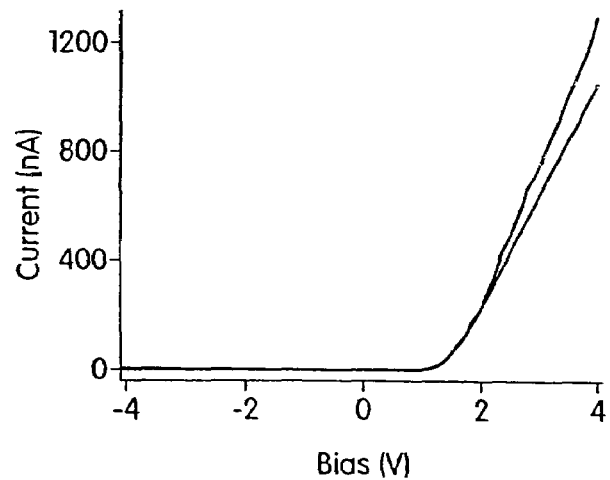
FIG. 25B shows current as a function of voltage for various gate voltages.
Figure 25C:
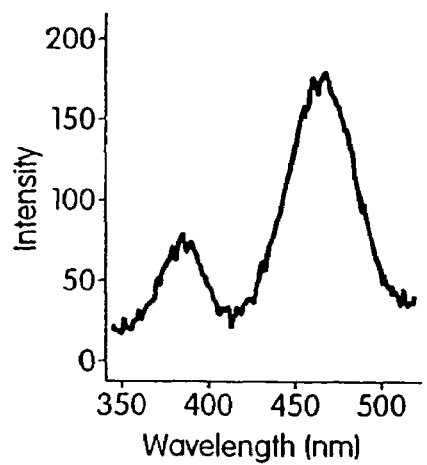
FIG. 25C shows an EL spectrum for the nanojunction of FIGS. 25A.

FIG. 25A shows an EL image taken from two P-type Si and N-type GaN crossed nanojunctions. The p-Si is doped with Boron. FIG. 25B shows current vs. voltage for various gate voltages. The nanojunction shows good rectification at different gate voltages. The El spectrum shown in FIG. 25C shows light emission is about 380 nm and 470 nm. A n-InP and p-Si nanojunction has good rectification.

To make highly integrated NW-based devices will ultimately require techniques to align and assemble these building blocks into well-defined arrays. To demonstrate the viability of this next stage of development, we have used electric fields (E-field) to align and position individual NWs into parallel and crossed arrays-two basic geometries for integration. The E-field directed assembly was carried out by placing a solution of NWs between electrodes (FIG. 26A), and then applying a bias of 50-100 V. The potential of this approach is readily seen in the case of alignment of a chlorobenzene suspended NWs between parallel electrodes (FIG. 26B). FE-SEM images show that nearly all of the NWs are aligned perpendicular to the parallel electrodes and along E-field direction. We have also used electrode arrays to position individual NWs at specific positions. For example, E-field assembly of NWs between an array of electrodes (FIG. 26C) demonstrates that individual NWs can be positioned to bridge pairs of diametrically-opposed electrodes and form a parallel array. In addition, by changing the field direction, the alignment can be done in a layer-by-layer fashion to produce crossed NW junctions (FIG. 26D). These data clearly show that E-field assembly represents a strategy to rationally deposit individual NWs with high degrees of directional and spatial control. We believe that highly integrated functional devices will be readily accessible using our NW building blocks in conjunction with this E-field and/or other assembly techniques.

Taken as a whole, the results presented in this letter provide a rational approach for the bottom-up assembly of nanoscale electronic and optoelectronic devices. Our demonstrated ability to assemble active devices in the absence of multi-billion dollar fabrication lines is of critical importance to the field and we believe augers well for the immediate and longer-term advances. We believe that the broad range of NW materials now available and the clearly defined ability to control their electronic properties will make possible nanoscale LEDs that cover the entire visible and near infrared range (e.g., GaN NWs for blue color). Such nanoscale light sources might be useful in creating new types of highly parallel optical sensors and for optical inter-connects in nanoelectronics. Moreover, the assembly of doped NW building blocks clearly has great potential for creating many other types of electronic devices and possibly even lasers.

InP NWs were synthesized using LCG. The LCG target typically consisted of 94% (atomic ratio) InP, 5% Au as the catalyst, and 1% of Te or Zn as the doping element. The furnace temperature (middle) was set at 800° C. during growth, and the target was placed at the upstream end rather than middle of the furnace. A pulsed (8 ns, 10 Hz) Nd-YAG laser (1064 nm) was used to vaporize the target. Typically, growth was carried out for 10 minutes with NWs collected at the downstream, cool end of the furnace.

Transport measurement on individual NWs were carried out using published procedures. Briefly, NWs were first dispersed in ethanol, and then deposited onto oxidized silicon substrates (600 nm oxide, 1-10 Ω·cm resistivity), with the conductive silicon used as a back gate. Electrical contact to the NWs was defined using electron beam lithography (JEOL 6400). Ni/In/Au contact electrodes were thermally evaporated. Electrical transport measurements were made using home built system with <1 pA noise under computer control.

The n-n and p-p junctions were obtained by random deposition. We first deposited NWs onto oxidized silicon substrates using relatively high concentrations, determined the positions of crossed NWs, and then defined electrodes on all four arms of the cross by electron beam lithography. Ni/In/Au electrodes were used to make contact to the NWs.

The p-n junctions were obtained by layer-by-layer deposition. First, a dilute solution of one type (e.g., n-type) of NW was deposited on the substrate, and the position of individual NWs was recorded. In a second step, a dilute solution of the other type (e.g., p-type) of NW was deposited, and the positions of crossed n- and p-type NWs were recorded. Metal electrodes were then defined and transport behavior was measured.

EL was studied with a home-built micro-luminescence instrument. PL or scattered light (514 nm, Ar-ion laser) was used to locate the position of the junction. When the junction was located, the excitation laser was shut off, and then the junction was forward biased. EL images were taken with a liquid nitrogen cooled CCD camera, and EL spectra were obtained by dispersing EL with a 150 line/mm grating in a 300 mm spectrometer.

Figure 22A:
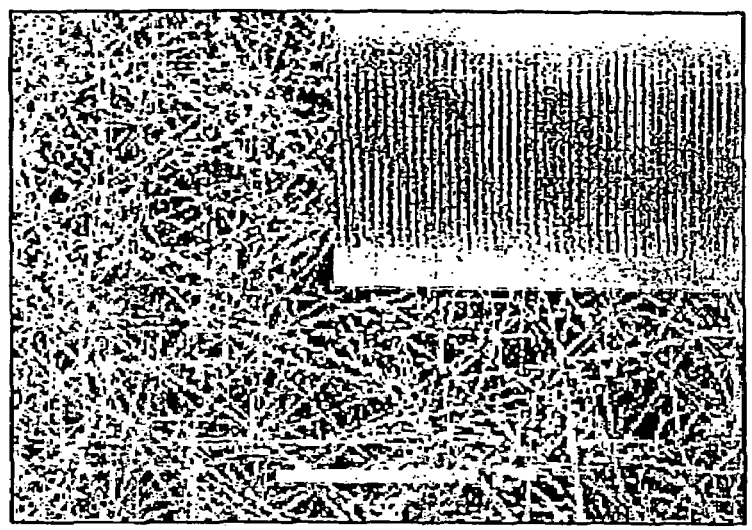
FIGS. 22A-22C illustrate doping and electrical transport of InP nanowires.
Figure 22B:
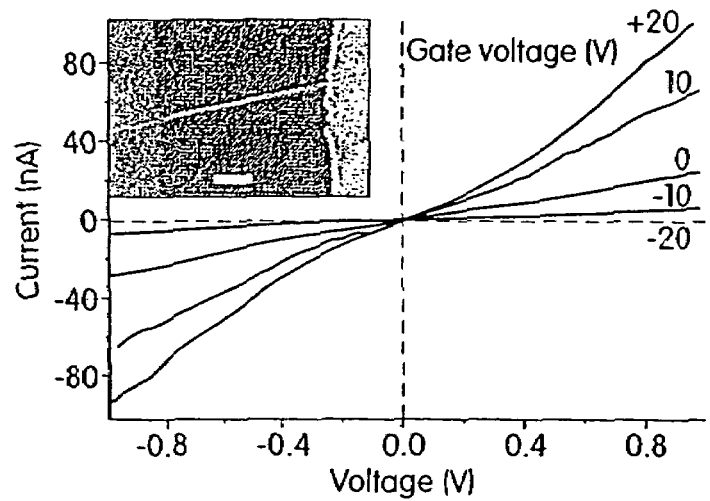
Figure 22C:
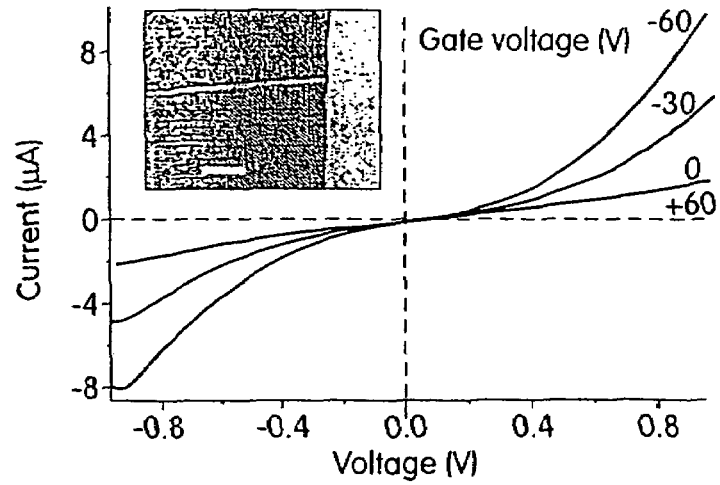

FIGS. 22A-22C illustrate doping and electrical transport of InP NWs. FIG. 22A shows a typical FE-SEM image of Zn-doped InP NWs. Scale bar is 10 μm. inset, lattice resolved TEM image of one 26 nm diameter NW. The (111) lattice planes are visible perpendicular to the wire axis. Scale bar is 10 nm. FIGS. 22B and 22C show gate-dependent I-V behavior for Te- and Zn-doped NWs, respectively. The insets in FIGS. 22B and 22C show the NW measured with two terminal Ni/In/Au contact electrodes. The scale bars correspond to 1 μm. The diameter of the NW in FIG. 22B is 47 nm, while that in FIG. 22C is 45 nm. Specific gate-voltages used in the measurements are indicated on the right hand sides of the FIGS. on the corresponding I-V curves. Data were recorded at room temperature.

FIGS. 23A-23D illustrate crossed NW junctions and electrical properties. FIG. 23A shows a FE-SEM image of a typical crossed NW device with Ni/In/Au contact electrodes. The scale bar corresponds to 2 μm. The diameters of the NWs are 29 nm (A-C) and 40 nm (B-D); the diameters of the NWs used to make devices were in the range of 20-75 nm. FIGS. 23B-23D show I-V behavior of n-n, p-p and p-n junctions, respectively. The curves 80 and 82 correspond to the I-V behavior of individual n- and p-NWs in the junctions, respectively. The curves 88 represent the I-V behavior across the junctions. The current recorded for the p- and n- type NWs in FIG. 23D is divided by 10 for better viewing. The solid lines represent transport behavior across one pair of adjacent arms, and the dashed lines represent that of the other three pairs of adjacent arms. Data were recorded at room temperature.

Figure 24B:
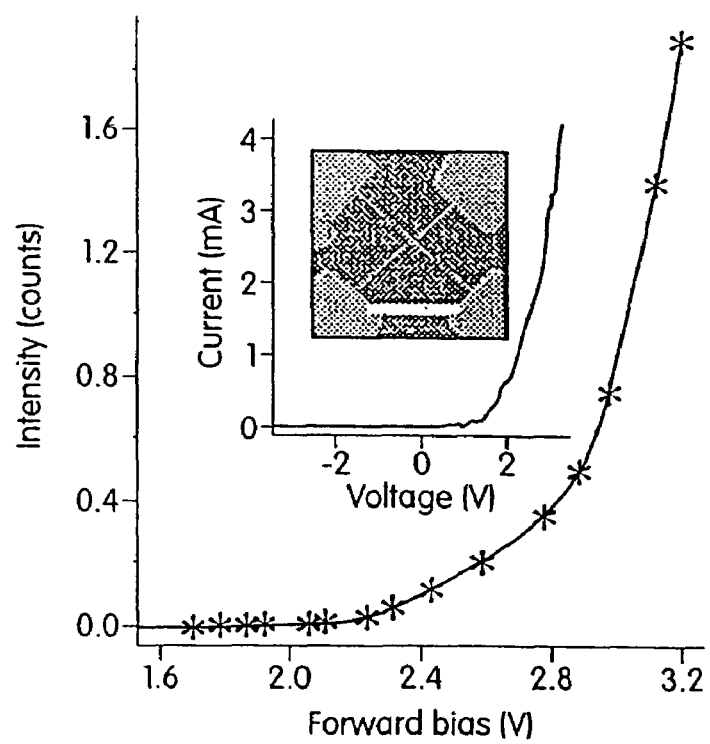
Figure 24C:
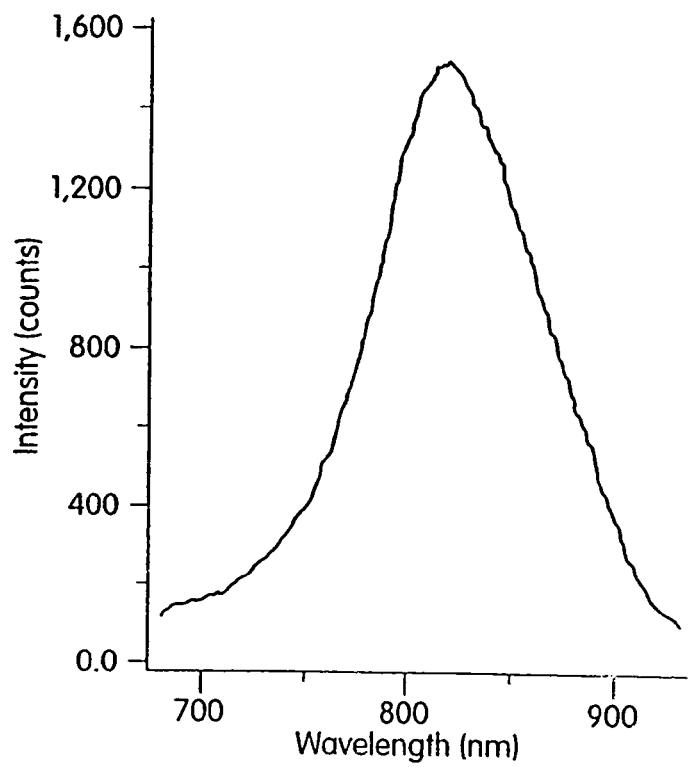
Figure 24D:
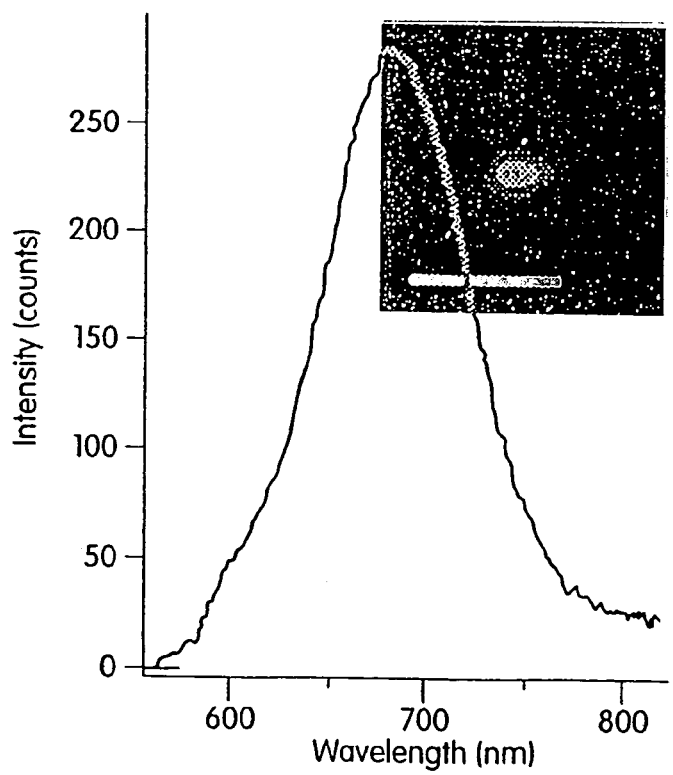

FIGS. 24A-24D illustrate optoelectrical characterization of NW p-n junctions. FIG. 24A is an EL image of the light emitted from a forward biased NW p-n junction at 2.5 V. The inset in FIG. 24A shows the PL image of the junction. Both scale bars correspond to 5 μm. FIG. 24B shows the EL intensity versus voltage. The inset in FIG. 24B shows the I-V characteristics and the inset in the inset shows the FE-SEM image of the junction itself. The scale bar corresponds to 5 μm. The n-type and p-type NWs forming this junction have diameters of 65 and 68 nm, respectively. FIG. 24C shows an EL spectrum of the junction shown in FIG. 24A. The spectrum peaks at 820 nm. FIG. 24D shows an EL spectrum recorded from a second forward biased crossed NW p-n junction. The EL maximum occurs at 680 nm. The inset in FIG. 24D shows the EL image and demonstrates that the EL originates from the junction region. The scale bar is 5 μm. The n-type and p-type NWs forming this junction have diameters of 39 and 49 nm, respectively.

Figure 26A:
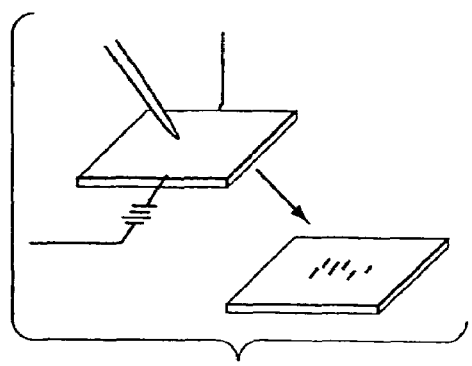
FIGS. 26A-26D illustrate parallel and orthogonal assembly of nanowires with electric fields.
Figure 26B:
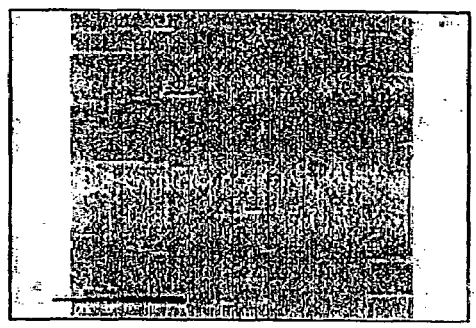
Figure 26C:
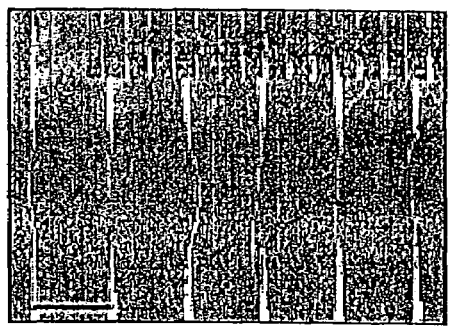
Figure 26D:

FIGS. 26A-26D illustrate parallel and orthogonal assembly of NWs with E-fields. FIG. 26A is a schematic view of E-field alignment. The electrodes (orange) are biased at 50-100 V after a drop of NW solution is deposited on the substrate (blue) FIG. 26B shows a parallel array of NWs aligned between two parallel electrodes. The NWs were suspended in chlorobenzene and aligned using an applied bias of 100 V. FIG. 26C shows a spatially positioned parallel array of NWs obtained following E-field assembly using a bias of 80 V. The top inset in FIG. 26C shows 15 pairs of parallel electrodes with individual NWs bridging each diametrically opposed electrode pair. FIG. 26D shows a crossed NW junction obtained using layer-by-layer alignment with the E-field applied in orthogonal directions in the two assembly steps. The applied bias in both steps was 80 V. The scale bars in FIGS. 26B-26D correspond to 10 μm.

Bottom-Up Assembly of Nanoscale Electronic Devices from Silicon Nanowires

Four types of important functional nanodevices have been created by rational bottom-up assembly from p and n-type silicon nanowires (SiNWs) with well controlled dopant type and level. In all these devices, electrical transport measurements on individual p and n-type SiNWs suggested ohmic or nearly ohmic contact between SiNWs and leads. Significantly, four-probe measurements across pn junctions consisting of crossed p-type and n-type SiNWs showed current rectification behavior as expected for pn diode behavior. $n^+pn$ crossed junctions were also assembled to create bipolar transistors, in which common base/emitter current gains as large as 0.94/16 were obtained. Complementary inverters made of crossed lightly doped pn junctions showed clear output voltage inverse to input voltage with a gain of 0.13. Tunnel diodes in form of heavily doped SiNW pn crosses showed negative differential resistance (NDR) behavior in forward bias with a peak-to-valley ratio (PVR) of 5 to 1.

Miniaturization of conventional electronics has been intensely pursued recently. But the fundamental limits of lithographical methods will prevent the current techniques from reaching the deep nanoelectronics regime. The use of nanoscale structures as building blocks for the bottom-up assembly of integrated devices, where both the fabrication and assembly of individual blocks are expected to be cheap, can thus eliminate greatly the cost of fabrication lines while still maintaining some concepts that have proven successful in microelectronics. One dimensional structures such as nanowires (NWs) and nanotubes (NTs) are ideal candidates as critical building blocks for nanoelectronics. How to construct the functional nanodevices and device arrays with these building blocks is essential to nano science and technology. NTs have been tested as field effect transistors, single electron transistors. The NT-NW heterojunctions, NT intramolecular junctions and crossed junctions have also been demonstrated. However, the use of NTs in rational assembly is limited by unpredictability of individual tube properties because the specific growth of metallic and semiconductor NTs is not controllable and controlled doping of semiconductor NTs is difficult.

Figure 27A:
FIGS. 27A-27F illustrate crossed silicon nanowire junctions.
Figure 27B:
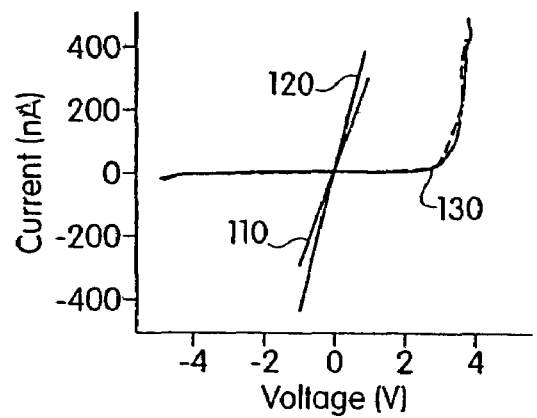

Previously, we demonstrated the controlled doping of single crystal semiconductor SiNWs, where the type of dopant (p-type and n-type) and the relative doping concentration (from lightly to degenerately) were well controlled. These SiNWs, whose properties are predictable and controllable, therefore provide the critical building blocks for bottom-up assembly of active devices and device arrays. It is possible that the highly dense SiNW device arrays can be formed by the directed assembly of chemical assembly, for example, the specific peptide binding to semiconductor, DNA base matching interaction, and/or the ligand-receptor interaction. To realize workable integrated devices, understanding the electrical properties of individual bottom-up assembled active devices is the prerequisite. Here we report the rational assembly of ftmctional nanodevices from these SiNWs with diameters from 20 to 50 nm and the device electrical properties. And we demonstrate that control of dopant type and doping level provides us the capability to fabricate multiple types of electronic devices. Four types of important functional structures including pn diodes, bipolar transistors, complementary inverters and tunnel diodes were created by controllably combining SiNWs of varying p and n-type doping levels. Nanoscale pn junctions were created in form of crossed SiNW junctions. Electrical transport measurements on these pn junctions showed the current rectification predictable by semiconductor physics. We have exploited our ability to construct $n^+pn$ crossed SiNW junctions to bipolar transistors which were demonstrated to have common base/emitter current gains as large as 0.94/16. The inverters made of lightly doped pn crosses showed clearly the output voltage inverse to the input voltage with voltage gain of 0.13. And the results of tunnel diodes made of heavily doped pn crossed showed NDR behavior in forward bias with a PVR of 5 to 1. The p-type and n-type SiNWs were synthesized by using diborane and phosphorus, respectively as doping source during laser-assisted catalytic growth of SiNWs. Metal leads contact with SiNWs on doped silicon substrate with 600 nm thermal oxide were defined by electron beam lithography. The pn, pp and nn junctions were formed by crossing one p-type and one n-type, two p-type and two n-type SiNWs, respectively. The types of junctions were controlled by choosing the types of SiNWs used to create a given junction. A typical field emission scanning electron microscopy (FE-SEM) image of cross junctions is shown in FIG. 27A, where the four contact leads are labeled as 1, 2, 3 and 4 for the convenience of discussion. FIG. 27B shows current versus voltage (I-V) data on a pn crossed junction with diameters of p and n-type SiNWs as small as 20.3 nm and 22.5 nm, respectively. Four-terminal measurements across junction were performed by flowing current between two adjacent leads (e.g., leads 1-2 or leads 1-4, the positive current direction is from p to n-type SiNW) and measuring the voltage drop between the other two leads (e.g., leads 3-4 or leads 3-2). The I-V curve across junction (FIG. 27B curve 130) shows little current in reverse bias (negative bias in our setup) and very sharp current onset in forward bias (positive bias). In contrast, single p (between leads 1-3) and n-type (between leads 2-4) SiNWs show linear I-V behavior (FIG. 27B curves 110 and 120, respectively), which suggests ohmic (not rectifying) contact between SiNWs and leads. And thus this rectifying behavior must be caused by junction itself. This behavior can be explained by the energy band diagrams of a pn junction diode. The built-in potential barrier forms at the junction interface when p and n-type SiNW contact with each other. Electrons can not tunnel through the wide space charge region forming at the junction interface but can be transported by thermal excitation. Forward bias decreases the built-in potential barrier and thus large amount of current can flow (FIG. 27E), while reverse bias increases the barrier and thus current level is low (FIG. 27F).

The p and n-type SiNWs were dispersed in to aceton separately. p-n junctions were obtained by sequential deposition. The solution of one type of SiNWs (e.g., n-type) was first deposited onto the substrate and the positions of SiNWs were recorded with respect to alignment marks. Secondly, the solution of the other type of SiNWs (e.g., p-type) was deposited and the positions of crossed pn junctions were recorded. pp or nn junctions were obtained by depositing only one type of SiNWs: p-type or n-type. The junction positions were then recorded.

The reasons why we believe the rectifying behavior is pn diode behavior instead of some other asymmetric tunneling barrier at the junction interface are: (a). The intrinsic oxide layer of SiNWs is thin enough that electrons can easily tunnel through the oxide layer and the reasonable strong coupling between p and n-type wire at the junction still exists and thus the built-in potential barrier can form. This is confirmed by the transport measurements on pp and nn junctions. The single wires (between leads 1-3, 2-4) in pp (FIG. 27C curves 110) and nn junctions (FIG. 27D curves 120) show linear or almost linear I-V behavior suggesting good contact. Two terminal measurements (between leads 1-2, 1-4, 2-3, or 3-4) on pp (FIG. 27C curves 130) and nn (FIG. 27D curves 130) junctions show linear and almost linear I-V. Comparing two-terminal measurement resistance across junctions to single SiNW resistance, we find that the magnitude of junction resistance is similar to the wire resistance, suggesting that the oxide doesn't cause significant electron tunneling barrier. (b) The measurements on 20 independent pn junctions showed consistent correct rectifying behavior.

Figure 28A:
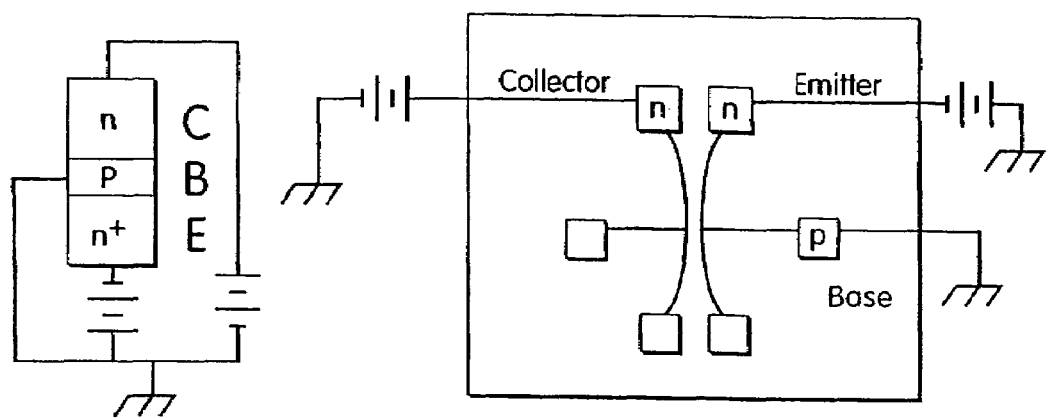
FIGS. 28A-28D illustrate n+pn crossed silicon nanowire bipolar transistors.
Figure 28B:
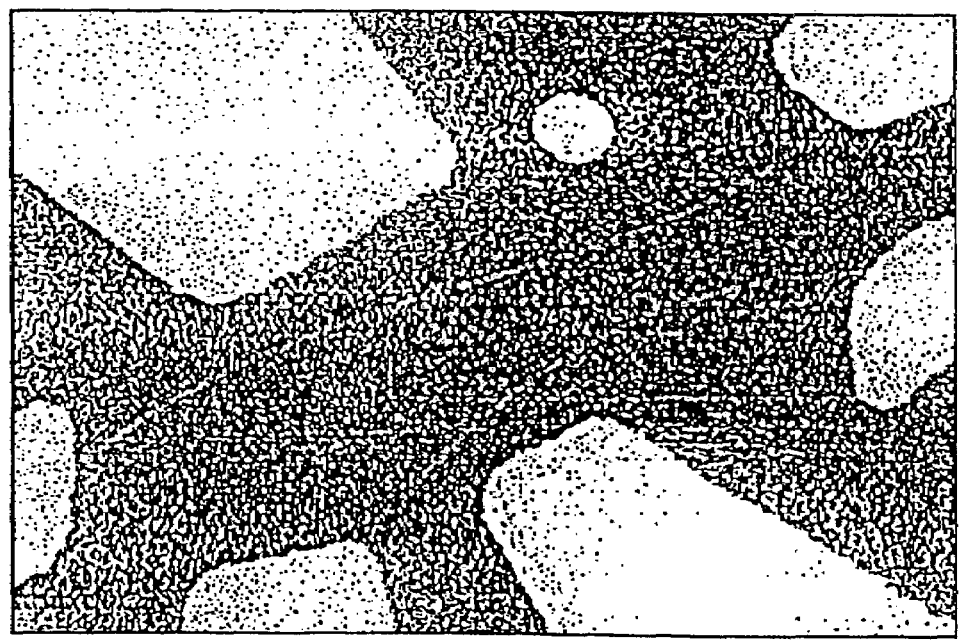
Figure 28C:
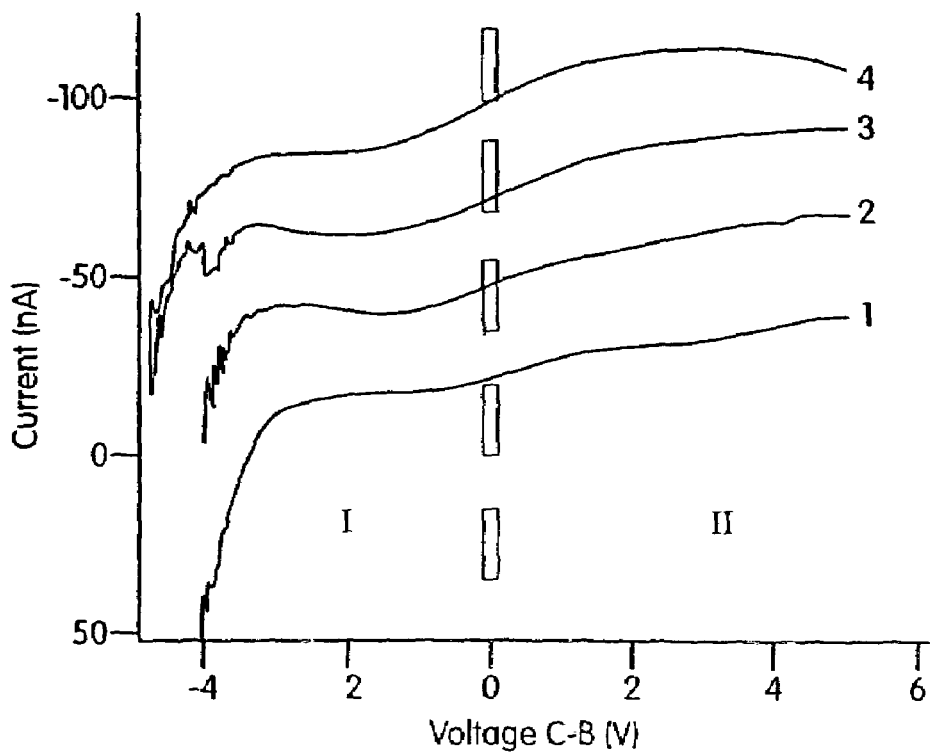

As the basic unit of most semiconductor devices, pn junctions provide the characteristics needed for rectifiers, amplifiers, switching circuits and many other electronic circuit functions. Success in making pn junction from SiNW crosses provides us the possibility to make other important functional devices. To demonstrate, we can create not only a passive device: p-n diode, but also the active device; we constructed bipolar transistor, which is capable of current gain. A bipolar transistor is a $n^+pn$ (FIG. 28A left) or $p^+np$ junction device, which requires high doping level in emitter, low doping in base and collector. Well control in doping of SiNWs provides us the capability to make this complex device. Our $n^+pn$ bipolar transistors were constructed by mechanically manipulating two n-type SiNWs (one heavily doped, the other lightly doped) onto one lightly doped p-type wire and were operated in common base configuration (FIG. 28A right). FIG. 28B is a typical SEM image of bipolar transistors. The SiNWs and junctions in transistors were first characterized individually. The I-V curves of three individual SiNWs are linear and the two individual junctions have correct rectifying behavior. Then the $n^+$-type SiNW was used as emitter while the n-type as collector to do bipolar transistor measurements. The emitter-base (E-B) is always forward biased to inject electrons into base region. When the collector-base (C-B) voltage is greater than zero, the transistor is operated in the active mode, in which the C-B junction is reverse biased and only a very small leakage current will flow across the junction. However, the electrons injected from emitter can diffuse through the base to reach the C-B junction space charge region and will be collected by collector. The actual collector current depends only on the injected electrons from emitter and thus depends only on the E-B voltage. This is clearly seen in FIG. 28C regime II, where the collector current goes high with the forward E-B voltage while change slowly with C-B voltage which results from Early effect and the existence of slowly increasing leakage current with reverse bias. This demonstrates the transistor action: large current flow in a reverse biased collector junction can result from carriers injected from a nearby emitter junction. When the (C-B) voltage is bellow zero, the bipolar transistor works in saturation mode (FIG. 28C regime I), in which both E-B and C-B junctions are forward biased. The collector current from emitter injection will be compensated by the forward biased C-B current. So the collector current goes down with forward C-B voltage. The higher the forward bias on E-B, the higher the forward bias on C-B needed to compensate the current to zero (FIG. 28C curve 1 to 4).

The $n^+pn$ bipolar transistors were fabricated by deposition and machanical manipulation. First, p-type SiNWs were deposited from solution onto the substrate. In the second step, the $n^+$ and n-type SiNWs were attached to sharp STM tips and released onto the p-type SiNWs under optical microscope.

The common base current gain of the bipolar transistor in active mode is as large as 0.94 (FIG. 28D) and the common emitter current gain is 16. Three important points are suggested from this large current gain. (a) The efficiency of electron injection from emitter to base is quite high, resulting from the higher doping concentration in emitter than in base. (b) Although the base region is wide (15 µm), the active interaction between emitter and collect still exists. Most of injected electrons from emitter can go through the base to reach the collector, which suggests that the mobility of electrons in base is quite high. (c) The space charge region between base and collector has high efficiency to collect electrons and sweep them into collector, suggesting that the oxide barrier at the interface doesn't contribute significantly, which further confirms our analysis on single pn junctions. Our bipolar transistor can be improved, for example, by reducing the base width, to approach the performace of the commercial one in which the typical common base current gain is larger than 0.99.

Figure 29A:
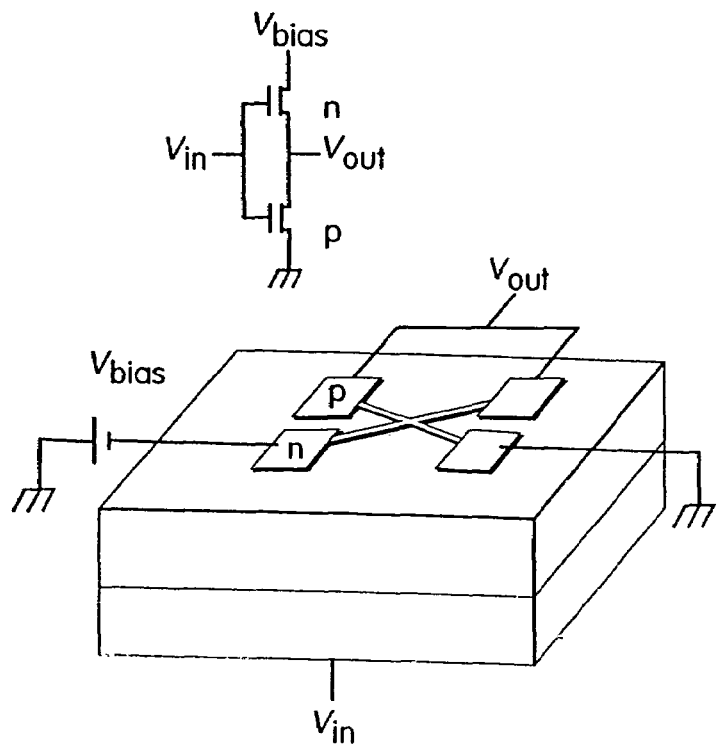
FIGS. 29A-29D illustrate complementary inverters and tunnel diodes.
Figure 29B:
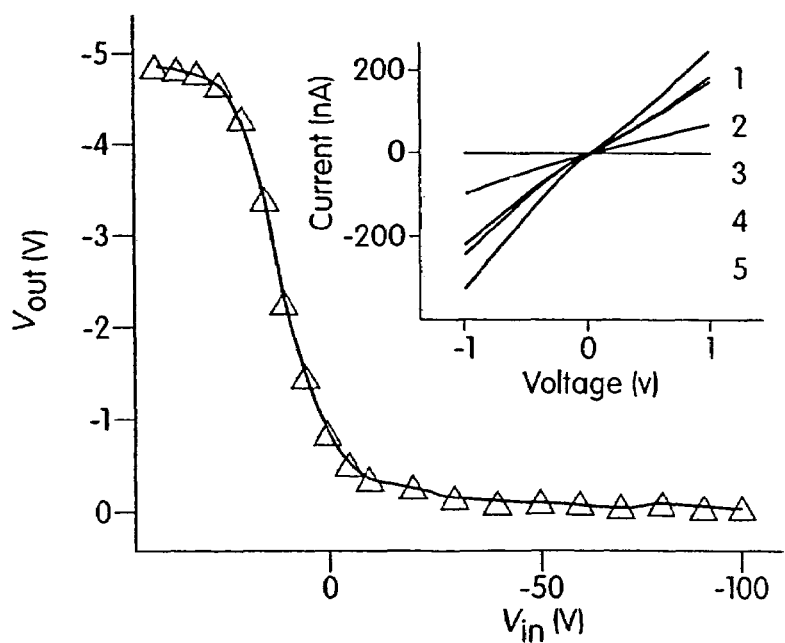

To exploit the applications of these bottom-up building blocks in logic circuit, and to further demonstrate the capability that contolled doping of SiNWs can provide us, we create a complementary inverter in form of a lightly p and a lightly n-doped SiNW cross. The schematics of an crossed SiNW inverter structure is shown in FIG. 29A (bottom) while that of an inverter in semiconductor physics is shown in FIG. 29A (top). The lightly doped p and n-type SiNWs in the inverter show very large gate effect and can be completely depleted as is shown for p-type SiNW in FIG. 29B inset. As seen in FIG. 29B, the output voltage is negative (zero) with the positive (negative) input voltage, which is the typical inverter behavior. This behavior can explained like this: the depletion of n-type (p-type) wires by negative (positive) input makes the output equal to ground (bias). The voltage gain is calculated as 0.13, the slope of voltage inversion. The gain is lower than that in commercial inverters which is larger than 1, but can be improved by using thinner gate oxide layer instead of the 600 nm oxide, which reduces the gate response of SiNWs, and using more lightly doped SiNWs, which needs more effort to make ohmic contact with and to be further investigated.

While two crossed lightly doped p and n-type SiNWs make inverters, two crossed degenerately doped $p^+$ and $n^+$-type SiNWs can form tunnel diodes. In contrast to the pn junction, the tunnel diode do not show rectifying behavior, but rather show NDR behavior in forward bias, with a PVR of 5 to 1 shown in FIG. 29C. The difference can be explained by Esaki diode mechanism. The built-in potential forms when $p^+$ and $n^+$-type contact each other, but the space charge region width is thin enough to allow electron tunneling. Electrons can tunnel through this thin space charge region under reverse bias (FIG. 29D left) and low forward bias (FIG. 29D middle) causing the current to flow. Beyond a certain point, a further increase in the forward bias results in the conduction band of the n-side moving into the band gap of the p-side (FIG. 29D right) which suppresses electron tunneling and thereby reduces current. Further increases of forward bias reduce the built-in potential barrier which allows thermal excitation mechanism to dominate conduction and the current goes high.

The results described here demonstrate the bottom-up assembly of multiple types of nanoscale electronic devices from doped SiNWs with control over both dopant type and doping level. The individual devices show predictable behaviors similar to the conventionally fabricated devices. The mass production and high intergration of these functional nanodevices can be realized by chemical assembly assisted with electric field and flowing solution alignment, which will lead to exciting practical applications in nanoelectronics while avoiding high cost fabrication lines. Moreover, we can expect that, in conjunction with optical signal, pn diode crosses can function as photodiodes and pn solar cells, and bipolar transistor crosses can form phototransistors.

The alignment of NW by electric field and flowing solution produced one-type of parallel NW arrays. Switching the direction of electric field and flowing solution to lay down the the other type of NWs can form very dense NW crosses.

Figure 27C:
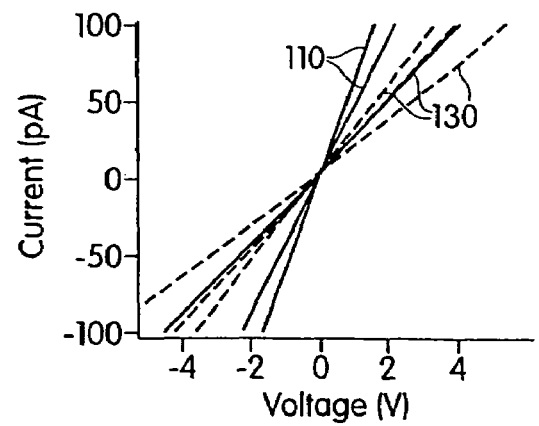
Figure 27D:
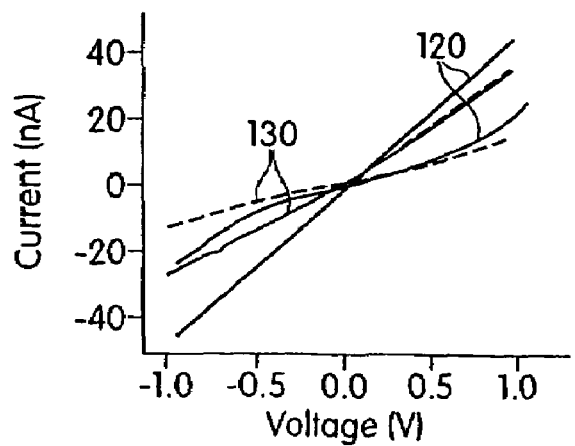
Figure 27E:
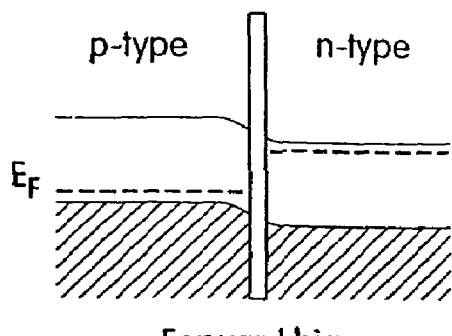
Figure 27F:
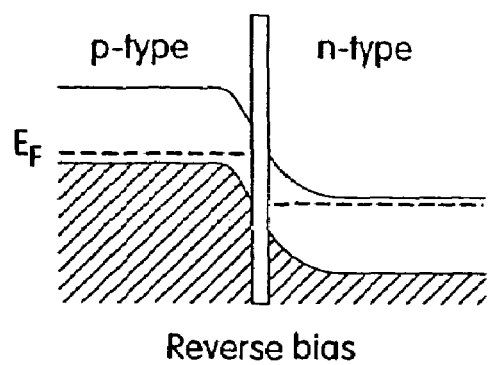

FIGS. 27A-27F illustrate crossed SiNW junctions. FIG. 27A shows a typical FE-SEM image of crossed NW junctions with Al/Au as contact leads. The scale bar is 2 µm. The diameters of NWs are in the range of 20 to 50 nm. FIGS. 27B-27D show I-V behavior of pn, pp and nn junctions, respectively. The curves 110 and 120 correspond to the I-V behavior of individual p and n-type SiNWs in junctions, respectively. The curves 130 represent the four-terminal I-V through pn junction in FIG. 27B and two terminal I-V through pp and nn junction in FIGS. 27C and 27D, respectively. In FIG. 27B, the solid line is I-V by following current between lead 1 and 2 and simultaneouly measuring the voltage between lead 3 and 4 while the dashed line correponds to that by following current between 1 and 4 and measuring voltage between 3 and 2. In FIGS. 27C and 27D, the solid lines are I-V across one pair of adjacent leads (1-2) and the dashed lines are those across the other three pairs (1-4, 2-3, 3-4). FIGS. 27E and 27F show the energy band diagrams of a pn junction under forward bias and reverse bias, respectively.

Figure 28D:
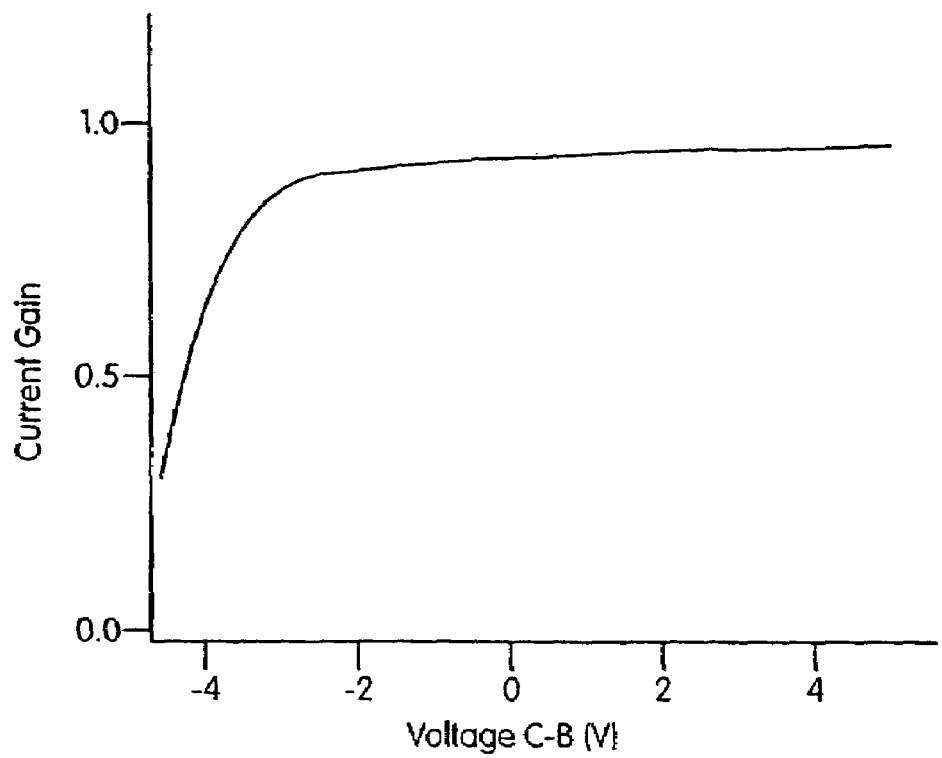

FIGS. 28A-28D illustrate $n^+pn$ crossed SiNW bipolar transistors. FIG. 28A shows the common base configuration schematics of an $n^+pn$ bipolar transistor in semiconductor physics (left) and in crossed SiNW structure (right). The $n^+$, p and n-type SiNWs function as emitter, base and collector, respectively. The base is grounded. The emitter is negatively biased at specific values. The collector voltage is scanned from postive to negative. FIG. 28B shows a typical FE-SEM image of SiNW bipolar transistor. The scale bar is 5 μm. FIG. 28C shows a collector current vs collector-base voltage behavior recorded on an $n^+pn$ transistor with emitter and base SiNWs 15um apart. Curve 1 to 4 correspond to the behavior at emitter-base voltages of −1, −2, −3, −4V. Regime I and II are separated by dashed line, correponding to saturation mode and active mode, respectively. FIG. 28D shows common base current gain vs collector-base voltage.

Figure 29C:
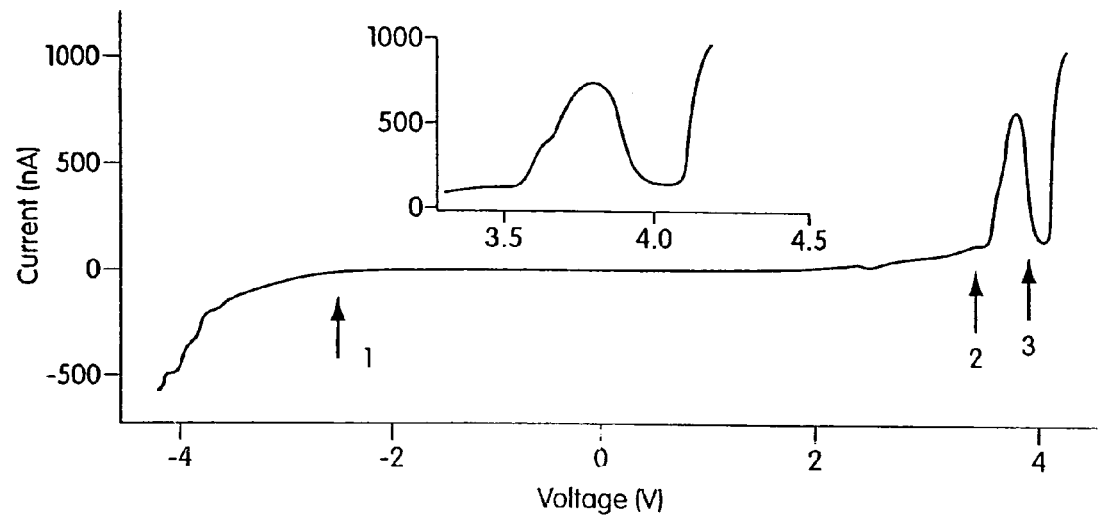
Figure 29D:
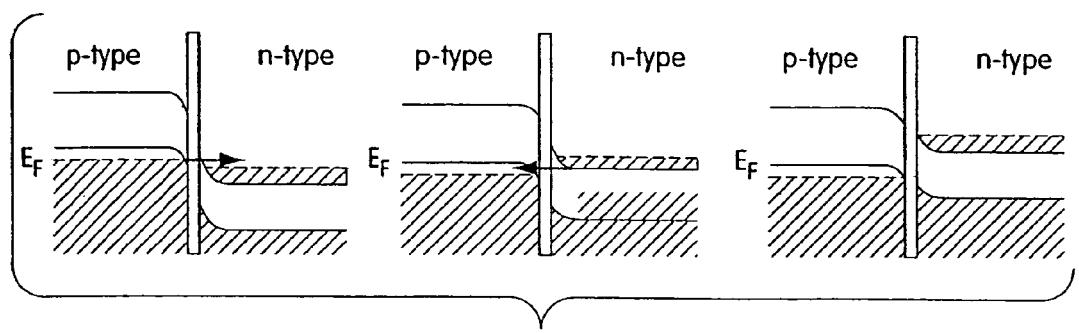

FIGS. 29A-29D illustrate complementary inverters and tunnel diodes. FIG. 29A shows schematics of a complementary inverter structure in semicondutor physics (top) and that formed by a lightly doped pn cross (bottom). In bottom schematics, one end of n-type NW is biased at −5V and one end of p-type NW is grounded. Input voltage is back gate voltage and the other ends of p and n-type NWs are shorted as output terminal. FIG. 29B shows output voltage vs input voltage data in a pn cross inverter. The inset in FIG. 29B is the I-V curves of p-type NW in the inverter. Curve 1 to 5 correspond to I-V at back gate voltage −50, −30, −10, 0 and 10V, respectively. The n-type NW in this inverter has similar I-V behavior and can be completely depleted at a gate voltage of −30V. FIG. 29C shows two terminal mearsurement data of a tunnel diode made from a heavily doped pn cross. The I-V behavior of individual p and n-type SiNWs have been tested to be linear. The inset in FIG. 29C spreads out the part of I-V curve showing NDR. FIG. 29D shows the energy band diagrams of a crossed SiNW tunnel diode. At reverse bias (e.g. at position 1 in FIG. 29C), electrons can tunnel through the junction (left diagram). At small forward bias (e.g. at position 2 in FIG. 29C), electron tunneling is also permitted (middle diagram). At further increased forward bias (e.g. at position 3 in FIG. 29C), electron tunneling is forbidden (right diagram).

Controlled Placement of Nanowires on Surfaces

1. A stable suspension of Nanowires (NWs) in ethanol was prepared by sonicating NWs in ethanol in a bath sonicator for around 3 minutes.
2. The substrate (silicon wafer) was covered by a self-assembled monolayer (SAM) with —NH$_2$ termination.
3. The microfluidic molds are made of PDMS. A microchannel formed when the substrate came in contact with PDMS mold, with three walls of the conduit corresponding to the molded features in the mold and the fourth corresponded to the surface of the substrate, which was chemically modified as described in 2.
4. The NW suspension flowed through as-made microchannel with an application of +100 volt bias on the substrate. After a flowing time around 10 min, the channel was washed with ethanol, then let dry naturally. When the PDMS stamp was removed, we got NWs arrays aligned in the flow direction on the substrate surface.
5. By alteration the flow direction, and applying layer-by-layer scheme we can get multiple cross-bars out of the NW arrays, which is supposed to be the most important configuration for the devices we made from NWs.
6. By patterning the surface, we can get the NWs aligned (positioned) in a certain place, thus make it possible to create more regular arrays of devices.

Patterning process: I. a layer of PMMA was spin-coated on the substrate surface, then use EBL (Electron Beam Lithography) to write pattern, i.e. to selectively exposed Si surface which was later chemically finctionalized. (as in 2). II. Now we have the PMMA trenches, the bottom of which is exposed Si surface covered with —NH$_2$ SAM. When we flow NW suspensions over these patterns, (as described in 4, 5, just the surface in this case is patterned), the NWs will be directed into PMMA trenches. At last we lift off the PMMA, together with the NWs stick on PMMA surface. So only those stay on the bottom of the PMMA trenches left on the substrate surface, thus we get clean arrays of devices.

Directed Assembly of One Dimensional Nanostructures into Functional Networks

One-dimensional nanostructures, such as nanowires and nanotubes, represent the smallest dimension for efficient transport of electrons and excitons, and thus are ideal building blocks for hierarchical assembly of functional nanoscale electronic and photonic structures. We report an approach for the hierarchical assembly of one-dimensional nanostructures into well-defined functional networks. We show that nanowires can be assembled into parallel arrays with control of the average separation, and by combining fluidic alignment with surface patterning techniques that it is also possible to control periodicity. In addition, complex crossed nanowire arrays can be prepared using layer-by-layer assembly with different flow directions for sequential steps. Transport studies show that the crossed nanowire arrays form electrically conducting networks, with individually addressable device function at each cross point.

Nanoscale materials, for example, nanoclusters and nanowires (NWs), represent attractive building blocks for hierarchical assembly of functional nanoscale devices that could overcome fundamental and economic limitations of conventional lithography-based fabrication. Research focused on zero-dimensional nanoclusters has led to significant advances, including the assembly of arrays with order extending from nanometer to micrometer length scales. In contrast, the assembly of one-dimensional (1D) nanostructures, such as NWs and carbon nanotubes (NTs), has met with much less success, although these materials offer great potential as building blocks for applications in nanoelectronics and photonics.

To achieve the substantial potential of NWs and NTs in these and other areas of nanotechnology, will require the controlled and predictable assembly of well-ordered structures. We report an approach for hierarchical assembly of 1D nanostructures whereby NWs are aligned in fluid flows with the separation and spatial location readily controlled. Crossed NW arrays were also prepared using layer-by-layer assembly with different flow directions for sequential steps. Transport studies show that the crossed NW arrays form electrically conducting networks, with individually addressable device function at each NW/NW cross point. This approach can be potentially used for organizing other 1D nanostructures into highly integrated device arrays, and thus offers a general pathway for bottom-up assembly of new electronic and photonic nanosystems.

Figure 30A:
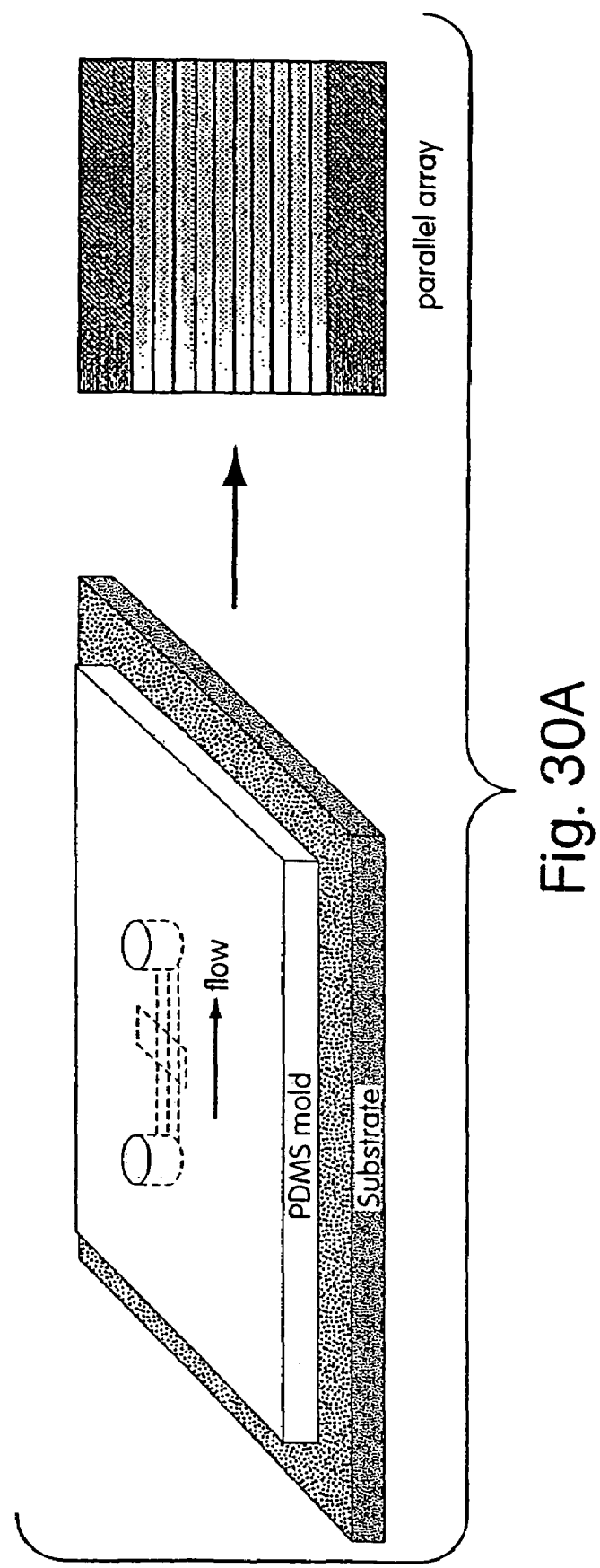
FIGS. 30A and 30B are schematics of fluidic channel structures for flow assembly.
Figure 30B:
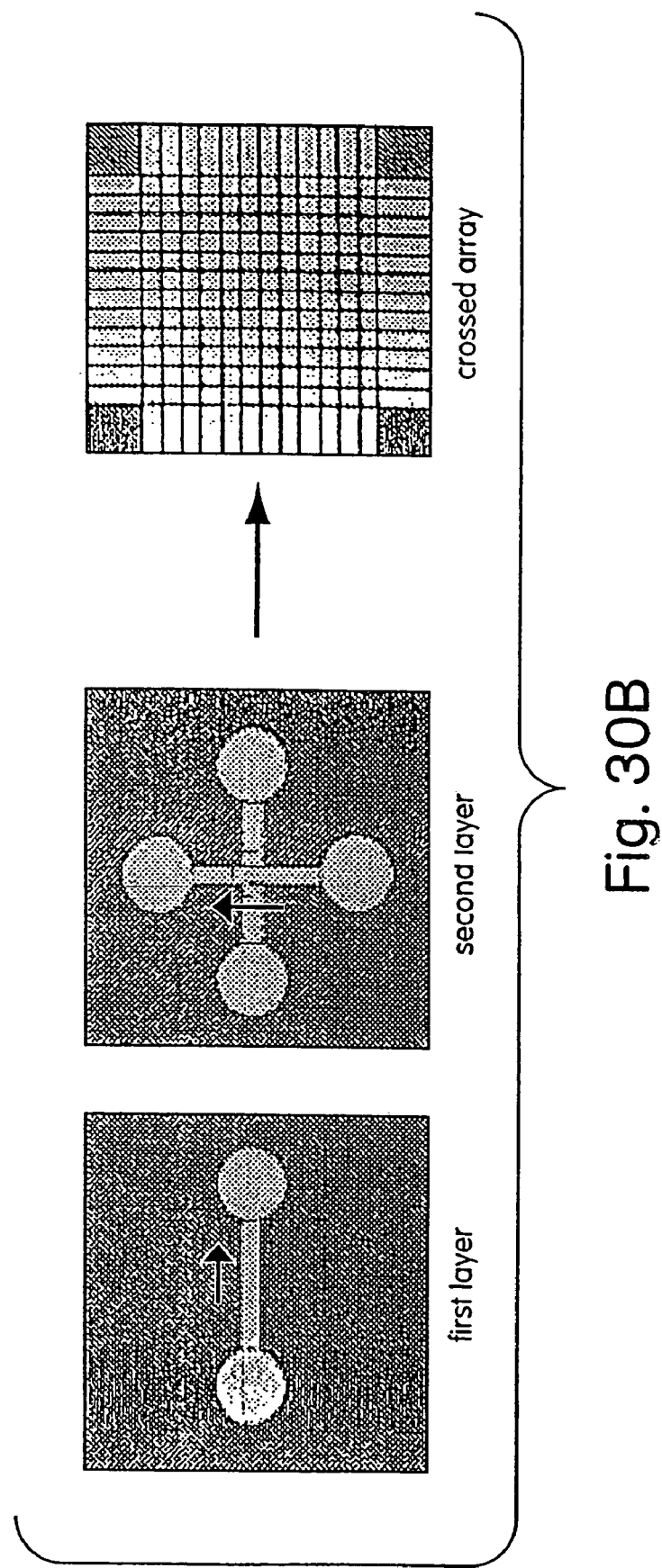

The gallium phosphide (GaP), indium phosphide (InP) and silicon (Si) NWs used in these studies were synthesized by laser assisted catalytic growth, and subsequently suspended in ethanol solution. In general, we have assembled arrays of NWs by passing suspensions of the NWs through fluidic channel structures formed between a poly(dimethylsiloxane) (PDMS) mold and a flat substrate (FIG. 30A and 30B). Parallel and crossed arrays of NWs can be readily achieved using single (FIG. 30A) and sequential crossed (FIG. 30B) flows, respectively, for the assembly process as described below.

A typical example of parallel assembly of NWs (FIG. 31A) shows that virtually all the NWs are aligned along one direction; i.e. the flow direction. There are also some small deviations with respect to the flow direction, which we will discuss below. Examination of the assembled NWs on larger length scales (FIG. 31B) shows that the alignment readily extends over hundreds of micrometers. Indeed, alignment of the NWs has been found to extend up to millimeter length scales, and seem to be limited by the size of the fluidic channels, based on experiments carried out using channels with widths ranging from 50 to 500 µm and lengths from 6-20 mm.

Figure 31A:
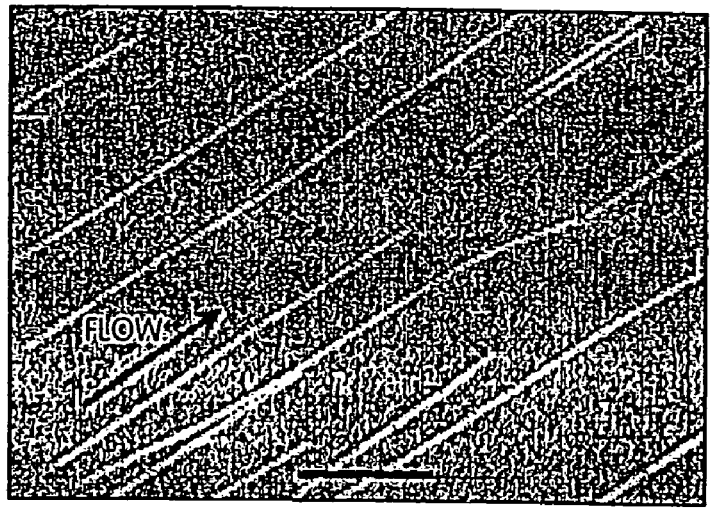
FIGS. 31A-31D illustrate parallel assembly of nanowire arrays.

We have carried out several types of experiments to understand factors controlling the alignment and average separation of the NWs. First, we find that the degree of alignment can be controlled by the flow rate. With increasing flow rates, the width of the NW angular distribution with respect to the flow direction (e.g., inset FIG. 31C) significantly narrows. Comparison of the distribution widths measured over a range of conditions shows that the width decreases quickly from our lowest flow rate, ~4 mm/s, and approaches a nearly constant value at ~10 mm/s (FIG. 31C). At the highest flow rates examined in our studies, more than 80% of the NWs are aligned within ±5 degrees of the flow direction (inset, FIG. 31C). Our observed results can be explained within the framework of shear flow. Specifically, the channel flow near the substrate surface resembles a shear flow and aligns the NWs in the flow direction before they are immobilized on the substrate. Higher flow rates produce larger shear forces, and hence lead to better alignment.

Figure 31B:
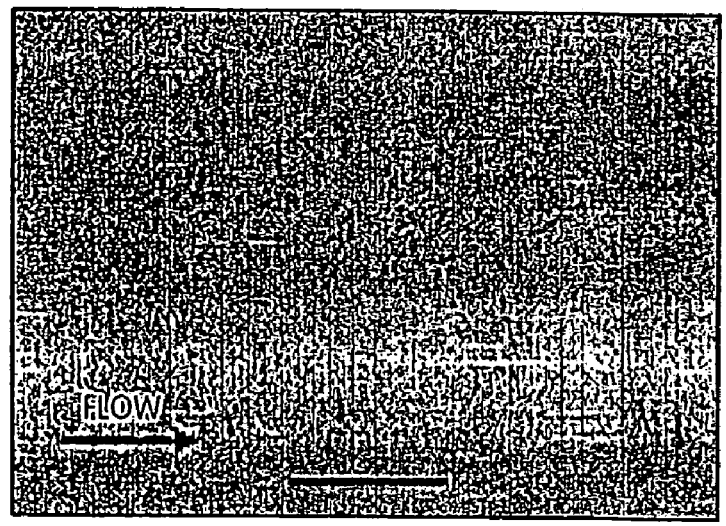
Figure 31C:
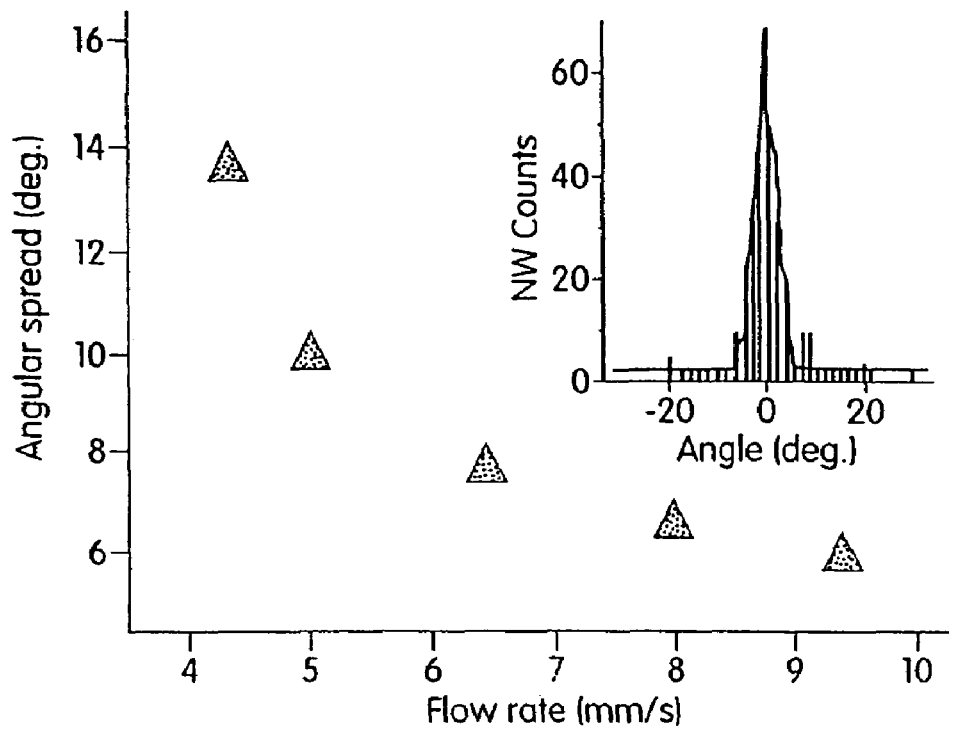
Figure 31D:
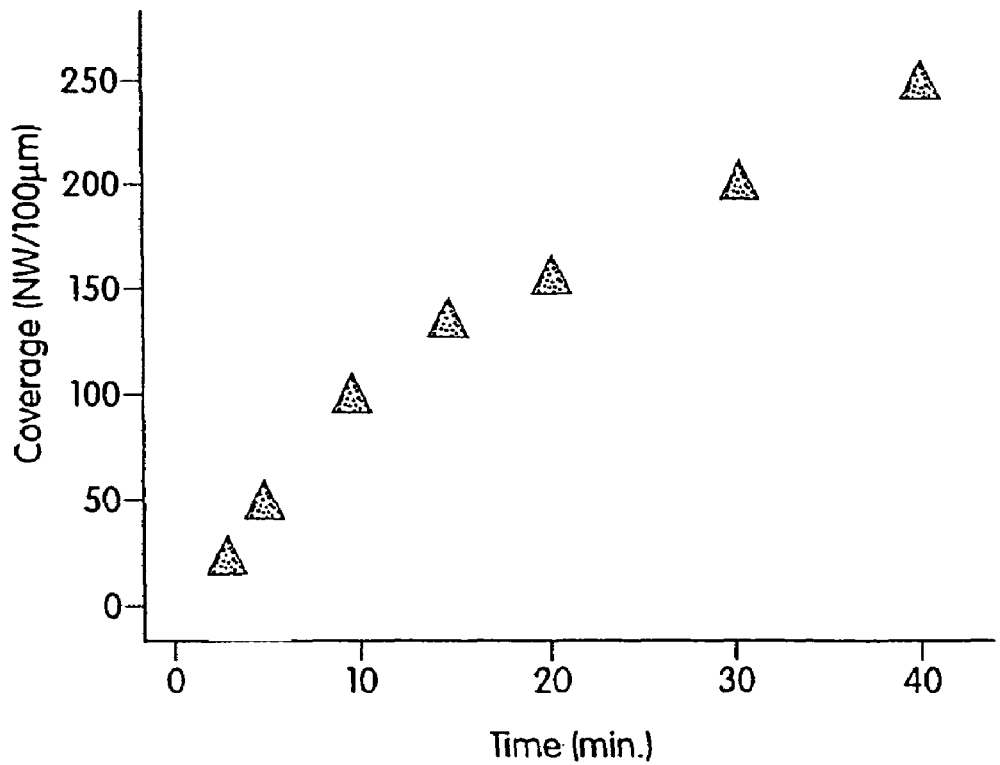

In addition, the average NW surface coverage can be controlled by the flow duration (FIG. 31D). Experiments carried out at constant flow rate show that the NW density increases systematically with flow duration. In these experiments, a flow duration of 30 min produced a density of ca. 250 NWs/100 µm or an average NW/NW separation of ~400 nm. Extended deposition time can produce NW arrays with spacings on the order of 100 nm or less. We note that the deposition rate and hence average separation versus time depends strongly on the surface chemical functionality. Specifically, we have shown that the GaP, InP and Si NWs deposit more rapidly on amino-terminated monolayers, which possesses a partial positive charge, than on either methyl-terminated monolayers or bare $SiO_2$ surfaces. It is also important to recognize that the minimum separation of aligned NWs that can be achieved without NW-NW contacts will depend on the lengths of the NWs used in the assembly process. Recent progress demonstrating control of NW lengths from the 100 nanometer to tens of micrometer scale should increase the range of accessible spacings without contact.

Figure 32A:
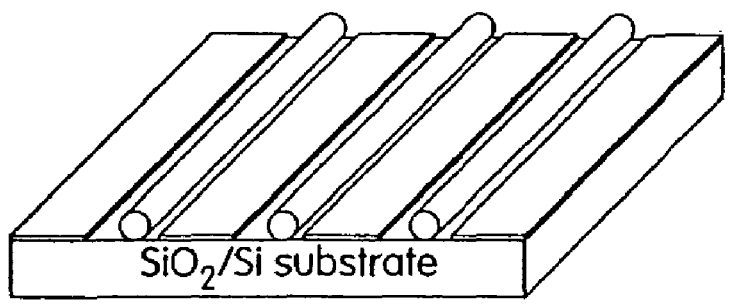
FIGS. 32A-32D illustrate assembly of periodic nanowire arrays.

Our results demonstrate ordering of NW structure over multiple length scales-organization of nanometer diameter wires with 100 nm to micrometer scale separations over millimeter scale areas. This hierarchical order can readily bridge the microscopic and macroscopic worlds, although to enable assembly with greatest control requires that the spatial position also be defined. We have achieved this important goal by utilizing complementary chemical interactions between chemically patterned substrates and NWs (FIG. 32A). SEM images of representative experiments (FIGS. 32B-32D) show parallel NW arrays with lateral periods the same as those of the surface patterns. These data demonstrate that the NWs are preferentially assembled at positions defined by the chemical pattern, and moreover, show that the periodic patterns can organize the NWs into a regular superstructure. It is important to recognize that the patterned surface alone does not provide good control of the 1D nanostructure organization. Assembly of NTs and NWs on patterned substrates shows 1D nanostructures aligned with, bridging, and looping around patterned areas with little directional control. Our use of fluid flows avoids these significant problems and enables controlled assembly in one or more directions. By combining this approach with other surface patterning methods, such as nanoscale domain formation in diblock copolymers and spontaneous ordering of molecules, it should be possible to generate well-ordered NW arrays beyond the limitations of conventional lithography.

Figure 33A:
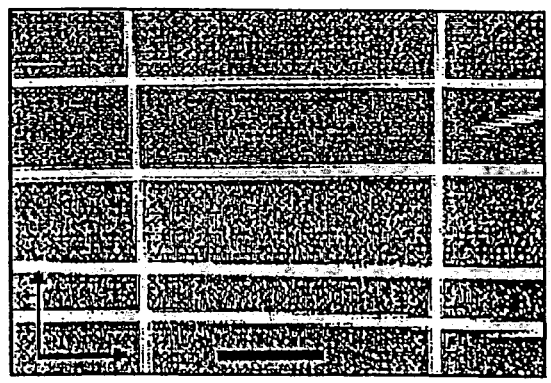
FIGS. 33A-33E illustrate layer-by-layer assembly and transport measurements of crossed nanowire arrays.
Figure 33B:
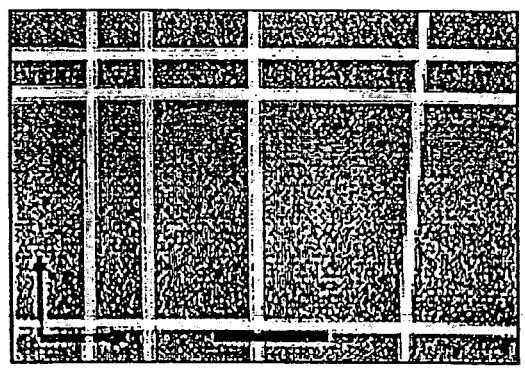

Our general approach can be used to organize NWs into more complex crossed structures, which are critical for building dense nanodevice arrays, using the layer-by-layer scheme illustrated in FIG. 31B. The formation of crossed and more complex structures requires that the nanostructure-substrate interaction is sufficiently strong that sequential flow steps do not affect preceding ones: we find that this condition can be achieved. For example, alternating the flow in orthogonal directions in a two-step assembly process yields crossbar structures (FIG. 33A and 33B). Both FIGS. show that multiple crossbars can be obtained with only hundreds of nanometer separations between individual cross points in a very straightforward, low cost, fast and scalable process. Although the separations between individual NWs are not completely uniform, a periodic array can be easily envisioned using a patterned surface as described above. Significantly, these crossbar structures can yield finctional devices (see below).

We believe that our approach for directed assembly of multiple crossed NW arrays offers significant advantages over current efforts, which have used random deposition, direct manipulation of individual NWs and NTs and electric fields to make single crossed structures. With random deposition and manipulation it is difficult to obtain multiple crossbars required for integrated nanodevices. While electric fields enable more control over assembly, this method is also limited by (i) electrostatic interference between nearby electrodes as separations are scaled below the micrometer level and (ii) the requirement of extensive lithography to fabricate the electrodes for assembly of multiple NW device structures. Our fluidic approach is intrinsically very parallel and scalable, and moreover, it allows for the directed assembly of geometrically complex structures by simply controlling the angles between flow directions in sequential assembly steps. For example, an equilateral triangle (FIG. 33C) was assembled in a three-layer deposition sequence using 60° angles between the three flow directions. The method of flow alignment thus provides a flexible way to meet the requirements of many device configurations, including those requiring assembly of multiple 'layers' of NWs.

Electric fields can be used to align suspensions of semiconductor NWs into parallel NW arrays and single NW crosses, where patterned micro-electrode arrays are used to create a field pattern. Fringing fields and charging can, however, lead to significant complications in the assembly of multiple crosses at the submicron scale.

An important feature of this layer-by-layer assembly scheme is that each layer is independent of the others, and thus a variety of homo- and hetero-junction configurations can be obtained at each crossed point by simply changing the composition of the NW suspension used for each step. For example, it should be possible to directly assemble and subsequently address individual nanoscale devices using our approach with n-type and p-type NWs and NTs, in which the NWs/NTs act as both the wiring and active device elements. A typical 2×2 crossbar array made of n-type InP NWs, in which all eight ends of the NWs are connected by metal electrodes, demonstrates this point (FIG. 33D). Transport measurements (FIG. 33E) show that current can flow through any two of the eight ends, and enable the electrical characteristics of individual NWs and the NW-NW junctions to be assessed. The current-voltage (I-V) data recorded for each of the four cross points exhibit linear or nearly linear behavior (curves 200), and are consistent with expectations for n-n type junctions. Because single NW/NW p-n junctions formed by random deposition exhibit behavior characteristic of light-emitting diodes (LEDs), we believe it is apparent that our approach could be used to assemble high-density and individually addressable nanoLEDs and electronically more complex nanodevices.

These studies provide a general and rational approach for hierarchical assembly of 1D nanomaterials into well-defined functional networks that can bridge the nanometer through millimeter size regimes. We have shown that NWs can be assembled into parallel arrays with control of the average separation, and by combining fluidic alignment with surface patterning techniques that it is also possible to control periodicity. In addition, we have demonstrated the possibility of layer-by-layer assembly of crossed and more complex structures by varying the flow direction in sequential steps, and have obtained preliminary results suggesting that this approach can be extended to 1D nanostructures, such as carbon NTs. We believe that flow assembly represents a general strategy for organization of NW and NT building blocks into structures needed for wiring, interconnects and functional devices, and thus could enable a bottom-up manufacturing paradigm for future nanotechnologies.

Additional studies show that suspensions of single-walled carbon nanotubes and duplex DNA can be aligned in parallel arrays using the fluidic approach.

FIGS. 30A and 30B are schematics of fluidic channel structures for flow assembly. FIG. 30A shows a channel formed when the PDMS mold was brought in contact with a flat substrate. NW assembly was carried out by flowing a NW suspension inside the channel with a controlled flow rate for a set duration. Parallel arrays of NWs are observed in the flow direction on the substrate when the PDMS mold is removed. FIG. 30B illustrates that multiple crossed NW arrays can be obtained by changing the flow direction sequentially in a layer-by-layer assembly process.

FIGS. 31A-31D illustrate parallel assembly of NW arrays. FIGS. 31A and 31B are SEM images of parallel arrays of InP NWs aligned in channel flow. The scale bars correspond to 2 μm and 50 μm in FIGS. 31A and 31B, respectively. The silicon ($SiO_2$/Si) substrate used in flow assembly was functionalized with an amino-terminated self assembled monolayer (SAM) by immersion in a 1mM chloroform solution of 3-aminopropyltriethoxysilane (APTES) for 30 min, followed by heating at 110° C. for 10 min. All of the substrates used in the following experiment were functionalized in a similar way unless otherwise specified. FIG. 31C shows NW angular spread with respect to the flow direction vs. flow rate. Each data point in the FIG. was obtained by statistical analysis of angular distribution of ~200 NWs (e.g., see inset). The inset shows histogram of NW angular distribution at a flow rate of 9.40 mm/s. FIG. 31D shows the average density of NW arrays vs. flow time. The average density was calculated by dividing the average number of NWs at any cross section of the channel by the width of the channel. All of the experiments were carried out with a flow rate of 6.40 mm/s.

Figure 32B:
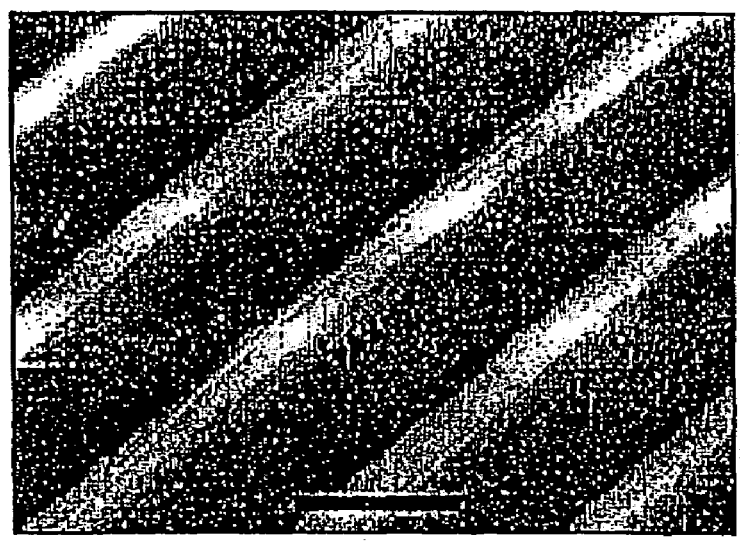
Figure 32C:
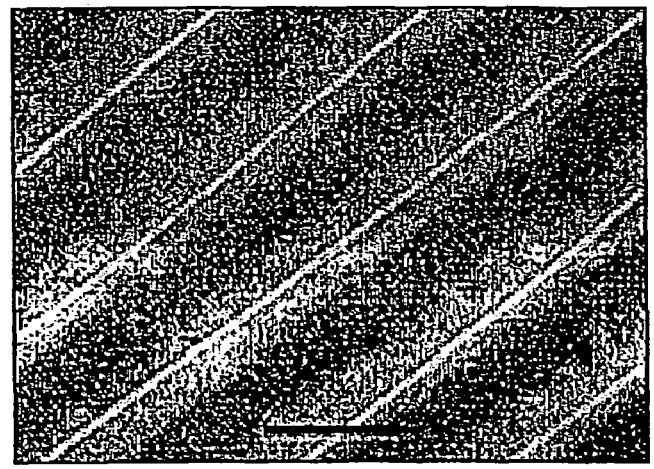
Figure 32D:
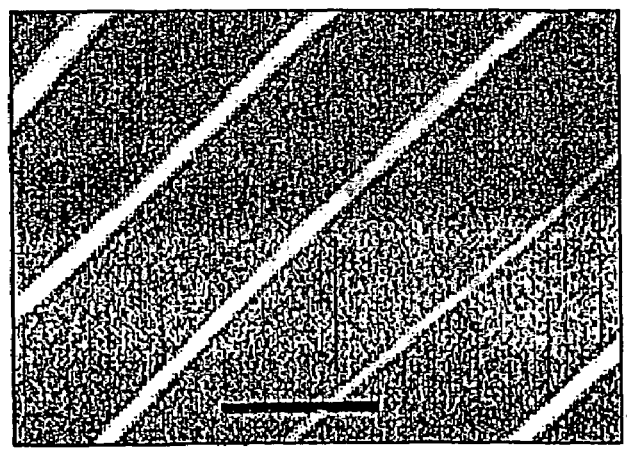

FIGS. 32A-32D illustrate assembly of periodic NW arrays. FIG. 32A is a schematic view of the assembly of NWs onto a chemically patterned substrate. The light gray areas correspond to amino-terminated surfaces, while the dark gray area corresponds to either methyl-terminated or bare surfaces. NWs are preferentially attracted to the amino-terminated regions of the surface. FIGS. 32B and 32C show parallel arrays of GaP NWs aligned on poly(methylmethacrylate) (PMMA) patterned surface with 5 μm and 2 μm separation. The dark regions in the image correspond to residual PMMA, while the bright regions correspond to the amino-terminated $SiO_2$/Si surface. The NWs are preferentially attracted to amino-terminated regions. The PMMA was patterned with standard electron beam (E-beam) lithography, and the resulting $SiO_2$ surface was functionalized by immersing in a solution of 0.5% APTES in ethanol for 10 min, followed by 10 min at 100 ° C. The scale bars correspond to 5 μm and 2 μm in FIGS. 32B and 32C, respectively. FIG. 32D shows parallel arrays of GaP NWs with 500 nm separation obtained using a patterned SAM surface. The $SiO_2$/Si surface was first functionalized with methyl-terminated SAM by immersing in pure hexamethyldisilazane (HMDS) for 15 min at 50 ° C., followed by 10 min at 110° C. This surface was patterned by E-beam lithography to form an array of parallel features with 500 nm period, followed by functionalization using APTES. The scale bar corresponds to 500 nm.

Figure 33C:
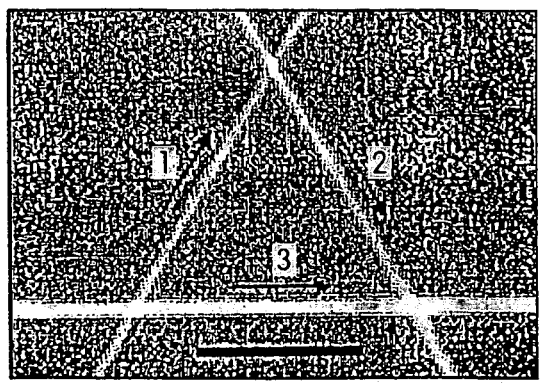
Figure 33D:
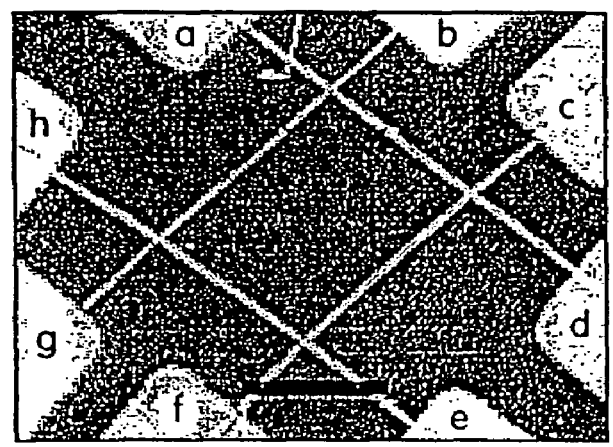
Figure 33E:
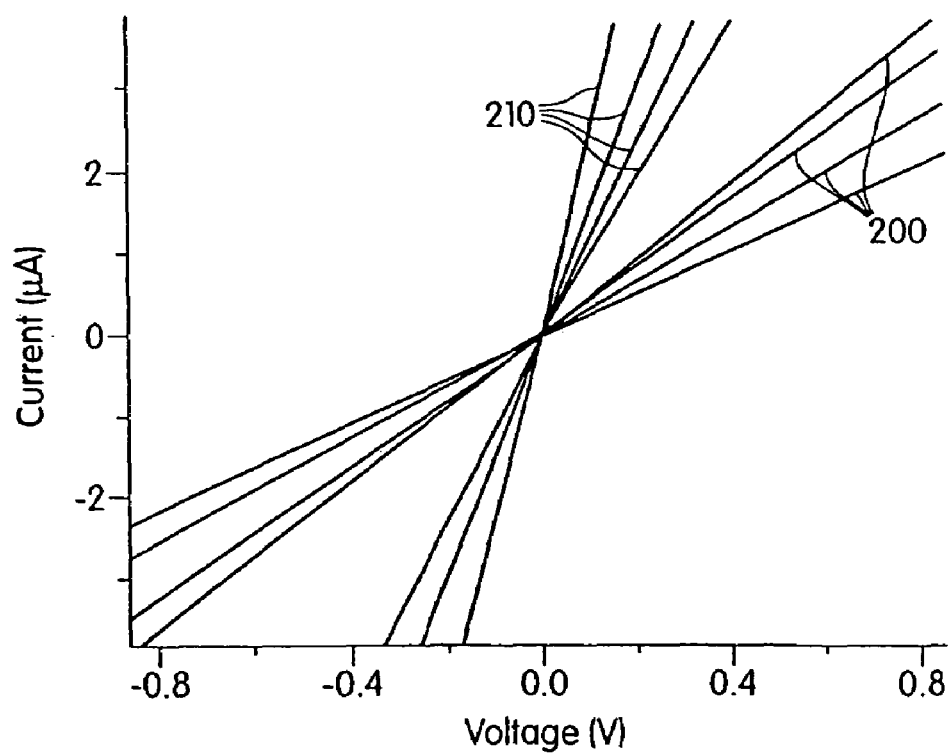

FIGS. 33A-33E illustrate layer-by-layer assembly and transport measurements of crossed NW arrays. FIGS. 33A and 33B show typical SEM images of crossed arrays of InP NWs obtained in a two-step assembly process with orthogonal flow directions for the sequential steps. Flow directions are highlighted by arrows in the images. FIG. 33C shows an equilateral triangle of GaP NWs obtained in three-step assembly process, with 60° angles between flow directions, which are indicated by numbered arrows. The scale bars correspond to 500 nm in the three images. FIG. 33D shows an SEM image of a typical 2×2 cross array made by sequential assembly of n-type InP NWs using orthogonal flows. Ni/In/Au contact electrodes, which were deposited by thermal evaporation, were patterned by E-beam lithography. The NWs were briefly (3-5 s) etched in 6% HF solution to remove the amorphous oxide outer layer prior to electrode deposition. The scale bar corresponds to 2 μm. FIG. 33E shows representative I-V curves from two-terminal measurements on a 2×2 crossed array. The curves 210 represent the I-V of four individual NWs (ad, bg, cf, eh), and the curves 200 represent I-V across the four n-n crossed junctions (ab, cd, ef, gh).

We have demonstrated field effect transistors, pn junctions, light emission diodes, bipolar transistors, complementary inverters, tunnel diodes. We can make all the existing types of semiconductor devices using nanowires. The following are potential applications:

(1) Chemical and biological sensors
(2) Memory and computing
(3) Photodetector and polarized light detector
(4) Indicating tag using the photoluminescence properties
(5) Single electron transistors
(6) Lasers
(7) Photovoltaic solar cells (8) Ultra-sharp tip for scanning probe microscopy and near-filed imaging (9) Ultra-small electrodes for electrochemical and biological applications

(10) Interconnect wires for nanoelectronics and optoelectronics

(11) Temperature sensors

(12) Pressure sensors

(13) Flow sensors

(14) Mass sensors

(15) Single photon emitters and detectors

(16) Ballistic transport and coherent transport for quantum computing

(17) Spintronics devices

(18) Assembly of nanowires for 2D and 3D photonic bandgap materials

The following is a description of alternate techniques for assembling nanowires to form devices. Fluidics can be used to assemble nanowires.

Nanowires (or any other elongated structures) can be aligned by inducing a flow of nanowire solution on surface, wherein the flow can be a channel flow or flow by any other ways.

Nanowire arrays with controlled position and periodicity can be produced by patterning the surface of the substrate and/or conditioning surface of the nanowires with different functionalities.

Wherein the position and periodicity control is achieved by designing specific complementary forces (chemical or biological or electrostatic or magnetic or optical) between the patterned surface and wires, such as A wire goes to A' patterned area, B wire goes to B' patterned area, C wire goes to C' patterned area, etc.

Wherein the surface of the substrate and/or nanowires can be conditioned with different molecules/materials, or different charges, different magnetos or different light intensities (e.g., by interference/diffraction patterns from light beams) or a combination of these.

As-assembled nanowire arrays could also be transferred to another substrate (e.g. by stamping).

Nanowires can be assembled by complementary interaction. Flow is used for assembly of nanowires in the above methods, although it is not limited to flow only. Complementary chemical, biological, electrostatic, magnetic or optical interactions alone can also be exploited for nanowire assembly (although with less control).

Nanowires can be assembled using physical patterns. Deposit nanowire solution onto substrate with physical patterns, such as surface steps, trenches, etc.

Nanowires can be aligned along the corner of the surface steps or along the trenches.

Physical patterns can be formed by the natural crystal lattice steps or self-assembled diblock copolymer stripes, or imprinted patterns or any other patterns.

Nanowires may be assembled by electrostatic or magnetic force between nanowires. By introducing charge onto nanowire surface, electrostatic forces between nanowires can align them into certain patterns, such as parallel arrays.

Nanowires can be assembled using a LB film. Nanowires were first surface conditioned and dispersed to the surface of a liquid phase to form a Langmuir-Blodgett (LB) film. Nanowires can then be aligned into different patterns (such as parallel arrays) by compressing the surface. Then the nanowire patterns can be transferred onto desired substrate.

Nanowires can be assembled by shear stretching by dispersing nanowires in a flexible matrix (which could be polymers), followed by stretching the matrix in one direction, nanowires can be aligned in the stretching direction by the shear force induced. The matrix can then be removed and the aligned nanowire arrays can be transferred to desired substrate.

Wherein the stretching of the matrix can be induced by mechanical, electrical optical, magnetic force. And the stretching direction could be either in the plane of the substrate or not.

Having now described some illustrative embodiments of the invention claimed below, it should be apparent to those skilled in the art that the foregoing is merely illustrative and not limiting, having been presented by way of example only. Numerous modification and other illustrative embodiments are within the scope of one of ordinary skill in the art and are contemplated as falling within the scope of the claims set forth below. In particular, although many of the examples presented herein involve specific combinations of method acts or system elements, it should be understood that those acts and those elements may be combined in other ways to accomplish the same objectives. Acts, elements and features discussed only in connection with one embodiment of a system or method are not intended to be excluded from a similar role in other embodiments. Further, for the one or more means-plus-function limitations recited in the following claims, the means are not intended to be limited to the means disclosed herein for performing the recited function, but are intended to cover in scope any equivalent means, known now or later developed, for performing the recited function.

What is claimed is:

1. A method of assembling a plurality of elongated structures on a surface of a substrate, wherein one or more of the elongated structures are at least one of the following: a single crystal, an elongated semiconductor that, at any point along its longitudinal axis, has a largest cross-sectional dimension less than 500 nanometers, and a free-standing semiconductor with at least one portion having a smallest width of less than 500 nanometers, and wherein the method comprises acts of:
   (A) providing the one or more elongated structures;
   (B) thereafter, dispersing the one or more elongated structures on a surface of a liquid phase to form a Langmuir-Blodgett film;
   (C) compressing the Langmuir-Blodgett film; and
   (D) transferring the compressed Langmuir-Blodgett film onto a surface of the substrate.

2. The method of claim 1, wherein the one or more elongated structures comprises a nanowire.

3. The method of claim 1, wherein the one or more elongated structures comprises a semiconductor nanowire.

4. The method of claim 3, wherein the semiconductor nanowire is doped during growth of the nanowire.

5. The method of claim 3, wherein the semiconductor nanowire is grown catalytically from a catalyst particle.

6. The method of claim 3, wherein the semiconductor nanowire is grown using laser-assisted catalytic growth.

7. The method of claim 1, wherein the one or more elongated structures comprises a bulk-doped semiconductor nanowire.

8. The method of claim 1, wherein the one or more elongated structures has at least one portion having a smallest width of less than 500 nanometers.

9. The method of claim 1, further comprising orienting the plurality of elongated structures using an electric field to align the plurality of elongated structures on the surface of the substrate.

10. The method of claim 1, further comprising generating an electric field between at least two electrodes, and positioning the plurality of elongated structures between the electrodes.

* * * * *